United States Patent
Hickman

(10) Patent No.: US 10,386,360 B2
(45) Date of Patent: Aug. 20, 2019

(54) BIO-MICROELECTROMECHANICAL SYSTEM TRANSDUCER AND ASSOCIATED METHODS

(71) Applicant: University of Central Florida Research Foundation, Inc., Orlando, FL (US)

(72) Inventor: James Hickman, Orlando, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 263 days.

(21) Appl. No.: 15/594,697

(22) Filed: May 15, 2017

(65) Prior Publication Data
US 2018/0095073 A1    Apr. 5, 2018

Related U.S. Application Data

(63) Continuation of application No. 12/661,323, filed on Mar. 15, 2010, now abandoned.
(Continued)

(51) Int. Cl.
*G01N 33/50*    (2006.01)
*G01N 33/483*   (2006.01)
(Continued)

(52) U.S. Cl.
CPC ..... *G01N 33/5061* (2013.01); *G01N 33/4833* (2013.01); *G01Q 60/38* (2013.01); *G01N 2203/0051* (2013.01); *H01L 41/1136* (2013.01)

(58) Field of Classification Search
CPC ....... G01N 2203/0051; G01N 33/5061; G01N 33/4833; H01L 41/1136
See application file for complete search history.

(56) References Cited

U.S. PATENT DOCUMENTS

| 5,442,510 A | 8/1995 | Schwartz et al. |
| 5,682,899 A | 11/1997 | Nashef et al. |

(Continued)

FOREIGN PATENT DOCUMENTS

| CA | 2788905 A1 | 8/2011 |
| CA | 2798777 C | 9/2016 |

(Continued)

OTHER PUBLICATIONS

Abbanat D, et al. (2003) Novel antibacterial agents for the treatment of serious Gram-positive infections. Expert Opin Investig Drugs. 12: 379-399.

(Continued)

*Primary Examiner* — Jonathan M Hurst
(74) *Attorney, Agent, or Firm* — Meunier Carlin & Curfman LLC

(57) ABSTRACT

The invention discloses a bio-MEMS transducer comprising a cultured myotube and a piezoelectric microcantilever having the myotube attached thereto along a lengthwise extent of said microcantilever. The transducer may include an input/output processor operably connected with said piezoelectric microcantilever to process electrical signals received therefrom and to send electrical signals thereto. The invention may operate as a biosensor wherein the attached myotube contracts on contact with a sensed agent, the myotube contraction deflecting the microcantilever to generate a piezoelectric signal therefrom. The invention may also be used as a biosensor for quantitating physiologic response to an agent by measuring deflection of the cantilever caused by myotube contraction elicited by contact with the agent; and correlating the measurement to effectiveness of the sensed agent in causing a myotube physiologic response. The bio-transducer is a bioactuator when an (Continued)

applied electrical signal causes the piezoelectric microcantilever to deflect, thereby actuating the attached myotube.

20 Claims, 20 Drawing Sheets

Related U.S. Application Data

(60) Provisional application No. 61/259,715, filed on Nov. 10, 2009, provisional application No. 61/159,851, filed on Mar. 13, 2009.

(51) Int. Cl.
*G01Q 60/38* (2010.01)
*H01L 41/113* (2006.01)

(56) References Cited

U.S. PATENT DOCUMENTS

| | | |
|---|---|---|
| 5,948,621 A | 9/1999 | Turner et al. |
| 6,866,383 B2 | 3/2005 | Naik et al. |
| 6,916,541 B2 | 7/2005 | Pantano et al. |
| 6,935,165 B2 | 8/2005 | Bashir et al. |
| 7,384,786 B2 | 6/2008 | Freyman et al. |
| 7,541,146 B2 | 6/2009 | Lewis |
| 7,579,189 B2 | 8/2009 | Freyman et al. |
| 7,691,629 B2 | 4/2010 | Johe et al. |
| 7,860,563 B2 | 12/2010 | Linderoth et al. |
| 7,923,015 B2 | 4/2011 | Vazquez-Martinez et al. |
| 7,927,671 B2 | 4/2011 | Kato |
| 8,071,319 B2 | 12/2011 | Metzger et al. |
| 8,178,602 B2 | 5/2012 | Mao et al. |
| 8,318,488 B1 | 11/2012 | Bohlen et al. |
| 8,318,489 B2 | 11/2012 | Davidson et al. |
| 8,318,951 B2 | 11/2012 | Olson et al. |
| 8,828,721 B1 | 9/2014 | Rumsey et al. |
| 2003/0065452 A1 | 4/2003 | Hickman |
| 2003/0144823 A1 | 7/2003 | Fox et al. |
| 2003/0211542 A1 | 11/2003 | Lee et al. |
| 2005/0074834 A1 | 4/2005 | Chaplen et al. |
| 2006/0058607 A1* | 3/2006 | Garcia-Webb ........... G01N 3/38 600/407 |
| 2006/0105457 A1 | 5/2006 | Rameshwar |
| 2006/0259992 A1 | 11/2006 | Koren et al. |
| 2007/0015138 A1 | 1/2007 | Barlow et al. |
| 2007/0037225 A1 | 2/2007 | Metzger et al. |
| 2007/0089515 A1 | 4/2007 | Shih et al. |
| 2007/0117217 A1 | 5/2007 | Lal et al. |
| 2007/0122896 A1 | 5/2007 | Shuler et al. |
| 2007/0129447 A1 | 6/2007 | Sra et al. |
| 2007/0212723 A1 | 9/2007 | Dudley et al. |
| 2007/0218534 A1 | 9/2007 | Klenerman et al. |
| 2008/0124789 A1 | 5/2008 | Hickman |
| 2008/0138797 A1 | 6/2008 | Hunt et al. |
| 2008/0166795 A1 | 7/2008 | Shuler et al. |
| 2008/0227137 A1 | 9/2008 | Zhang et al. |
| 2009/0029463 A1 | 1/2009 | Collins |
| 2009/0078023 A1 | 3/2009 | Mutharasan et al. |
| 2009/0226768 A1* | 9/2009 | Wang ........................ H02N 2/18 429/2 |
| 2009/0227469 A1 | 9/2009 | Conklin et al. |
| 2009/0239940 A1 | 9/2009 | Del Monte et al. |
| 2009/0305319 A1 | 12/2009 | Baudenbacher et al. |
| 2010/0028902 A1 | 2/2010 | Brown et al. |
| 2011/0250682 A1 | 10/2011 | Hickman et al. |
| 2012/0122728 A1 | 5/2012 | Hickman et al. |
| 2012/0128639 A1 | 5/2012 | Hickman et al. |
| 2012/0135452 A1 | 5/2012 | Shuler et al. |
| 2012/0142556 A1 | 6/2012 | Parker et al. |
| 2013/0096888 A1 | 4/2013 | Hickman et al. |
| 2013/0115694 A1 | 5/2013 | Hickman et al. |
| 2014/0274796 A1 | 9/2014 | Hickman et al. |
| 2015/0219622 A1 | 8/2015 | Hickman |

FOREIGN PATENT DOCUMENTS

| | | |
|---|---|---|
| EP | 2435585 A1 | 2/2013 |
| EP | 2585171 A1 | 11/2013 |
| EP | 2434896 A1 | 1/2014 |
| EP | 2531910 B1 | 4/2015 |
| WO | 2001029206 A1 | 4/2001 |
| WO | 2005033264 A1 | 4/2005 |
| WO | 2005108598 A1 | 11/2005 |
| WO | 2009036573 A1 | 3/2009 |
| WO | 2010127280 A1 | 5/2010 |
| WO | 2010138679 A1 | 12/2010 |
| WO | 2010138782 A1 | 12/2010 |
| WO | 2011097574 A1 | 8/2011 |
| WO | 2011133985 A1 | 10/2011 |
| WO | 2012158923 A1 | 6/2012 |
| WO | 2013013206 A1 | 1/2013 |
| WO | 2014028940 A1 | 2/2014 |
| WO | 2014120952 A1 | 8/2014 |

OTHER PUBLICATIONS

Abdi H. (2003) Multivariate Analysis. Encyclopedia of Social Sciences Research Methods. M. Lewis-Beck, A. Bryman and T. Futing. Thousand Oaks (CA), Sage.

Adell A, et al. (2002) Origin and functional role of the extracellular serotonin in the midbrain raphe nuclei. Brain Res Brain Res Rev. 39: 154-180.

Agarwal A, et al. (2013) Microfluidic heart on a chip for higher throughput pharmacological studies. Lab Chip. 13: 3599-3608.

Ahern CA, et al. (2003) Ca2+ current and charge movements in skeletal myotubes promoted by the beta-subunit of the dihydropyridine receptor in the absence of ryanodine receptor type 1. Biophys J. 84: 942-959.

Ahmari SE, et al. (2000) Assembly of presynaptic active zones from cytoplasmic transport packets. Nat Neurosci. 3: 445-451.

Ahuja TK, et al. (2007) Hippocampal slice cultures integrated with multi-electrode arrays: A model for study of long-term drug effects on synaptic activity. Drug Development Research. 68: 84-93.

Ainscow EK and Brand MD. (1999) Internal regulation of ATP turnover, glycolysis and oxidative phosphorylation in rat hepatocytes. Eur J Biochem. 266: 737-749.

Akaaboune M, et al. (2000) Developmental regulation of amyloid precursor protein at the neuromuscular junction in mouse skeletal muscle. Mol Cell Neurosci. 15: 355-367.

Akanda N, et al. (2008) Effect of malonate, a metabolic pathway inhibitor, on action potential peak shape and the relationship to cellular pathways. 38th Annual Meeting of the Society for Neuroscience. vol. 38.

Akanda N, et al. (2009) Analysis of toxin-induced changes in action potential shape for drug development. J Biomol Screen. 14: 1228-1235.

Alabed YZ, et al. (2006) Neuronal responses to myelin are mediated by rho kinase. J Neurochem. 96: 1616-1625.

Albensi BC. (2003) A comparison of drug treatment versus electrical stimulation for suppressing seizure activity. Drug News Perspect. 16: 347-352.

Albert R and Othmer H. (2003) The topology of the regulatory interactions predicts the expression pattern of the segment polarity genes in *Drosophila melanogaster*. J Theor Biol. 223: 1-18.

Albert Y, et al. (2005) Transcriptional regulation of myotube fate specification and intrafusal muscle fiber morphogenesis. J Cell Biol. 169: 257-268.

Alexander SL, et al. (1989) An atomic-resolution atomic-force microscope implemented using an optical lever. J Appl Phys. 65: 164-167.

Al-Shanti N, et al. (2008) Beneficial synergistic interactions of TNF-alpha and IL-6 in C2 skeletal myoblasts—potential cross-talk with IGF system. Growth Factors. 26: 61-73.

Alsina B, et al. (2001) Visualizing synapse formation in arborizing optic axons in vivo: dynamics and modulation by BDNF. Nat Neurosci. 4: 1093-1101.

(56) References Cited

OTHER PUBLICATIONS

Alterio J, et al. (1990) Acidic and basic fibroblast growth factor mRNAs are expressed by skeletal muscle satellite cells.Biochem Biophys Res Commun. 166: 1205-1212.
Altmann L. (2000) Multielectrode recordings of synaptic plasticity in brain slices: A new method for the assessment of neurotoxic effects. European Journal of Neuroscience. 12: 29-29.
Amarenco P, et al. (2006) High-dose atorvastatin after stroke or transient ischemic attack. N Engl J Med. 355: 549-559.
Amit M. (2007) Feeder-layer free culture system for human embryonic stem cells. Methods Mol Biol. 407: 11-20.
Anderson DJ, et al. (1997) Cell lineage determination and the control of neuronal identity in the neural crest. Cold Spring Harb Symp Quant Biol. 62: 493-504.
Anderson JE, et al. (1991) Distinctive patterns of basic fibroblast growth factor (bFGF) distribution in degenerating and regenerating areas of dystrophic (mdx) striated muscles. Dev Biol. 147: 96-109.
Andersson Hand van den Berg A. (2004) Microfabrication and microfluidics for tissue engineering: state of the art and future opportunities. Lab Chip. 4: 98-103.
Antzelevitch C. (2001) Transmural dispersion of repolarization and the T wave. Cardiovasc Res. 50: 426-431.
Antzelevitch C. (2005) Cardiac repolarization. The long and short of it. Europace. 7: 3-9.
Aracil A, et al. (2004) Proceedings of Neuropeptides 2004, the XIV European Neuropeptides Club meeting. Neuropeptides. 38: 369-371.
Archer JD, et al. (2006) Persistent and improved functional gain in mdx dystrophic mice after treatment with L-arginine and deflazacort. F ASEB J. 20: 738-740.
Armstrong DL and Rossie S. (1999) Ion channel regulation. Introduction. Adv Second Messenger Phosphoprotein Res. 33: ix-xx.
Arnold HH and Winter B. (1998) Muscle differentiation: more complexity to the network of myogenic regulators. Curr Opin Genet Dev. 8: 539-544.
Arnone MI and Davidson EH. (1997) The hardwiring of development: organization and function of genomic regulatory systems. Development. 124: 1851-1864.
Arsic N, et al. (2004) Vascular endothelial growth factor stimulates skeletal muscle regeneration in vivo. Mol Ther. 10: 844-854.
Askanas V, et al. (1987) De novo neuromuscular junction formation on human muscle fibres cultured in monolayer and innervated by foetal rat spinal cord: ultrastructural and ultrastructural—cytochemical studies. J Neurocytol. 16: 523-537.
Asotra K and Macklin WB. (1993) Protein kinase C activity modulates myelin gene expression in enriched oligodendrocytes. J Neurosci Res. 34: 571-588.
Azzouz M, et al. (2004) VEGF delivery with retrogradely transported lentivector prolongs survival in a mouse ALS model. Nature. 429: 413-417.
Badie N, et al. (2009) A method to replicate the microstructure of heart tissue in vitro using DTMRI-based cell micropatterning. Ann Biomed Eng. 37: 2510-2521.
Badie et al. (2009) Novel micropatterned cardiac cell cultures with realistic ventricular microstructure. Biophysical Journal 96: 3873-3885.
Bahr M, et al. (1991) In vitro myelination of regenerating adult rat retinal ganglion cell axons by Schwann cells. Glia. 4: 529-533.
Baker DC, et al. (2002) The origin and neuronal function of in vivo nonsynaptic glutamate. J Neurosci. 22: 9134-9141.
Bandi E, et al. (2008) Neural agrin controls maturation of the excitation-contraction coupling mechanism in human myotubes developing in vitro. Am J Physiol Cell Physiol. 294: C66-C73.
Bansal R and Pfeiffer SE. (1992) Novel stage in the oligodendrocyte lineage defined by reactivity of progenitors with R-mAb pnor to 01 antigalactocerebroside. J Neurosci Res. 32: 309-316.
Baraban SC, et al. (1997) Osmolarity modulates K+ channel function on rat hippocampal interneurons but not CAI pyramidal neurons. J Physiol. 498: 679-689.

Barbulovic-Nad I, et al. (2008) Digital microfluidics for cell-based assays. Lab Chip. 8: 519-526.
Baron W, et al. (2000) PDGF and FGF-2 signaling in oligodendrocyte progenitor cells: regulation of proliferation and differentiation by multiple intracellular signaling pathways. Mol Cell Neurosci. 15: 314-329.
Barone FC, et al. (1998) Ischemic preconditioning and brain tolerance: temporal histological and functional outcomes, protein synthesis requirement, and interleukin-1 receptor antagonist and early gene expression. Stroke. 29: 1937-1950; discussion 1950-1951.
Behar TN. (2001) Analysis of fractal dimension of 02A glial cells differentiating in vitro. Methods. 24: 331-339.
Belardinelli L, et al. (2003) Assessing predictors of drug-induced torsade de pointes. Trends Pharmacol Sci. 24: 619-625.
Bellamkonda R, et al. (1995) Hydrogel-based three-dimensional matrix for neural cells. J Biomed Mater Res. 29: 663-671.
Bellas E, et al. (2012) In vitro 3D full-thickness skin-equivalent tissue model using silk and collagen biomaterials. Macromol Biosci. 12: 1627-1236.
Benabid AI. (2003) Deep brain stimulation for Parkinson's disease. Curr Opin Neurobiol. 13: 696-706.
Bender A, et al. (2007) Analysis of pharmacology data and the prediction of adverse drug reactions and off-target effects from chemical structure. ChemMedChem. 2: 861-873.
Bentley A and Atkinsona, A. (2001) Whole cell biosensors—electrochemical and optical approaches to ecotoxicity testing. Toxicol In Vitro. 15: 469-475.
Berg MC, et al. (2004) Controlling mammalian cell interactions on patterned polyelectrolyte multilayer surfaces. Langmuir. 20: 1362-1368.
Berger TW, et al. (2001) Brain-implantable biomimetic electronics as the next era in neural prosthetics. Proceedings of the IEEE. 89: 993-1012.
Bernstein M, et al. (1996) Receptor-mediated calcium signalling in glial cells from mouse corpus callosum slices. J Neurosci Res. 46: 152-163.
Bers DM. (2002) Cardiac excitation-contraction coupling. Nature. 415: 198-205.
Bettinger CJ, et al. (2009) Engineering substrate topography at the micro- and nanoscale to control cell function. Angew Chem Int Ed Engl. 48: 5406-5415.
Bhalla US and Iyengar R. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN and Tung L. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by musclederived factors. Development. 111: 221-232.
Bodine SC, et al. (2001) Identification of ubiquitin ligases required for skeletal muscle atrophy. Science. 294: 1704-1708.
Bogler 0, et al. (1990) Cooperation between two growth factors promotes extended self-renewal and inhibits differentiation of oligodendrocyte-type-2 astrocyte (0-2A) progenitor cells. Proc Natl Acad Sci US A. 87: 6368-6372.
Boillee S, et al. (2006) ALS: a disease of motor neurons and their nonneuronal neighbors. Neuron. 52: 39-59.
Boldin SA and Futerman AH. (2000) Up-regulation of glucosylceramide synthesis upon stimulation of axonal growth by basic fibroblast growth factor. Evidence for post-translational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.

(56) References Cited

OTHER PUBLICATIONS

Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al. (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silico simulation of synaptic processes. BMC Bioinformatics. 9 Suppl 4: S7.
Brand T, et al. (2000) EMBO Workshop Report: Molecular genetics of muscle development and neuromuscular diseases Kloster Irsee, Germany, Sep. 26-Oct. 1, 1999. EMBO J. 19: 1935-1941.
Brand-Saberi B and Christ B. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neurol. 148: 475-494.
Bren-Mattison Y and Olwin BB. (2002) Sonic hedgehog inhibits the terminal differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.
Brewer GJ, et al. (2008) NbActiv4 medium improvement to Neurobasal/B27 increases neuron synapse densities and network spike rates on multielectrode arrays. J Neurosci Methods. 170: 181-187.
Brewer GJ. (1997) Isolation and culture of adult rat hippocampal neurons. J Neurosci Methods. 71: 143-155.
Brewer GJ. (1999) Regeneration and proliferation of embryonic and adult rat hippocampal neurons in culture. Exp Neurol. 159: 237-247.
Brito-Martins M, et al. (2008) beta(I)- and beta(2)-adrenoceptor responses in cardiomyocytes derived from human embryonic stem cells: comparison with failing and non-failing adult human heart. Br J Pharmacol. 153: 751-759.
Brockes JP, et al. (1979) Studies on cultured rat Schwann cells. I. Establishment of purified populations from cultures of peripheral nerve. Brain Res. 165: 105-118.
Brokhman I, et al. (2008) Peripheral sensory neurons differentiate from neural precursors derived from human embryonic stem cells. Differentiation. 76: 145-155.
Brumovsky P, et al. (2007) Expression of the vesicular glutamate transporters-1 and -2 in adult mouse dorsal root ganglia and spinal cord and their regulation by nerve injury. Neuroscience. 147: 469-490.
Bult CJ, et al. (1996) Complete genome sequence of the methanogenic archaeon, Methanococcus jannaschii. Science. 273: 1058-1073.
Bunge MB, et al. (1962) Electron microscopic demonstration of connections between glia and myelin sheaths in the developing mammalian central nervous system. J Cell Biol. 12: 448-453.
Bunge RP. (1968) Glial cells and the central myelin sheath. Physiol Rev. 48: 197-251.
Bunge RP. (1993) Expanding roles for the Schwann cell: ensheathment, myelination, trophism and regeneration. Curr Opin Neurobiol. 3: 805-809.
Burdick JA and Vunjak-Novakovic G. (2008) Engineered microenvironments for controlled stem cell differentiation. Tissue Eng Part A. 15: 205-219.
Burgess C, et al. (2008) An endogenous glutamatergic drive onto somatic motoneurons contributes to the stereotypical pattern of muscle tone across the sleep-wake cycle. J Neurosci. 28: 4649-4660.
Butt HJ. (1996) Sensitive Method to Measure Changes in the Surface Stress of Solids. Journal of Colloid and Interface Science. 180: 251-260.
Buzanska L, et al. (2002) Human cord blood-derived cells attain neuronal and glial features in vitro. J Cell Sci. 115: 2131-2138.
Cai J, et al. (2007) Directed differentiation of human embryonic stem cells into functional hepatic cells. Hepatologv. 45: 1229-1239.
Caiozzo VJ, at al. (1992) Response of slow and fast muscle to hypothyroidism: maximal shortening velocity and myosin isoforms. Am J Physiol. 263: C86-C94.
Cakir T, et al. (2007) Reconstruction and flux analysis of coupling between metabolic pathways of astrocytes and neurons: application to cerebral hypoxia. Theor Biol Med Model. 4: 48.
Campbell TJ and Williams KM. (2001) Therapeutic drug monitoring: antiarrhythmic drugs. Br J Clin Pharmacol. 52 Suppl 1: 21S-34S.
Camu Wand Henderson CE. (1992) Purification of embryonic rat motoneurons by panning on a monoclonal antibody to the low-affinity NGF receptor. J Neurosci Methods. 44: 59-70.
Camu W and Henderson CE. (1994) Rapid purification of embryonic rat motoneurons: an in vitro model for studying MND/ALS pathogenesis. J Neurol Sci. 124 Suppl: 73-74.
Cannon JG. (1998) Intrinsic and extrinsic factors in muscle aging. Ann NY Acad Sci. 854: 72-77.
Caratsch CG, et al. (1994) Interferon-alpha, beta and tumor necrosis factor-alpha enhance the frequency of miniature end-plate potentials at rat neuromuscular junction. Neurosci Lett. 166: 97-100.
Carlsson L. (2006) In vitro and in vivo models for testing arrhythmogenesis in drugs. J Intern Med. 259: 70-80.
Carpenedo RL, et al. (2007) Rotary suspension culture enhances the efficiency, yield, and homogeneity of embryoid body differentiation. Stem Cells. 25: 2224-2234.
Carr PA, et al. (1989) Parvalbumin is highly colocalized with calbindin D28k and rarely with calcitonin gene-related peptide in dorsal root ganglia neurons of rat. Brain Res. 497: 163-170.
Carrasco DI and English AW. Neurotrophin 4/5 is required for the normal development of the slow muscle fiber phenotype in the rat soleus. J Exp Biol. 206: 2191-2200.
Caspi O, et al. (2009) In vitro electrophysiological drug testing using human embryonic stem cell derived cardiomyocytes. Stem Cells Dev. 18: 161-172.
Catoire H, et al. (2008) Sirtuin inhibition protects from the polyalanine muscular dystrophy protein PABPNI. Hum Mol Genet. 17: 2108-2117.
Cerignoli F, et al. (2012) High throughput measurement of Ca2+ dynamics for drug risk assessment in human stem cell-derived cardiomyocytes by kinetic image cytometry. J Pharmacol Toxicol Methods. 66: 246-256.
Chambers SM, et al. (2009) Highly efficient neural conversion of human ES and iPS cells by dual inhibition of SMAD signaling. Nat Biotechnol. 27: 275-280.
Chandran S, et al. (1998) Regional potential for oligodendrocyte generation in the rodent embryonic spinal cord following exposure to EGF and FGF-2. Glia. 24: 382-389.
Chang JC, et al. (2001) Modulation of neural network activity by patterning. Biosens Bioelectron. 16: 527-533.
Charpentier A, et al. (1993) RRR-alpha-tocopheryl succinate inhibits proliferation and enhances secretion of transforming growth factor-beta (TGFbeta) by human breast cancer cells. Nutr Cancer. 19: 225-239.
Chaudhary KW, et al. (2006) Embryonic stem cells in predictive cardiotoxicity: laser capture microscopy enables assay development. Toxicol Sci. 90: 149-158.
Chaves M, et al. (2005) Robustness and fragility of Boolean models for genetic regulatory networks. J Theor Biol. 235: 431-449.
Chaves M, et al. (2006) Methods of robustness analysis for Boolean models of gene control networks. Syst Biol (Stevenage). 153: 154-167.

(56) References Cited

OTHER PUBLICATIONS

Chen CS, et al. (1997) Geometric control of cell life and death. Science. 276: 1425-1428.

Chen EW, et al. (1995) Target regulation of a motor neuron-specific epitope. J Neurosci. 15: 1555-1566.

Chen J and von Bartheld CS. (2004) Role of exogenous and endogenous trophic factors m the regulation of extraocular muscle strength during development.lnvest Ophthalmol Vis Sci. 45: 3538-3545.

Chen QS, et al. (2000) Impairment of hippocampal long-term potentiation by Alzheimer amyloid beta-peptides. J Neurosci Res. 60: 65-72.

Chen X, et al. (2005) Dedifferentiation of adult human myoblasts induced by ciliary neurotrophic factor in vitro. Moll Biol Cell. 16: 3140-3151.

Chen XF, et al. (2008) Dynamic simulation of the effect of calcium-release activated calcium channel on cytoplasmic Ca2+ oscillation. Biophys Chem. 136: 87-95.

Chen XP, (2003) [Exogenous rhCNTF inhibits myoblast differentiation of skeletal muscle of adult human in vitro]. Sheng Li Xue Bao. 55: 464-468.

Chiu A Y, et al. (1993) A motor neuron-specific epitope and the low-affinity nerve growth factor receptor display reciprocal patterns of expression during development, axotomy, and regeneration. J Comp Neurol. 328: 351-363.

Choi-Lundberg DL and Bohn MC. (1995) Ontogeny and distribution of glial cell line-derived neurotrophic factor (GDNF) mRNA in rat. Brain Res Dev Brain Res. 85: 80-88.

Choudhury A, et al. (2007) A piezoresistive microcantilever array for surface stress measurement: curvature model and fabrication. J Micromech Microeng. 17: 2065-2076.

Chow I and Poo MM. (1985) Release of acetylcholine from embryonic neurons upon contact with muscle cell. J Neurosci. 5: 1076-1082.

Christ B and Brand-Seberi B. (2002) Limb muscle development. Int J Dev Biol. 46: 905-914.

Cizkova D, et al. (2007) Functional recovery in rats with ischemic paraplegia after spinal grafting of human spinal stem cells. Neuroscience. 147: 546-560.

Clegg CH, et al. (1987) Growth factor control of skeletal muscle differentiation: commitment to terminal differentiation occurs in G 1 phase and is repressed by fibroblast growth factor. J Cell Biol. 105: 949-956.

Clements JD, et al. (1992) The time course of glutamate in the synaptic cleft. Science. 258: 1498-1501.

Coggan JS, et al. (2005) Evidence for ectopic neurotransmission at a neuronal synapse. Science. 309: 446-451.

Cohen RI and Almazan G. (1993) Norepinephrine-stimulated PI hydrolysis in oligodendrocytes is mediated by alpha IA-adrenoceptors. Neuroreport. 4: 1115-1118.

Cohen-Cory S. (2002) The developing synapse: construction and modulation of synaptic structures and circuits. Science. 298: 770-776.

Collins CA and Morgan JE. (2003) Duchenne's muscular dystrophy: animal models used to investigate pathogenesis and develop therapeutic strategies. Int J Exp Pathol. 84: 165-172.

Colomar A and Robitaille R. (2004) Glial modulation of synaptic transmission at the neuromuscular junction. Glia. 4 7: 284-289.

Cooper A, et al. (1976) The growth of mouse neuroblastoma cells in controlled orientations on thin films of silicon monoxide. Exp Cell Res. 103: 435-439.

Corey JM, et al. (1991) Compliance of hippocampal neurons to patterned substrate networks. J Neurosci Res. 30: 300-307.

Corey JM, et al. ( 1996) Micrometer resolution silane-based patterning of hippocampal neurons: critical variables in photoresist and laser ablation processes for substrate fabrication. IEEE Trans Biomed Eng. 43: 944-955.

Corey JM, et al. (1997) Differentiated B 104 neuroblastoma cells are a highresolution assay for micropatterned substrates. J Neurosci Methods. 75: 91-97.

Cortassa S, et al. (2003) An integrated model of cardiac mitochondrial energy metabolism and calcium dynamics. Biophys J. 84: 2734-2755.

Cossu G, et al. (1996) How is myogenesis initiated in the embryo? Trends Genet. 12: 218-223.

Courdier-Fruh I, et al. (2002) Glucocorticoid-mediated regulation of utrophin levels in human muscle fibers. Neuromuscul Disord. 12(Suppl 1): S95-S104.

Cross-Doersen D and Isfort RJ. (2003) A novel cell-based system for evaluating skeletal muscle cell hypertrophy-inducing agents. In Vitro Cell Dev Biol Animal. 39: 407-412.

Cukierman E, et al. (2002) Cell interactions with three-dimensional matrices. Curr Opin Cell Biol. 14: 633-639.

Cunningham JJ and Roussel MF. (2001) Cyclin-dependent kinase inhibitors in the development of the central nervous system. Cell Growth Differ. 12: 387-396.

Cuppini R, et al. (2001) Alpha-tocopherol controls cell proliferation in the adult rat dentate 12:vrus. Neurosci Lett. 303: 198-200.

Currie PD and Ingham PW. (1996) Induction of a specific muscle cell type by a hedgehog-like protein in zebrafish. Nature. 382: 452-455.

Curtis R, et al. (1988) Development of macroglial cells in rat cerebellum. I. Use of antibodies to follow early m VIVO development and migration of oligodendrocytes. J Neurocytol. 17: 43-54.

Cysyk J and Tung L. (2008) Electric field perturbations of spiral waves attached to millimeter-size obstacles. Biophys J. 94: 1533-1541.

Dakhel Y and Jamali F. (2006) Erythromycin potentiates PR interval prolonging effect of verapamil in the rat: a pharmacodynamic drug interaction. Toxicol Appl Pharmacol. 214: 24-29.

Daniels MP, et al. (2000) Rodent nerve-muscle cell culture system for studies of neuromuscular junction development: refinements and applications. Microsc Res Tech. 49: 26-37.

Daniels MP. (1990) Localization of actin, beta-spectrin, 43 × 10(3) Mr and 58 × 10(3) Mr proteins to receptor-enriched domains of newly formed acetylcholine receptor aggregates in isolated myotube membranes. J Cell Sci. 97(Pt 4): 615-626.

Daniels MP. (1997) Intercellular communication that mediates formation of the neuromusculariunction. Mol Neurobiol. 14: 143-170.

Das M, et al. (2003) Electrophysiological and morphological characterization of rat embryonic motoneurons in a defined system. Biotechnol Prog. 19: 1756-1761.

Das M, et al. (2004) Long-term culture of embryonic rat cardiomyocytes on an organosilane surface in a serum-free medium. Biomaterials. 25: 5643-5647.

Das M, et al. (2005) Adult rat spinal cord culture on an organosilane surface in a novel serum-free medium. In Vitro Cell Dev Biol Anim. 41: 343-348.

Das M, et al. (2006) A defined system to allow skeletal muscle differentiation and subsequent integration with silicon microstructures. Biomaterials. 27: 4374-4380.

Das M, et al. (2007a) Auto-catalytic ceria nanoparticles offer neuroprotection to adult rat spinal cord neurons. Biomaterials. 28: 1918-1925.

Das M, et al. (2007b) Differentiation of skeletal muscle and integration of myotubes with silicon microstructures using serum-free medium and a synthetic silane substrate. Nat Protoc. 2: 1795-1801.

Das M, et al. (2007c) Embryonic motoneuron-skeletal muscle co-culture in a defined system. Neuroscience. 146: 481-488.

Das M, et al. (2008) Temporal neurotransmitter conditioning restores the functional activity of adult spinal cord neurons in long-term culture. Exp Neurol. 209: 171-180.

Das M, et al. (2009a) Developing a novel serum-free cell culture model of skeletal muscle differentiation by systematically studying the role of different growth factors in myotube formation. In Vitro Cell Dev Biol Anim. 45: 378-387.

Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.

(56) References Cited

OTHER PUBLICATIONS

Das M, et al. (2010) A defined long-term in vitro tissue engineered model of neuromuscular junctions. Biomaterials. 31: 4880-4888.

Datar R, et al. (2009) Cantilever Sensors: Nanomechanical Tools for Diagnostics. MRS Bulletin. 34: 449-454.

David JA and Pitman RM. (1982) The effects of axotomy upon the extrasynaptic acetylcholine sensitivity of an identified motoneurone m the cockroach *Periplaneta americana*. J Exp Biol. 98: 329-341.

Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.

De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.

De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.

De Lange P, et al. (2006) Sequential changes in the signal transduction responses of skeletal muscle following food deprivation. FASEB J. 20: 2579-2581.

De Wilde J, et al. (2008) Short-term high fat-feeding results in morphological and metabolic adaptations m the skeletal muscle of C57BL/6J mice. Physiol Genomics. 32: 360-369.

Dell'Era P, et al. (2003) Fibroblast growth factor receptor-I is essential for in vitro cardiomyocyte development. Circ Res. 93: 414-420.

Denning C and Anderson D. (2008) Cardiomyocytes from human embryonic stem cells as predictors of cardiotoxicity. Drug Discovery Today: Therapeutic Strategies. 5: 223-232.

Dennis RG and Kosnik IPE. (2000) Excitability and isometric contractile properties of mammalian skeletal muscle constructs engineered in vitro. In Vitro Cell Dev Biol Anim. 36: 327-335.

Dennis RG, et al. (2001) Excitability and contractility of skeletal muscle engineered from primary cultures and cell lines. Am J Physiol Cell Physiol. 280: C288-C295.

Denyer MCT, et al. (1998) Preliminary study on the suitability of a pharmacological bio-assay based on cardiac myocytes cultured over microfabricated microelectrode arrays. Med Biol Eng Comput. 36: 638-644.

Descarries L, et al. (1997) Diffuse transmission by acetylcholine in the CNS. Prog Neurobiol. 53: 603-625.

Dhavan Rand Tsai L. (2001) A decade of CDK5. Nat Rev Mol Cell Biol. 2: 749-759.

Di Giovanni S, et al. (2005) Cell cycle inhibition provides neuroprotection and reduces glial proliferation and scar formation after traumatic brain injury. Proc Natl Acad Sci U SA. 102: 8333-8338.

Dimitrova DS and Gilbert DM. (2000) Temporally coordinated assembly and disassembly of replication factories in the absence of DNA synthesis. Nat Cell Biol. 2: 686-694.

Djouhri L and Lawson SN. (1999) Changes in somatic action potential shape in guinea-pig nociceptive primary afferent neurones during inflammation in vivo. J Physiol. 520 Pt 2: 565-576.

Dolcet X, et al. (2001) Cytokines promote motoneuron survival through the Janus kinase-dependent activation of the phosphatidylinositol 3-kinase pathway. Mol Cell Neurosci. 18: 619-631.

Du Y, et al. (2006) Distinct effects of p75 in mediating actions of neurotrophins on basal forebrain oligodendrocytes. Mol Cell Neurosci. 31: 366-375.

Dulcey CS, et al. (1991) Deep UV photochemistry of chemisorbed monolayers: patterned coplanar molecular assemblies. Science. 252: 551-554.

Dumont RJ, et al. (2001) Acute spinal cord injury, part I: pathophysiologic mechanisms. Clin Neuropharmacol12:v. 24: 254-264.

Duport S, et al. (1999) A metallic multisite recording system designed for continuous long-term monitoring of electrophysiological activity in slice cultures. Biosens Bioelectron. 14: 369-376.

Dusterhoft S and Pette D. (1999) Evidence that acidic fibroblast growth factor promotes maturation of rat satellite-cell-derived myotubes m vitro. Differentiation. 65: 161-169.

Dutton EK, et al. (1995) Acetylcholine receptor aggregation at nerve-muscle contacts in mammalian cultures: induction by ventral spinal cord neurons is specific to axons. J Neurosci. 15: 7401-7416.

Edwards D, et al. (2010) Addition of glutamate to serum-free culture promotes recovery of electrical activity in adult hippocampal neurons in vitro. J Neurosci Methods. 190: 155-163.

Egert U, et al. (1998) A novel organotypic long-term culture of the rat hippocampus on substrate-integrated multielectrode arrays. Brain Res Brain Res Protoc. 2: 229-242.

Egert U, et al. (2006) Analysis of cardiac myocyte activity dynamics with microeletrode arrays. In: Taketani M BM, editor. Advances in netwrok electrophysiology using multi electrode arrays: Springer 2006. p. 274-290.

Eisen A and Swash M. (2001) Clinical neurophysiology of ALS. Clin Neurophysiol. 112: 2190-2201.

Eisenberg T, et al. (2009) Induction of autophagy by spermidine promotes longevity. Nat Cell Biol. 11: 1305-1314.

Eldridge CF, et al. (1989) Differentiation of axon-related Schwann cells in vitro: II. Control of myelin formation by basal lamina. J Neurosci. 9: 625-638.

Elia D, et al. (2007) Sonic hedgehog promotes proliferation and differentiation of adult muscle cells: Involvement of MAPK/ERK and PI3K/Akt pathways. Biochim Biophys Acta. 1773: 1438-1446.

Emery AEH. (2002) The muscular dystrophies. Lancet. 359: 687-695.

Engler AJ, et al. (2006) Matrix elasticity directs stem cell lineage specification. Cell. 126: 677-689.

English AW. (2003) Cytokines, growth factors and sprouting at the neuromuscular junction. J Neurocytol. 32: 943-960.

Entcheva EK, et al. (2004) Fluorescence imaging of electrical activity in cardiac cells using an all-solid-state system. IEEE Trans Biomed Eng. 51: 331-341.

Ericson J, et al. (1992) Early stages of motor neuron differentiation revealed by expression ofhomeobox gene Islet-I. Science. 256: 1555-1560.

Esch MB, et al. (2011) The role of body-on-a-chip devices in drug and toxicity studies. Annu Rev Biomed Eng. 13: 55-72.

Esch MB, et al. (2012) On chip porous polymer membranes for integration of gastrointestinal tract epithelium with microfluidic 'body-on-a-chip' devices. Biomed Microdevices. 14: 895-906.

Eschenhagen T and Zimmermann WH. (2005) Engineering myocardial tissue. Circ Res. 97: 1220-1231.

Evans MS, et al. (1998) Electrophysiology of embryonic, adult and aged rat hippocampal neurons in serum-free culture. J Neurosci Methods. 79: 37-46.

Fan CM and Tessier-Lavigne M. (1994) Patterning of mammalian somites by surface ectoderm and notochord: evidence for sclerotome induction by a hedgehog homolog. Cell. 79: 1175-1186.

Faraut B, et al. (2004) Thrombin reduces MuSK and acetylcholine receptor expression along with neuromuscular contact size in vitro. Eur J Neurosci. 19: 2099-2108.

FDA (2004) Innovation or Stagnation: Challenge and Opportunity on the Critical Path to New Medical Products.

Fernandez-Valle C, et al. (1993) Expression of the protein zero myelin gene in axon-related Schwann cells is linked to basal lamina formation. Development. 119: 867-880.

Fernandez-Valle C, et al. (1995) Schwann cells degrade myelin and proliferate in the absence of macrophages: evidence from in vitro studies of Wallerian degeneration. J Neurocytol. 24: 667-679.

Fields GB, et al. (1998) Protein-like molecular architecture: biomaterial applications for inducing cellular receptor binding and signal transduction. Biopolymers. 47: 143-151.

Fields GB. (1999) Induction of protein-like molecular architecture by selfassembly processes. Bioorg Med Chem. 7: 75-81.

Figenschou A, et al. (1996) Cholinergic modulation of the action potential in rat hippocampal neurons. Eur J Neurosci. 8: 211-219.

Fink CC, et al. (1999) Determination of time-dependent inositol-1,4,5-trisphosphate concentrations during calcium release in a smooth muscle cell. Biophys J. 77: 617-628.

(56) References Cited

OTHER PUBLICATIONS

Fischbach GD and Cohen SA. (1973) The distribution of acetylcholine sensitivity over uninnervated and innervated muscle fibers grown in cell culture. Dev Biol. 31: 147-162.
Fischbach GD. (1972) Synapse formation between dissociated nerve and muscle cells in low density cell cultures. Dev Biol. 28: 407-429.
Fisher OZ, et al. (2010) Bioinspired materials for controlling stem cell fate. Ace Chem Res. 43: 419-428.
Fishman RA. (2002) The cerebrospinal fluid production rate is reduced in dementia of the Alzheimer's type. Neurology. 58: 1866; author reply 1866.
Flucher BE, et al. (1990) Localization of the alpha 1 and alpha 2 subunits of the dihydropyridine receptor and ankyrin in skeletal muscle triads. Neuron. 5: 339-351.
Flucher BE, et al. (1991) Biogenesis of transverse tubules in skeletal muscle in vitro. Dev Biol. 145: 77-90.
Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.
Flucher BE, et al. (1994) Molecular organization of transverse tubule/sarcoplasmic reticulum junctions during development of excitation-contraction coupling in skeletal muscle. Mol Biol Cell. 5: 1105-1118.
Forry SP, et al. (2006) Facilitating the culture of mammalian nerve cells with polyelectrolyte multilayers. Langmuir. 22: 5770-5775.
Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.
Fowler VM, et al. (1993) Tropomodulin is associated with the free (pointed) ends of the thin filaments in rat skeletal muscle. J Cell Biol. 120: 411-420.
Fox MA, et al. (2007) Distinct target-derived signals orgamze formation, maturation, and maintenance of motor nerve terminals. Cell. 129: 179-193.
Francis PT. (2008) Glutamatergic approaches to the treatment of cognitive and behavioural symptoms of Alzheimer's disease. Neurodegener Dis. 5: 241-243.
Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.
Franzini-Armstrong C and Protasi F. (1997) Ryanodine receptors of striated muscles: a complex channel capable of multiple interactions. Physiol Rev. 77: 699-729.
Friedman B, et al. (1995) BDNF and NT-4/5 exert neurotrophic influences on injured adult spinal motor neurons. J Neurosci. 15: 1044-1056.
Fu X, et al. (1995) Acidic fibroblast growth factor reduces rat skeletal muscle damage caused by ischemia and reperfusion. Chin Med J (Engl). 108: 209-214.
Fuentes-Medel Y, et al. (2012) Integration of a retrograde signal during synapse formation by glia-secreted TGF-B ligand. Curr Biol. 22: 1831-1838.
Funakoshi H, et al. (1995) Muscle-derived neurotrophin-4 as an activitydependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175: 50-57.
Galizia CG and Menzel R. (2000) Probing the olfactory code. Nat Neurosci. 3: 853-854.
Gao BX and Ziskind-Conhaim L. (1995) Development of glycine- and GABA-gated currents in rat spinal motoneurons. J Neurophysiol. 74: 113-121.

Gao Bx and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69: 4027-4037.
Gaud A, et al. (2004) Prednisone reduces muscle degeneration in dystrophindeficient Caenorhabditis elegans. Neuromuscul Disord. 14: 365-370.
Gaztanaga, L., Marchlinski, F. E., & Betensky, B. P. (2012). Mechanisms of cardiac arrhythmias. Revista Espanola de Cardiologfa (English Edition), 65(2), 174-185.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.
Ghiani CA, et al. (1999) Neurotransmitter receptor activation triggers p27(Kipl) and p21 ( CIP 1) accumulation and G 1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass L and Kauffman SA. (1973) The logical analysis of continuous, nonlinear biochemical control networks. J Theor Biol. 39: 103-129.
Glass L. ( 197 5) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF familyreceptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific. inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.

(56) References Cited

OTHER PUBLICATIONS

Greenstein JL and Winslow RL. (2002) An integrative model of the cardiac ventricular myocyte incorporating local control of Ca2+ release. Biophys J. 83: 2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374: 1745-1753.
Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNP1. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in APP+ PSI transgenic mice. Neurobiol Dis. 15: 188-195.
Haas HL and Selbach 0. (2000) Functions of neuronal adenosine receptors. Naunyn Schmiedebergs Arch Pharmacol. 362: 375-381.
Halbach M, et al. (2003) Estimation of action potential changes from field A402. potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.

Han DK and Hubbell JA. (1997) Synthesis of Polymer Network Scaffolds from 1-Lactide and Poly( ethylene glycol) and Their Interaction with Cells. Macromolecules. 30: 607-6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived A412. motoneurons in vitro and in motoneuron-injured adult rats. Proc Natl Acad Sci U s A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.
Henderson CE, et al. (1993) Neurotrophins promote motor neuron survival and are present in embryonic limb bud. Nature. 363: 266-270.
Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction-enhancement technique. J Appl Physiol. 82: 1739-1742.
Hennessey N, et al. (2001) Growth hormone administration and exercise effects on muscle fiber type and diameter in moderately frail older people. J Am Geriatr Soc. 49: 852-858.
Hermann M, et al. (2006) Exposure of atorvastatin is unchanged but lactone and acid metabolites are increased several-fold in patients withatorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.
Hickman J, et al. (1993) The use of monlayers as templates for biocompatibility studies. Abstracts of Papers of the American Chemical Society. 205: 146-Coll.
Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.
Hickman JJ, et al. (1994) Rational Pattern Design for in-Vitro Cellular Networks Using Surface Photochemistry. J Vac Science Technol A. 12: 607-616.
Hierlemann, Andreas, "CMOS-Based Bio/Chemosensor and Bioelectronic Microsystems," Procedia Chemistry, vol. 1, No. 1, Sep. 2009, pp. 5-8.
Hirano A. ( 1968) A confirmation of the oligodendroglial origin of myelin in the adult rat. J Cell Biol. 38: 637-640.
Hjerling-Leffler J, et al. (2005) The boundary cap: a source of neural crest stem cells that generate multiple sensory neuron subtypes. Development. 132: 2623-2632.
Hoffman EP and Escolar D. (2006) Translating mighty mice into neuromuscular therapeutics: is bigger muscle better? Am J Pathol. 168: 177 5-1778.
Hofmann F and Bading H. (2006) Long term recordings with microelectrode arrays: studies of transcription-dependent neuronal plasticity and axonal regeneration. J Physiol Paris. 99: 125-132.
Holleran AL, et al. (1995) Glutamine metabolism in AS-30D hepatoma cells. Evidence for its conversion into lipids via reductive carboxylation. Mol Cell Biochem. 152: 95-101.
Hondeghem LM and Hoffinan P. (2003b) Blinded test in isolated female rabbit heart reliably identifies action potential duration

(56) References Cited

OTHER PUBLICATIONS prolongation and proarrhythmic drugs: importance of triangulation, reverse use dependence, and instability. J Cardiovasc Pharmacol. 41: 14-24.
Hondeghem LM, et al. (2001) Instability and triangulation of the action potential predict serious proarrhythmia, but action potential duration prolongation is antiarrhythmic. Circulation. 103: 2004-2013.
Hondeghem LM, et al. (2003a) Detection of proarrhythmia in the female rabbit heart: blinded validation. J Cardiovasc Electrophysiol. 14: 287-294.
Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.
Hondeghem LM. (2007) Relative contributions of TRiaD and QT to proarrhythmia. J Cardiovasc Electrophysiol. 18: 655-657.
Hsiao CF, et al. (2005) Voltage-dependent calcium currents in trigeminal motoneurons of early postnatal rats: modulation by 5-HT receptors. J Neurophysiol. 94: 2063-2072.
Hu BY, et al. (2009) Human oligodendrocytes from embryonic stem cells: conserved SHH signaling networks and divergent FGF effects. Development. 136: 1443-1452.
Hua JY and Smth SJ. (2004) Neural activity and the dynamics of central nervous system development. Nat Neurosci. 7: 327-332.
Huang Y, et al. (2007) An alphaIA-adrenergic-extracellular signal-regulated kinase survival signaling pathway in cardiac myocytes. Circulation. 115: 763-772.
Huang YC, et al. (2005) Rapid formation of functional muscle in vitro using fibrin gels. J Appl Physiol. 98: 706-713.
Hucka M, et al. (2003) The systems biology markup language (SBML): a medium for representation and exchange of biochemical network models. Bioinformatics. 19: 524-531.
Hughes B. (2008) 2007 FDA drug approvals: a year of flux. Nat Rev Drug Discov. 7: 107-109.
Huh D, et al. (2010) Reconstituting organ-level lung functions on a chip. Science. 328: 1662-1668.
Huh D, et al. (2012) Microengineered physiological biomimicry: organs-onchips. Lab Chip. 12: 2156-2164.
Hui EE and Bhatia SN. (2007) Microscale control of cell contact and spacing via three-component surface patterning. Langmuir. 23: 4103-4107.
Hung SC, et al. (2002) In vitro differentiation of size-sieved stem cells into electrically active neural cells. Stem Cells. 20: 522-529.
Husmann I, et al. (1996) Growth factors in skeletal muscle regeneration. Cytokine Growth Factor Rev. 7: 249-258.
Huxley, A. F. (1975). The origin of force in skeletal muscle. Ciba Found Symp. 31: 271-290.
Ichikawa H, et al. (2004) Effect of Bm-3a deficiency on parvalbumin-immunoreactive primary sensory neurons in the dorsal root ganglion. Brain Res Dev Brain Res. 150: 41-45.
Inoue N, et al. (2004) Rapid electrical stimulation of contraction modulates gap junction protein m neonatal rat cultured cardiomyocytes: involvement of mi to gen-activated protein kinases and effects of angiotensin II-receptor antagonist. J Am Coll Cardiol. 44: 914-922.
Iravanian S, et al. (2003) Functional reentry in cultured monolayers of neonatal rat cardiac cells. Am J Physiol Heart Circ Physiol. 285: H449-H456.
Ito Y. (1999) Surface micropatterning to regulate cell functions. Biomaterials. 20: 2333-2342.
Izrael M, et al. (2007) Human oligodendrocytes derived from embryonic stem cells: Effect of noggin on phenotypic differentiation in vitro and on myelination in vivo. Mol Cell Neurosci. 34: 310-323.
Izumiya Y, et al. (2008) Fast/glycolytic muscle fiber growth reduces fat mass and improves metabolic parameters in obese mice. Cell Metabolism. 7: 159-172.
Jackson JH 4th, et al. (2004) Assessment of drug therapy management and the prevalence of heart failure in a managed care population with hypertension. J Manag Care Pharm. 10: 513-520.
Jaworska-Wilczynska M, et al. (2002) Three lipoprotein receptors and cholesterol in inclusion-body myositis muscle. Neurology. 58: 438-445.
Jensen J, et al. (2009) Human embryonic stem cell technologies and drug discovery. J Cell Physiol. 219: 513-519.
Jessen KR and Mirsky R. (2005) The origin and development of glial cells in peripheral nerves. Nat Rev Neurosci. 6: 671-682.
Jevsek M, et al. (2004) Origin of acetylcholinesterase in the neuromuscular junction formed in the in vitro innervated human muscle. Eur J Neurosci. 20: 2865-2871.
Jhamandas JH, et al. (2001) Cellular mechanisms for amyloid beta-protein activation of rat cholinergic basal forebrain neurons. J Neurophysiol. 86: 1312-1320.
Jiang XH, et al. (2009) Isolation and characterization of neural crest stem cells derived from in vitro-differentiated human embryonic stem cells. Stem Cells Dev. 18: 1059-1070.
Jiang Z and Clemens PR. (2006) Cellular caspase-8-like inhibitory protein ( cFLIP) prevents inhibition of muscle cell differentiation induced by cancer cells. F ASEB J. 20: 2570-2572.
Jiang ZG, et al. (1990) Excitatory and inhibitory transmission from dorsal root afferents to neonate rat motoneurons in vitro. Brain Res. 535: 110-118.
Jin P, et al. (1991) Recombinant platelet-derived growth factor-BB stimulates growth and inhibits differentiation of rat L6 myoblasts. J Biol Chem. 266: 1245-1249.
Johnson TE, et al. (2005) Statins and PP ARalpha agonists induce myotoxicity in differentiated rat skeletal muscle cultures but do not exhibit synergy with cotreatment. Toxicol Appl Pharmacol. 208: 210-221.
Julius D and Basbaum AI. (2001) Molecular mechanisms of nociception. Nature. 413: 203-210.
Jung DR, et al. (1998) Cell-Based Sensor Microelectrode Array Characterized by Imaging X-ray Photoelectron Spectroscopy, Scanning Electron Microscopy, Impedance Measurements, and Extracellular Recordings. Journal of Vacuum Science & Technology A (Vacuum, Surfaces, and Films). 16: 1183-1188.
Jung DR, et al. (2001) Topographical and physicochemical modification of material surface to enable patterning of living cells. Crit Rev Biotechnol. 21: 111-154.
Jurdana M, et al. (2009) Neural agrin changes the electrical properties of developing human skeletal muscle cells. Cell Mol Neurobiol. 29: 123-131.
Kaeberlein M. (2009) Spermidine surprise for a long life. Nat Cell Biol. 11: 1277-1278.
Kaji H, et al. (2003) Pharmacological characterization of micropatterned cardiac myocytes. Biomaterials. 24: 4239-4244.
Kamp TJ. (2009) Human pluripotent stem cell-derived cardiomyocytes for safety pharmacology applications. Journal of Pharmacological and Toxicological Methods. 60: 259.
Kane RS, et al. (1999) Patterning proteins and cells using soft lithography. Biomaterials. 20: 2363-2376.
Kang JH, et al. (2009) In vitro 3D model for human vascularized adipose tissue. Tissue Eng Part A. 15: 2227-2236.
Kato AC and Lindsay RM. (1994) Overlapping and additive effects of neurotrophins and CNTF on cultured human spinal cord neurons. Exp Neurol. 130: 196-201.
Katsuki H, et al. (2000) Distinct signaling pathways involved in multiple effects of basic fibroblast growth factor on cultured rat hippocampal neurons. Brain Res. 885: 240-250.
Katz LC and Shatz CJ. (1996) Synaptic activity and the construction of cortical circuits. 274: 1133-1138.
Kauffman S, et al. (2003) Random Boolean network models and the yeast transcriptional network. Proc Natl Acad Sci US A. 100: 14796-14799.
Kauffman S. (1971) Gene regulation networks: a theory for their global structure and behaviors. Curr Top Dev Biol. 6: 145-182.
Kaufmann P, et al. (2006) Toxicity of statins on rat skeletal muscle mitochondria. Cell Mol Life Sci. 63: 2415-2425.
Keefer EW, et al. (2001) Acute toxicity screening of novel AChE inhibitors using neuronal networks on microelectrode arrays. Neurotoxicology. 22: 3-12.

(56) References Cited

OTHER PUBLICATIONS

Keefer EW, et al. (2001) Characterization of acute neurotoxic effects of trimethylolpropane phosphate via neuronal network biosensors. Biosens Bioelectron. 16: 513-525.

Kessaris N, et al. (2008) Specification of CNS glia from neural stem cells in the embryonic neuroepithelium. Philos Trans R Soc Lond B Biol Sci. 363: 71-85.

Khademhosseini A, et al. (2006a) Interplay of biomaterials and microscale technologies for advancing biomedical applications. J Biomater Sci Polym Ed. 17: 1221-1240.

Khademhosseini A, et al. (2006b) Microscale technologies for tissue engineering and biology. Proc Natl Acad Sci USA. 103: 2480-2487.

Khorchid A, et al. (1999) Characterization of the signal transduction pathways mediating noradrenaline-stimulated MAPK activation and c-fos expression in oligodendrocyte progenitors. J Neurosci Res. 58: 765-778.

Khorchid A, et al. (2002) Developmental regulation of alpha 1A-adrenoceptor function in rat brain oligodendrocyte cultures. Neuropharmacolgv. 42: 685-696.

Kidambi S, et al. (2004) Controlling primary hepatocyte adhesion and spreading on protein-free polyelectrolyte multilayer films. J Am Chem Soc. 126: 16286-16287.

Kidambi S, et al. (2007a) Patterned co-culture of primary hepatocytes and fibroblasts using polyelectrolyte multilayer templates. Macromol Biosci. 7: 344-353.

Kidambi S, et al. (2007b) Cell adhesion on polyelectrolyte multilayer coated polydimethylsiloxane surfaces with varying topographies. Tissue Eng. 13: 2105-2117.

Kidd, J. (2006). Life after statin patent expires. Nat Rev Drug Discov. 5: 813-814.

Kim C, et al. (2010) Non-cardiomyocytes influence the electrophysiological maturation of human embryonic stem cell-derived cardiomyocytes during differentiation. Stem Cells Dev. 19: 783-795.

Kim D-H, et al. (2005) Modulation of adhesion and growth of cardiac myocytes by surface nanotopography. Proceedings fo the 2005 IEEE. Engineering in Medicine and Biology $27^{th}$ Annual Conference. Shanghai, China, Sep. 1-4, 2005.

Kim, Jinseok, et al. "Biohybrid microsystems actuated by cardiomyocytes: microcantilever, microrobot, and micropump." Robotics and Automation, 2008. ICRA 2008. IEEE International Conference on. IEEE, 2008.

Kim J, et al. (2002) Dopamine neurons derived from embryonic stem cells function in an animal model of Parkinson's disease. Nature. 418: 50-56.

Kim K, et al. (2011) Calibrated micropost arrays for biomechanical characterization of cardiomyocytes. Micro and Nano Letters. 6: 317-322.

Kim SU, et al. (2002) Production of immortalized human neural crest stem cells. Methods Mol Biol. 198: 55-65.

King T, et al. (2000) Piezoactuators for 'real-world' applications—Can they deliver sufficient displacement? Power Engineering. 14: 105-110.

Kingshott P and Griesser HJ. (1999) Surfaces that resist bioadhesion. Current Opinion in Solid State and Materials Science. 4: 403-412.

Kirazov E, et al. (2008) Amyloid beta peptides exhibit functional neurotoxicity to cortical network cultures. Compt Rend Acad Bulg Sci. 61: 905-910.

Kita-Matsuo H, et al. (2009) Lentiviral vectors and protocols for creation of stable hESC lines for fluorescent tracking and drug resistance selection of cardiomyocytes. PLoS One. 4: e5046.

Kleber AG and Rudy Y. (2004) Basic mechanisms of cardiac impulse propagation and associated arrhythmias. Physiol Rev. 84: 431-488.

Klein C, et al. (2002) Zinc inhibition of cAMP signaling. J Biol Chem. 277: 11859-11865.

Klein WL. (2002) Abeta toxicity in Alzheimer's disease: globular oligomers (ADDLs) as new vaccine and drug targets. Neurochem Int. 41: 345-352.

Kleinfeld D, et al. (1988) Controlled outgrowth of dissociated neurons on patterned substrates. J Neurosci. 8: 4098-4120.

Knobloch M and Mansuy IM. (2008) Dendritic spine loss and synaptic alterations in Alzheimer's disease. Mol Neurobiol. 37: 73-82.

Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.

Kobayashi T, et al. (1987) Human muscle cultured in monolayer and cocultured with fetal rat spinal cord: importance of dorsal root ganglia for achieving successful functional innervation. JNeurosci. 7: 3131-3141.

Koike T, et al. (2008) Axon & dendrite degeneration: its mechanisms and protective experimental paradigms. Neurochem Int. 52: 751-760.

Koirala S, et al. (2003) Roles of glial cells in the formation, function, and maintenance of the neuromuscular junction. J Neurocytol. 32: 987-1002.

Koleva M, et al. (2005) Pleiotropic effects of sonic hedgehog on muscle satellite cells. Cell Mol Life Sci. 62: 1863-1870.

Koliatsos VE, et al. (2008) Human stem cell grafts as therapies for motor neuron disease. Expert Opin Biol Ther. 8: 137-141.

Kontrogianni-Konstantopoulos A, et al. (2009) Muscle giants: molecular scaffolds in sarcomerogenesis. Physiol Rev. 89: 1217-1267.

Kornblum HI, et al. (1999) Multiple trophic actions of heparin-binding epidermal growth factor (HB-EGF) in the central nervous system. Eur J Neurosci. 11: 3236-3246.

Kucera J and Dorovini-Zis K. (1979). Types of human intrafusal muscle fibers. Muscle Nerve. 2: 437-451.

Kucera J and Walro J. (1992) Axotomy induces fusimotor-free muscle spindles in neonatal rats. Neurosci Lett. 136: 216-218.

Kucera J, et al. (1989) Role of nerve and muscle factors in the development of rat muscle spindles. Am J Anat. 186: 144-160.

Kucera J. (1982a) One-bag-fiber muscle spindles in tenuissimus muscles of the cat. Histochemistry and Cell Biologv. 76: 315-328.

Kucera, J. (1982b ). The topography of long nuclear chain intrafusal fibers in the cat muscle spindle. Histochemistry. 74: 183-197.

Kucera, J. (1983). Multiple-bag-fiber muscle spindles in tenuissimus muscles of the cat. Histochemistry. 79: 457-476.

Kudla AJ, et al. (1995) a requirement for fibroblast growth factor in regulation of skeletal muscle growth and differentiation cannot be replaced by activation of platelet-derived growth factor signaling pathways. Mol Cell Biol. 15: 3238-3246.

Kuhl U, et al. (1982) Synthesis of type IV collagen and laminin in cultures of skeletal muscle cells and their assembly on the surface of myotubes. Dev Biol. 93: 344-354.

Kuhl U, et al. (1986) Role of laminin and fibronectin in selecting myogenic versus fibrogenic cells from skeletal muscle cells in vitro. Dev Biol. 117: 628-635.

Kumar S, et al. (1998) NT-3-mediated TrkC receptor activation promotes proliferation and cell survival of rodent progenitor oligodendrocyte cells in vitro and in vivo. J Neurosci Res. 54: 754-765.

Kurek JB, et al. (1996) Leukemia inhibitory factor and interleukin-6 are produced by diseased and regenerating skeletal muscle. Muscle Nerve. 19: 1291-1301.

Lacor PN, et al. (2007) Abeta oligomer-induced aberrations m synapse A523. composition, shape, and density provide a molecular basis for loss of connectivity in Alzheimer's disease. J Neurosci. 27: 796-807.

Lacor PN. (2007) Advances on the understanding of the origins of synaptic pathology in AD. Curr Genomics. 8: 486-508.

Laflamme MA, et al. (2007) Cardiomyocytes derived from human embryonic stem cells in pro-survival factors enhance function of infarcted rat hearts. Nat Biotechnol. 25: 1015-1024.

Lamb TM, et al. (1993) Neural induction by the secreted polypeptide noggin. Science. 262: 713-718.

Lambert MP, et al. (1998) Diffusible, nonfibrillar ligands derived from Abetal-42 are potent central nervous system neurotoxins. Proc Natl Acad Sci US A. 95: 6448-6453.

(56) References Cited

OTHER PUBLICATIONS

Lambeth MJ and Kushmerick MJ. (2002) A computational model for glycogenolvsis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.
Langen RC, et al. (2003) Enhanced myogenic differentiation by extracellular matrix is regulated at the early stages of myogenesis. In Vitro Cell Dev Biol Anim. 39: 163-169.
Langer Rand Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proarrhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.
Lee HY, et al. (2004) Instructive role of Wnt/beta-catenin in sensory fate specification in neural crest stem cells. Science. 303: 1020-1023.
Lee MJ, et al. (2003) Hereditary sensory neuropathy is caused by a mutation in the delta subunit of the cytosolic chaperonin-containing t-complex peptide-1(Cct4) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation ofNMDA receptors by cyclin-dependent kinase-5. Proc Natl Acad Sci US A. 98: 12742-12747.
Li Land Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4:e312.
Li XJ, et al. (2005) Specification of motoneurons from human embryonic stem cells. Nat Boltechnol. 23: 215-221.

Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. CurrNeurovasc Res. 3: 281-288.
Lin JW, et al. (2008) Region [corrected] of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: SI 73-SI 79.
Liu CN, et al. (2000) Spinal nerve injury enhances subthreshold membrane potential oscillations m DRG neurons: relation to neuropathic pam. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci USA. 97: 6126-6131.
Liu TX, et al. (2006) Blinded validation of the isolated arterially perfused rabbit ventricular wedge in preclinical assessment of drug-induced proarrhythmias. Heart Rhythm. 3: 948-956.
Liu WP, et al. (2005) Enantioselectivity in environmental safety of current chiral insecticides. Proc Natl Acad Sci US A. 102: 701-706.
Lochter AJ, et al. (1995) Control of neuronal morphology in vitro: interplay between adhesive substrate forces and molecular instruction. J Neurosci Res. 42: 145-158.
Long C, et al. (2012) Design optimization of liquid-phase flow patterns for microfabricated lung on a chip. Ann Biomed Eng. 40: 1255-1267.
Lou XJ. (2009) Statistical switching kinetics of ferroelectrics. J Phys Condens Matter. 21(1):012207.
Lou XJ. (2009) Polarization fatigue in ferroelectric thin films and related materials. Journal of Applied Physics. 105: 024101-024124.
Love S. (2003) Neuronal expression of cell cycle-related proteins after brain ischaemia in man. Neurosci Lett. 353: 29-32.
Lu B, et al. (1996) Expression of synapsin I correlates with maturation of the neuromuscular synapse. Neuroscience. 74: 1087-1097.
Lu HR, et al. (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit IC.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Intl Dev Neurosci. 10: 59-73.
Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.
Machida S, et al. (2004) Primary rat muscle progenitor cells have decreased proliferation and myotube formation during passages. Cell Prolif. 37: 267-277.
Maduell F. (2005) Hemodiafiltration. Hemodial Int. 9: 47-55.

(56) References Cited

OTHER PUBLICATIONS

Mahler GJ, et al. (2009a) Characterization of a gastrointestinal tract microscale cell culture analog used to predict drug toxicity. Biotechnol Bioeng. 104: 193-205.
Mahler GJ, et al. (2009b) Characterization of Caco-2 and HT29-MTX cocultures in an in vitro digestion/cell culture model used to predict iron bioavailability. J Nutr Biochem. 20: 494-502.
Malerba A, et al. (2009) Selection of multipotent cells and enhanced muscle reconstruction by myogenic macrophage-secreted factors. Exp Cell Res. 315: 915-927.
Malm C, et al. (2004) Leukocytes, cytokines, growth factors and hormones in human skeletal muscle and blood after uphill or downhill running. J Physiol. 556: 983-1000.
Malo N, et al. (2006) Statistical practice in high-throughput screening data analysis. Nat Biotechnol. 24: 167-175.
Marhl M, et al. (2000) Complex calcium oscillations and the role of mitochondria and cytosolic proteins. Biosystems. 57: 75-86.
Marona HRN, et al. (1999) Determination of sparfloxacin and its degradation products by HPLC-PDA. J Antimicrob Chemother. 44: 301-302.
Marques MJ and Neto HS. (1997) Ciliary neurotrophic factor stimulates in vivo myotube formation in mice. Neurosci Lett. 234: 43-46.
Mars T, et al. (2001) Differentiation of glial cells and motor neurons during the A587. formation of neuromuscular junctions in cocultures of rat spinal cord explant and human muscle. J Comp Neurol. 438: 239-251.
Mars T, et al. (2003) Functional innervation of cultured human skeletal muscle proceeds by two modes with regard to agrin effects. Neuroscience. 118: 87-97.
Martin-Caraballo M and Greer JJ. (2000) Development of potassium conductances in perinatal rat phrenic motoneurons. J Neurophysiol. 83: 3497-3508.
Martinou JC, et al. (1992) Cholinergic differentiation factor (CDF/LIF) promotes survival of isolated rat embryonic motoneurons in vitro. Neuron. 8: 737-744.
Masu Y, et al. (1993) Disruption of the CNTF gene results in motor neuron degeneration. Nature. 365: 27-32.
Matsakas A and Patel K. (2009) Skeletal muscle fibre plasticity in response to selected environmental and physiological stimuli. Histol Histopathol. 24: 611-629.
Matsuda T, et al. (1992) Two-dimensional cell manipulation technology. An artificial neural circuit based on surface microphotoprocessing. ASAIO J. 38: M243-M247.
Matthews PB. (1964) Muscle spindles and their motor control. Physiol Rev. 44: 219-288.
Mattson MP, et al. (1992) Beta-Amyloid Peptides Destabilize Calcium Homeostasis and Render Human Cortical-Neurons Vulnerable to Excitotoxicity. J Neurosci. 12: 376-389.
Matzno S, et al. (2003) Evaluation of the synergistic adverse effects of concomitant therapy with statins and fibrates on rhabdomyolysis. J Pharm Pharmacol. 55: 795-802.
Maves L, et al. (2007) Pbx homeodomain proteins direct Myod activity to promote fast-muscle differentiation. Development. 134: 3371-3382.
Maynard EM. (2001) Visual prostheses. Annu Rev Biomed Eng. 3: 145-168.
McAuliffe GJ, et al. (2008) Development of a gastrointestinal tract microscale cell culture analog to predict drug transport. Mol Cell Biomech. 5: 119-132.
McBeath R, et al. (2004) Cell shape, cytoskeletal tension, and RhoA regulate stem cell lineage commitment. Dev Cell. 6: 483-495.
McDevitt TC, et al. (2002) In vitro generation of differentiated cardiac myofibers on micropatterned laminin surfaces. J Biomed Mater Res. 60: 472-479.
McMahon JA, et al. (1998) Noggin-mediated antagonism of BMP signaling is required for growth and patterning of the neural tube and somite. Genes Dev. 12: 1438-1452.
Megeney LA, et al. (1996) bFGF and LIF signaling activates STAT3 in proliferating myoblasts. Dev Genet. 19: 139-145.

Mehra S, et al. (2004) A boolean algorithm for reconstructing the structure of regulatory networks. Metab Eng. 6: 326-339.
Meijer L and Raymond E. (2003) Roscovitine and other purines as kinase inhibitors. From starfish oocytes to clinical trials. Ace Chem Res. 36: 417-425.
Melendez-Vasquez CV, et al. (2001) Nodes of Ranvier form in association with ezrin-radixin-moesin (ERM)-positive Schwann cell processes. Proc Natl Acad Sci US A. 98: 1235-1240.
Mendelsohn JD, et al. (2003) Rational design of cytophilic and cytophobic polyelectrolyte multilayer thin films. Biomacromolecules. 2003 4: 96-106.
Menendez L, et al. (2011) Wnt signaling and a Smad pathway blockade direct the differentiation of human pluripotent stem cells to multipotent neural crest cells. Proc Natl Acad Sci US A. 108: 19240-19245.
Menn B, et al. (2010) Delayed treatment with systemic (S)-roscovitine provides neuroprotection and inhibits in vivo CDK5 activity increase in animal stroke models. PLoS One. 5: e12117.
Metzger SW, et al. (1999) Development and characterization of surface chemistries for microfabricated biosensors. J of Vacuum Sci & Tech a—Vacuum Surfaces and Films. 17: 2623-2628.
Meyer G and Nabil MA. (1988) Novel optical approach to atomic force microscopy. Applied Physics Letters. 53: 1045-1047.
Meyer T, et al. (2004) Micro-electrode arrays in cardiac safety pharmacology—A novel tool to study QT interval prolongation. Drug Saf. 27: 763-772.
Meyer T, et al. (2004b) QT-screen: high-throughput cardiac safety pharmacology by extracellular electrophysiology on primary cardiac myocytes. Assay Drug Dev Technol. 2: 507-514.
Miles GB, et al. (2004) Functional properties of motoneurons derived from mouse embryonic stem cells. J Neurosci. 24: 7848-7858.
Miller FD. (2007) Riding the waves: neural and nonneural ongms for mesenchymal stem cells. Cell Stem Cell. 1: 129-130.
Miller SC, et al. (1988) Tumor necrosis factor inhibits human myogenesis in vitro. Mol Cell Biol. 8: 2295-2301.
Mitsumoto H, et al. (2001) Effects of cardiotrophin-1 (CT-1) in a mouse motor neuron disease. Muscle Nerve. 24: 769-777.
Mizuseki K, et al. (2003) Generation of neural crest-derived peripheral neurons and floor plate cells from mouse and primate embryonic stem cells. Proc Natl Acad Sci US A. 100: 5828-5833.
Moe GK. (1962) On the multiple wavelet hypothesis of atrial fibrillation. Arch Int Pharmacodyn Ther. 183-188.
Mohammed JS, et al. (2004) Micropatteming of nanoengineered surfaces to study neuronal cell attachment in vitro. Biomacromolecules. 5: 1745-1755.
Mohan DK, et al. (2006) Toxin detection based on action potential shape analysis using a realistic mathematical model of differentiated NG 108-15 cells. Biosens Bioelectron. 21: 1804-1811.
Mokry J, et al. (2007) Differentiation of neural stem cells into cells of oligodendroglial lineage. Acta Medica (Hradec Kralove). 50: 35-41.
Molnar P, et al. (2005) Biosurface Engineering. Encyclopedia of Medical Devices and Instrumentation. J.G. Webster. New York, John Wiley & Sons, Inc.
Molnar P, et al. (2007) Photolithographic Patterning of C2C12 Myotubes using Vitronectin as Growth Substrate in Serum-Free Medium. Biotechnol Prog. 23: 265-268.
Molnar P, et al. (2007b) Synaptic connectivity in engineered neuronal networks. Methods Mol Biol. 403: 165-173.
Molnar P, et al. (2007 c) Modeling of action potential generation in NG 108-15 cells. Methods Mol Biol. 403: 175-184.
Monaco EA 3rd and Vallano ML. (2005) Roscovitine triggers excitotoxicity in cultured granule neurons by enhancing glutamate release. Mol Pharmacol. 68: 1331-1342.
Monaco EA 3rd. (2004) Recent evidence regarding a role for Cdk5 dysregulation in Alzheimer's disease. Curr Alzheimer Res. 1: 33-38.
Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogemc differentiation. Development. 111: 7 41-7 48.

(56) References Cited

OTHER PUBLICATIONS

Morefield SI, et al. (2000) Drug evaluations using neuronal networks cultured on microelectrode arrays. Biosens Bioelectron. 15: 383-396.
Morganroth J and Gussak I. (2004) Cardiac Safety of Noncardiac Drugs: Practical Guidelines for Clinical Research and Drug Development. New York, Humana Press.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morimoto, S., & Masuda, M. (1984). Dependence of conduction velocity on spike interval during voluntary muscular contraction in human motor units. European journal of applied physiology and occupational physiology, 53(3), 191-195.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-I mediates the inhibition of endothelial cell proliferation and the promotion of skeletal myoblast differentiation by SPARC: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different In Vitro Systems Affect CYPIAI Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate C02/H+-sensitive neurons in rat brain stem slices. J Appl Physiol. 95: 910-921.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Muller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481: 617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan To Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash, M. P., & Panfilov, A. V. (2004). Electromechanical model of excitable tissue to study reentrant cardiac arrhythmias. Progress in biophysics and molecular biology, 85(2), 501-522.
Nash MP, et al. (2006) Evidence for multiple mechanisms in human ventricular fibrillation. Circulation. 114: 536-542.
Nat R. (2011) Cortical network from human embryonic stem cells. J Cell Mol Med. 15: 1429-1431.
Natarajan, Anupama et al., "Patterned cardiomyocytes on microelectrode arrays as a functional, high information content drug screening platform", Biomaterials 32, 2011, 4267-4274.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32: 4267-4274.
Natarajan A, et al. (2013) Engineered In Vitro Feed-Forward Networks. J Biotechnol Biomater. 3: 153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) Of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24: 1517-1530.
Nelson PG. (1975) Nerve and muscle cells in culture. Physiol Rev. 55: 1-61.
Nerbonne JM and Kass RS. (2005) Molecular physiology of cardiac repolarization. Physiol Rev. 85: 1205-1253.
Nguemo F, et al. (2012) In vitro model for assessing arrhythmogenic properties of drugs based on high-resolution impedance measurements. Cell Physiol Biochem. 29: 819-832.
Nguyen L, et al. (2006) The Yin and Yang of cell cycle progression and differentiation in the oligodendroglial lineage. Ment Retard Dev Disabil Res Rev. 12: 85-96.
Nicolelis MAL and Ribeiro S. (2002) Multielectrode recordings: the next steps. Curr Opin Neurobiol. 12: 602-606.
Nimmrich V, et al. (2008) Amyloid beta oligomers (A beta(I-42) globulomer) suppress spontaneous synaptic activity by inhibition of P/Q-type calcium currents. J Neurosci. 28: 788-797.
Nishikawa J, et al. (2005) Increase of Cardiotrophin-1 immunoreactivity in regenerating and overloaded but not denervated muscles of rats. Neuropathology. 25: 54-65.
Nishimaru H, et al. (2005) Mammalian motor neurons corelease glutamate and acetylcholine at central synapses. Proc Natl Acad Sci US A. 102: 5245-5249.
Nistor GI, et al. (2005) Human embryonic stem cells differentiate into oligodendrocytes in high purity and myelinate after spinal cord transplantation. Glia. 49: 385-396.
Noble D. (2004) Modeling the heart. Physiology (Bethesda). 19: 191-197.
Noll E and Miller RH. (1993) Oligodendrocyte precursors originate at the ventral ventricular zone dorsal to the ventral midline region in the embryonic rat spinal cord. Development. 118: 563-573.
Normann RA, et al. (1999) A neural interface for a cortical vision prosthesis. Vision Res. 39: 2577-2587.

(56) References Cited

OTHER PUBLICATIONS

Norris W, et al. (2000) Slow muscle induction by Hedgehog signalling in vitro. J Cell Sci. 113: 2695-2703.
Nugaeva, N, et al. (2005). Micromechanical cantilever array sensors for selective fungal immobilization and fast growth detection. Biosensors and Bioelectronics, 21(6), 849-856.
Nyitrai G, et al. (2006) Extracellular level of GABA and Glu: III VIVO microdialysis-HPLC measurements. Curr Top Med Chem. 6: 935-940.
Oakley RA, et al. (1997) Neurotrophin-3 promotes the differentiation of muscle spindle afferents in the absence of peripheral targets. J Neurosci. 17: 4262-4274.
O'Connor SM, et al. (2000) Immobilization of neural cells in three-dimensional matrices for biosensor applications. Biosens Bioelectron. 14: 871-881.
Offenhausser A and Knoll W. (2001) Cell-transistor hybrid systems and their potential applications. Trends Biotechnol. 19: 62-66.
Offenhausser A, et al. (1997) Field-effect transistor array for monitoring electrical activity from mammalian neurons m culture. Biosensors and Bioelectronics. 12: 819-826.
Oh TI, et al. (2007) Real-time fluorescence detection of multiple microscale cell culture analog devices in situ. Cytometry A. 71: 857-865.
Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.
Olson E. (1992a) Activation of muscle-specific transcription by myogenic helixloop-helix proteins. Symp Soc Exp Biol. 46: 331-341.
Olson EN and Perry WM. (1992b) MyoD and the paradoxes of myogenesis. Curr Biol. 2: 35-37.
Olson EN and Williams RS. (2000) Calcineurin Signaling and Muscle Remodeling. Cell. 101: 689-692.
Olson EN. (1992c) Interplay between proliferation and differentiation within the myogenic lineage. Dev Biol. 154: 261-272.
Olwin BB and Rapraeger A. (1992) Repression of myogenic differentiation by aFGF, bFGF, and K-FGF is dependent on cellular heparan sulfate. J Cell Biol. 118: 631-639.
Oppenheim RW, et al. (1991) Control of embryonic motoneuron survival in vivo by ciliary neurotrophic factor. Science. 251: 1616-1618.
Oppenheim RW, et al. (2001) Cardiotrophin-1, a muscle-derived cytokine, is required for the survival of subpopulations of developing motoneurons. J Neurosci. 21: 1283-1291.
Orentas DM and Miller RH. (1998) Regulation of oligodendrocyte development. Mol Neurobiol. 18: 247-259.
Orlov SN and Hamet P. (2006) Intracellular monovalent ions as second messengers. J Membr Biol. 210: 161-172.
Ostuni E, et al. (2000) Patterning mammalian cells using elastomeric membranes. Langmuir. 16: 7811-7819.
Oumata N, et al. (2008) Roscovitine-derived, dual-specificity inhibitors of cyclindependent kinases and casein kinases 1. J Med Chem. 51: 5229-5242.
Padmanabhan J, et al. (1999) Role of cell cycle regulatory proteins in cerebellar granule neuron apoptosis. J Neurosci. 19: 8747-8756.
Pagan SM, et al. (1996) Surgical removal of limb bud Sonic hedgehog results in posterior skeletal defects. Dev Biol. 180: 35-40.
Pancrazio JJ, et al. (1998) Portable cell-based biosensor system for toxin detection. Sensors and Actuators B Chem. 53: 179-185.
Park J, et al. (2005) Real-time measurement of the contractile forces of self-organized cardiomyocytes on hybrid biopolymer microcantilevers. Anal Chem. 77: 6571-6580.
Parker KK, et al. (2008) Myofibrillar architecture m engineered cardiac myocytes. Circ Res. 103: 340-342.
Park, TH et al. (2003) Integration of Cell Culture and Microfabrication Technology. Biotechnol. Prag. 19: 243-253.
Park, Hyun S. et al., "Neuromuscular Junction in a Microfluidic Device", Park et al., Neuromuscular Junction in a Microfluidic Device, 35th Annual International Conference of the IEEE EMBS, Osaka, Japan, 2833-2835, 2013, 2013, 2833-2835.
Pamg C, et al. (2002) Zebrafish: A Preclinical Model for Drug Screening. Assay Drug Dev Technol. 1:41-48.
Parviz M and Gross GW. (2007) Quantification of zinc toxicity using neuronal networks on microelectrode arrays. Neurotoxicolo12:v. 28: 520-531.
Paspalas CD and Papadopoulos GC. (1996) Ultrastructural relationships between noradrenergic nerve fibers and non-neuronal elements in the rat cerebral cortex. Glia. 17: 133-146.
Payne ET, et al. (2006) Nutritional therapy improves function and complements corticosteroid intervention in mdx mice. Muscle Nerve. 33: 66-77.
Peng HB, et al. (2003) Differential effects of neurotrophins and schwann cell-derived signals on neuronal survival/growth and synaptogenesis. J Neurosci. 23: 5050-5060.
Peroulakis ME and Forger NG. (2000) Ciliary neurotrophic factor increases muscle fiber number in the developing levator ani muscle of female rats. Neurosci Lett. 296: 73-76.
Perrier AL, et al. (2004) Derivation of midbrain dopamine neurons from human embryonic stem cells. Proc Natl Acad Sci US A. 101: 12543-12548.
Peters A. (1964) Observations on the Connexions Between Myelin Sheaths and Glial Cells in the Optic Nerves of Young Rats. J Anat. 98: 125-134.
Peterson CA, et al. (1999) Effects of moisture on Fowler-Nordheim characterization of thin silicon-oxide films. J Vac Science Technol A. 17: 2753-2758.
Pette D and Staron S. (2001) Transitions of muscle fiber phenotypic profiles. Histochem and Cell Biol. 115: 359-372.
Pette D, et al. (2002) Partial fast-to-slow conversion of regenerating rat fast-twithc muscle by chronic low frequency stimulation. J Muscle Res Cell Motil. 3: 215-221.
Pfeiffer SE, et al. (1993) The oligodendrocyte and its many cellular processes. Trends Cell Biol. 3: 191-197.
Pfrieger FW and Barres BA. (1997) Synaptic efficacy enhanced by glial cells in vitro. Science. 277: 1684-1687.
Pijnappels DA, et al. (2007) Resynchronization of separated rat cardiomyocyte fields with genetically modified human ventricular scar fibroblasts. Circulation. 116: 2018-2028.
Pillekamp F, et al. (2012) Contractile properties of early human embryonic stem cell-derived cardiomyocytes: beta-adrenergic stimulation induces positive chronotropy and lusitropy but not inotronv. Stem Cells Dev. 21: 2111-2121.
Podratz J, et al. (2004) Antioxidants are necessary for myelination of dorsal root ganglion neurons, in vitro. Glia. 45: 54-58.
Pomp O, et al. (2005) Generation of peripheral sensory and sympathetic neurons and neural crest cells from human embryonic stem cells. Stem Cells. 23: 923-930.
Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90: 1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.

(56) References Cited

OTHER PUBLICATIONS

Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and Mc Morris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B—Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K( +) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cellderived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly( ethylene glycol) Photolithography to Create High-Density Cell Arrays on Glass. Langmuir. 19: 9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.
Richert L, et al. (2004) pH dependent growth of poly(L-lysine )/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation m apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.

Rosenberg SS, et al. (2008) The geometric and spatial constraints of the microenvironment induce oligodendrocyte differentiation. Proc Natl Acad Sci U s A. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-I. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Saenz Cogollo et aL, "A Novel AFM-MEA Platform for Studying the Real Time Mechano-Electrical Behavior of Cardiac Myocytes," MRS Proceedings, vol. 1261, 2010, pp. 17-22.
Saenz, Jose F. et al., "A new integrated system combining atomic force microscopy and micro-electrode array for measuring the mechanical properties of living cardiac myocytes", Biomed Microdevices vol. 13, 2011, 613-621.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. ( 1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. JNeurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-641.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-119.
Scherer J, et al. (1995) Differentiation and maturation of rabbit retinal oligodendrocyte precursor cells in vitro. Brain Res Dev Brain Res. 89: 214-226.
Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter Hand Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276: C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.

(56) References Cited

OTHER PUBLICATIONS

Schuster Rand Holzhutter HG. (1995) Use of mathematical models for predicting the metabolic effect of large-scale enzyme activity alterations. Application to enzyme deficiencies ofred blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote Mand Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KA TP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S 1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12: 1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.
Sheridan DC, et al. (2003) Ca2+-dependent excitation-contraction coupling triggered by the heterologous cardiac/brain DHPR beta2a-subunit in skeletal myotubes. Biophys J. 85: 3739-3757.
Sheridan DC, et al. (2003) Truncation of the carboxyl terminus of the dihydropyridine receptor betala subunit promotes Ca2+ dependent excitation-contraction coupling in skeletal myotubes. Biophys J. 84: 220-237.
Sherman DL and Brophy PJ. (2005) Mechanisms of axon ensheathment and myelin growth. Nat Rev Neurosci. 6: 683-690.
Sherman DL, et al. (2005) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14: 1047.
Shin S, et al. (2005) Human motor neuron differentiation from human embryonic stem cells. Stem Cells Dev. 14: 266-269.
Shuker ML. (2012) Functional In Vitro System for Drug Discovery.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19: 317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith, et al., "A functional system for high-content screening of neuromuscular junctions in vitro", Smith et al., A functional system for high-content screening of neuromuscular junctions in vitro, Singap World Sci, vol. 1(1), pp. 37-48, 2013, 2013, 37-48.
Smith J and Schofield PN. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313: 107-117.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-1729.
Soundararajan P, et al. (2007) Easy and rapid differentiation of embryonic stem cells into functional motoneurons using sonic hedgehog-producing cells. Stem Cells. 25: 1697-1706.
Spach MS and Heidlage JF. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.
Spargo BJ, et al. (1994) Spatially controlled adhesion, spreading, and differentiation of endothelial cells on self-assembled molecular monolayers. Proc Natl Acad Sci USA. 91: 11070-11074.
Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.
St John PM, et al. (1997) Preferential glial cell attachment to microcontact printed surfaces. J Neurosci Methods. 75: 171-177.
St. George-Hyslop PH and Petit A. (2005) Molecular biology and genetics of Alzheimer's disease.CR Biol. 328: 119-130.
Stavarachi M, et al. (2010) Spinal muscular atrophy disease: a literature review for therapeutic strategies. J Med Life. 3: 3-9.

(56) References Cited

OTHER PUBLICATIONS

Steffen LS, et al. (2007) Zebrafish orthologs of human muscular dystrophy genes. BMC Genomics. 8: 79.
Stenger DA, et al. (1992) Coplanar Molecular Assemblies of Aminoalkylsilane and Perfluorinated Alkylsilane—Characterization and Geometric Definition of Mammalian-Cell Adhesion and Growth. Journal of the American Chemical Society. 114: 8435-8442.
Stenger DA, et al. (1993) Surface determinants of neuronal survival and growth on self-assembled monolayers in culture. Brain Res. 630: 136-147.
Stenger DA, et al. (1998) Microlithographic determination of axonal/dendritic polarity in cultured hippocampal neurons. J Neurosci Methods. 82: 167-173.
Sternberger NH, et al. (1985) Immunocytochemistry of myelin basic proteins in adult rat oligodendroglia. J Neuroimmunol. 7: 355-363.
Stett A, et al. (2003) Biological application of microelectrode arrays in drug discovery and basic research. Anal Bioanal Chem. 377: 486-495.
Stevens JL. (2006) Future of toxicology—mechanisms of toxicity and drug safety: where do we go from here? Chem Res Toxicol. 19: 1393-1401.
Stinstra J, et al. (2006) A Model of 3D Propagation in Discrete Cardiac Tissue. Comput Cardiol. 33: 41-44.
Stockwell BR. (2004) Exploring biology with small organic molecules. Nature. 432: 846-854.
Stoney GG. (1909) The Tension of Metallic Films Deposited by Electrolysis. Proc Roy Soc London. 82: 172-175.
Subramanian B, et al. (2010) Tissue-engineered three-dimensional in vitro models for normal and diseased kidney. Tissue Eng Part A. 16: 2821-2831.
Sun L, et al. (2007) JAK1-STAT1-STAT3, a key pathway promoting proliferation and preventing premature differentiation of myoblasts. J Cell Biol. 179: 129-138.
Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.
Sung JH and Shuler ML. (2009b) Prevention of air bubble formation in a microfluidic perfusion cell culture system using a microscale bubble trap. Biomed Microdevices. 11: 731-738.
Sung JH, et al. (2009c) Fluorescence optical detection in situ for real-time monitoring of cytochrome P450 enzymatic activity of liver cells in multiple microfluidic devices. Biotechnol Bioeng. 104: 516-525.
Sung JH, et al. (2010) A microfluidic device for a pharmacokinetic-pharmacodynamic (PK-PD) model on a chip. Lab Chip. 10: 446-455.
Sung JH, et al. (2013) Microfabricated mammalian organ systems and their integration into models of whole animals and humans. Lab Chip. 13: 1201-1212.
Suter W. (2006) Predictive value of in vitro safety studies. Curr Opin Chem Biol. 10: 362-366.
Sutton NM, et al. (2007) Clinical effects and outcome of feline permethrin spot-on poisonings reported to the Veterinary Poisons Information Service (VPIS), London. J Feline Med Surg. 9: 335-339.
Swasdison Sand Mayne R. (1992) Formation of highly organized skeletal muscle fibers in vitro. Comparison with muscle development in vivo. J Cell Sci. 102: 643-652.
Swynghedauw B. (1999) Molecular mechanisms of myocardial remodeling. Physiol Rev. 79: 215-262.
Takagishi Y, et al. (2000) Species-specific difference in distribution of voltage-gated L-type Ca(2+) channels of cardiac myocytes. Am J Physiol Cell Physiol. 279: C1963-C1969.
Takahashi T. (1978) Intracellular recording from visually identified motoneurons in rat spinal cord slices. Proc R Soc Lond B Biol Sci. 202: 417-421.
Takashima Y, et al. (2007) Neuroepithelial cells supply an initial transient wave of MSC differentiation. Cell. 129: 1377-1388.
Tan W and Desai TA. (2003) Microfluidic patterning of cells in extracellular matrix biopolymers: effects of channel size, cell type, and matrix composition on pattern integrity. Tissue Eng. 9: 255-267.
Tanaka M, et al. (2005) An Unbiased Cell Morphology Based Screen for New, Biologically Active Small Molecules. PLoS Biol. 3: e128.
Tanaka Y, et al. (2006) An actuated pump on-chip powered by cultured cardiomyocytes. Lab Chip. 6: 362-368.
Tarasenko YI, et al. (2007) Human fetal neural stem cells grafted into contusion-injured rat spinal cords improve behavior. JN eurosci Res. 85: 4 7-57.
Tatosian DA and Shuler ML. (2009) A novel system for evaluation of drug mixtures for potential efficacy in treating multidrug resistant cancers. Biotechnol Bioeng. 103: 187-198.
Termin A and Pette D. (1992) Changes in myosin heavy-chain isoform synthesis of chronically stimulated rat fast-twitch muscle. Eur J Biochem. 204: 569-573.
Terstappen GC, et al. (2007) Target deconvolution strategies in drug discovery. Nat. Rev Drug Discov. 6: 891-903.
Thomas CA, et al. (1972) A miniature microelectrode array to monitor the bioelectric activity of cultured cells. Exp Cell Res. 74: 61-66.
Thomas R. (1973) Boolean formalization of genetic control circuits. J Theor Biol. 1973. 42: 563-585.
Thompson PD, et al. (2006) An assessment of statin safety by muscle experts. Am J Cardiol. 97: 69C-76C.
Thompson RB, et al. (2005) Intracardiac transplantation of a mixed population of bone marrow cells improves both regional systolic contractility and diastolic relaxation. J Heart Lung Transplant. 24: 205-214.
Thorrez L, et al. (2008) Growth, differentiation, transplantation and survival of human skeletal myofibers on biodegradable scaffolds. Biomaterials. 29: 75-84.
Timmerman W and Westerink BH. (1997) Brain microdialysis of GABA and glutamate: what does it signify? Synapse. 27: 242-261.
Tobert JA. (2003) Lovastatin and beyond: the history of the HMGCoA reductase inhibitors. Nat Rev Drug Discov. 2: 517-526.
Toga T, et al. (2007) The 5-HT( 4) agonists cisapride, mosapride, and CJ-033466, a Novel potent compound, exhibit different human ether-a-go-go-related gene (hERG)-blocking activities. J Pharmacol Sci. 105: 207-210.
Tomb JF, et al. (1997) The complete genome sequence of the gastric pathogen Helicobacter pylori. Nature. 388: 539-547.
Torgan CE and Daniels MP. (2001) Regulation of myosin heavy chain expression during rat skeletal muscle development in vitro. Mol Biol Cell. 12: 1499-1508.
Torgan CE and Daniels MP. (2006) Calcineurin localization in skeletal muscle offers insights into potential new targets. J Histochem Cytochem. 54: 119-128.
Torimitsu Kand Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. F ASEB J. 19: 1592-1601.
Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.
Urakami H and Chiu A Y. (1990) A monoclonal antibody that recognizes somatic motor neurons in the mature rat nervous system. J Neurosci. 10: 620-630.

(56) References Cited

OTHER PUBLICATIONS

Urazaev AK, et al. (1995) Muscle NMDA receptors regulate the resting membrane potential through NO-synthase. Physiol Res. 44: 205-208.
Vakakis N, et al. (1995) In vitro myoblast to myotube transformations in the presence ofleukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
Van de Ven C, et al. (2007) The potential of umbilical cord blood multipotent stem cells for nonhematopoietic tissue and cell regeneration. Exp Hematol. 35: 1753-1765.
Van der Valk J, et al. (2010) Optimization of chemically defined cell culture media—replacing fetal bovine serum in mammalian in vitro methods. Toxicol In Vitro. 24: 1053-1063.
Van Rijen HV, et al. (2006) Connexins and cardiac arrhythmias. Adv Cardiol. 42: 150-160.
Van Soest PF and Kits KS. (1998) Conopressin affects excitability, firing, and action potential shape through stimulation of transient and persistent inward currents in mulluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue culture: Effects on skeletal muscle organogenesis. In Vitro Cell Dev Biol. 24: 609-619.
Varghese K, et al. (2009) Regeneration and characterization of adult mouse hippocampal neurons in a defined in vitro system. J Neurosci Methods. 177: 51-59.
Varghese K, et al. (2010) A new target for amyloid beta toxicity validated by standard and high-throughput electrophysiologv. PLoS One. 5: e8643.
Vargo TG, et al. (1992) Monolayer Chemical Lithography and Characterization of Fluoropolymer Films. Langmuir. 8: 130-134.
Vartanian T, et al. (1988) Oligodendrocyte substratum adhesion modulates expression of adenylate cyclase-linked receptors. Proc Natl Acad Sci USA. 85: 939-943.
Ventimiglia R, et a. (1987) Localization of beta-adrenergic receptors on differentiated cells of the central nervous system in culture. Proc Natl Acad Sci U s A. 84: 5073-5077.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-LI cells to mimic bioaccumulation in a microscale cell culture analog device for toxicity studies. Biotechnol Prog. 20: 590-597.
Vogel V and Sheetz M. (2006) Local force and geometry sensing regulate cell functions. Nat Rev Mol Cell Biol. 7: 265-275.
Vogel Zand Daniels MP. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.
Waggoner PS and Craighead HG. (2007) Micro- and nanomechanical sensors for environmental, chemical, and biological detection. Lab Chip. 7: 1238-1255.

Wagner I, et al. (2013) A dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.
Walsh DM and Selkoe DJ. (2007) A beta oligomers—a decade of discovery. J Neurochem. 101: 1172-1184.
Walsh K, et al. (2005) Human central nervous system tissue culture: a historical review and examination ofrecent advances. Neurobiol Dis. 18: 2-18.
Wang HW, et al. (2002) Soluble oligomers of beta amyloid (1-42) inhibit long-term potentiation but not long-term depression in rat dentate gyrus. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and ciliary neurotrophic factor on the proliferation and differentiation of adult human myoblasts. Cell Mol Neurobiol. 28: 113-124.
Ward JH, et al. (2001) Micropatteming of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1 alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson, Kerry et al., "Measurement of Contractile Stress Generated by Cultured Rat Muscle on Silicon Cantilevers for Toxin Detection and Muscle Performance Enhancement", Wilson et al., Measurement of Contractile Stress Generated by Cultured Rat Muscle on Silicon Cantilevers for Toxin Detection and Muscle Performance Enhancement, Plos one vol. 5(6), pp. 1-11, 2010, 2010, 1-11.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122: R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation ofmyelination by Schwann cells. Ann NY Acad Sci. 605: 1-14.
Wright CD, et al. (2008) Nuclear alphal-adrenergic receptors signal activated ERK localization to caveolae in adult cardiac myocytes. Circ Res. 103: 992-1000.

(56) References Cited

OTHER PUBLICATIONS

Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity m functional mammalian neuronal networks grown on patterned surfaces. J Neurosci Methods. 117: 123-131.
Xi J, et al. (2005) Self-assembled microdevices driven by muscle. Nat Mater. 4: 180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-I transgenic rats. Transplantation. 82: 865-875.
Xu T, et al. (2004) Construction of high-density bacterial colony arrays and patterns by the ink-jet method. Biotechnol Bioeng. 85: 29-33.
Xu T, et al. (2005) Inkjet printing of viable mammalian cells. Biomaterials. 26: 93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.
Yan J, et al. (2007) Extensive neuronal differentiation of human neural stem cell grafts in adult rat spinal cord. PLoS Med. 4: 318-332.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly( diol citrate) biodegradable elastomers. Biomaterials. 27: 1889-1898.
Yang L, et al. (2007) Increased asynchronous release and aberrant calcium channel activation m amyloid precursor protein deficient neuromuscular synapses. Neuroscience. 149: 768-778.
Yang LX and Nelson PG. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatteming capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.
Yap FL and Zhang Y. (2007) Protein and cell micropatteming and its integration with micro/nanoparticles assembly. Biosens Bioelectron. 22: 775-788.
Yasuda SI, et al. (2001) A novel method to study contraction characteristics of a single cardiac myocyte using carbon fibers. Am J Physiol Heart Circ Physiol. 281: H1442-H1446.
Yeung CK, et al. (2007) Drug profiling using planar microelectrode arrays. Anal Bioanal Chem. 387: 2673-2680.
Yin SH, et al. (2005) Measuring single cardiac myocyte contractile force via moving a magnetic bead. Biophys J. 88: 1489-1495.
Zhao BL, et al. (1989) Scavenging effect of extracts of green tea and natural antioxidants on active oxygen radicals. Cell Biophys. 14: 175-185.
Zhou L, et al. (2005) Mechanistic model of cardiac energy metabolism predicts localization of glycolysis to cytosolic subdomain during ischemia. Am J Physiol Heart Circ Physiol. 288: H2400-H2411.
Zhou Z, et al. (1999) Block of HERG potassium channels by the antihistamine astemizole and its metabolites desmethylastemizole and norastemizole. J Cardiovasc Electrophysiol. 10: 836-843.
Zimmermann WH, et al. (2000) Three-dimensional engineered heart tissue from neonatal rat cardiac myocytes. Biotechnol Bioeng. 68: 106-114.
Zimmermann WH, et al. (2002) Tissue Engineering of a Differentiated Cardiac Muscle Construct. Circ Res. 90: 223-230.
Zorzano A, et al. (2003) Intracellular signals involved in the effects of insulin-like growth factors and neuregulins on myofibre formation. Cell Signal. 15: 141-149.
Zurn AD, et al. (1996) Combined effects of GDNF, BDNF, and CNTF on motoneuron differentiation in vitro. J Neurosci Res. 44: 133-141.
Zweigerdt R, et al. (2003) Generation of confluent cardiomyocyte monolayers derived from embryonic stem cells in suspension: a cell source for new therapies and screening strategies. Cytotherapy. 5: 399-413.

\* cited by examiner

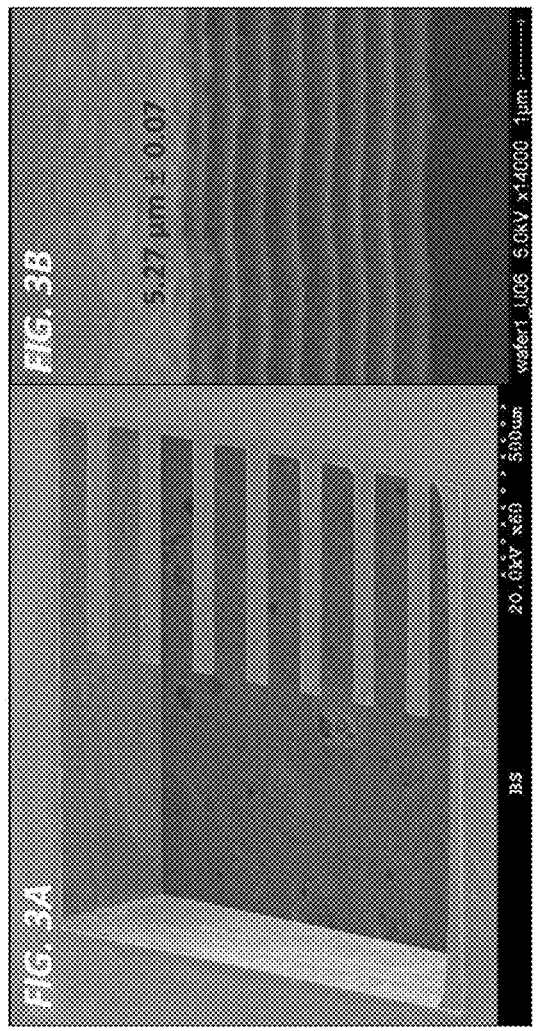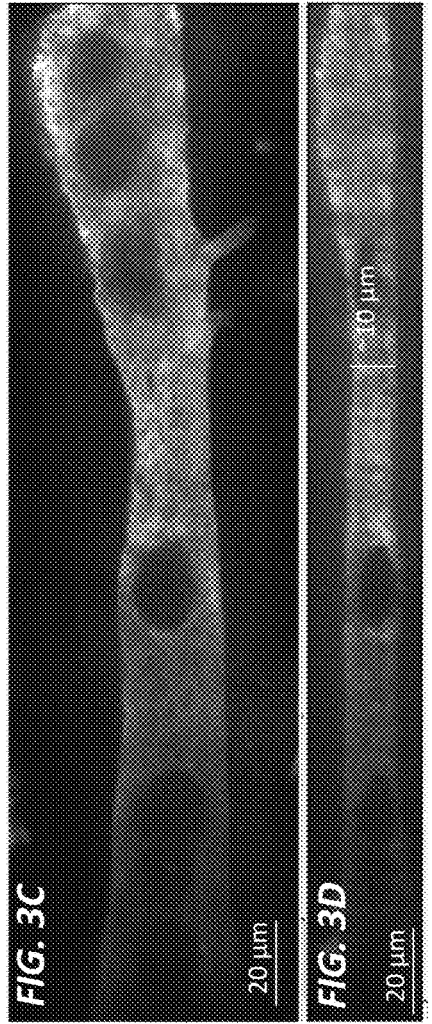
FIG. 3A  FIG. 3B  FIG. 3C  FIG. 3D

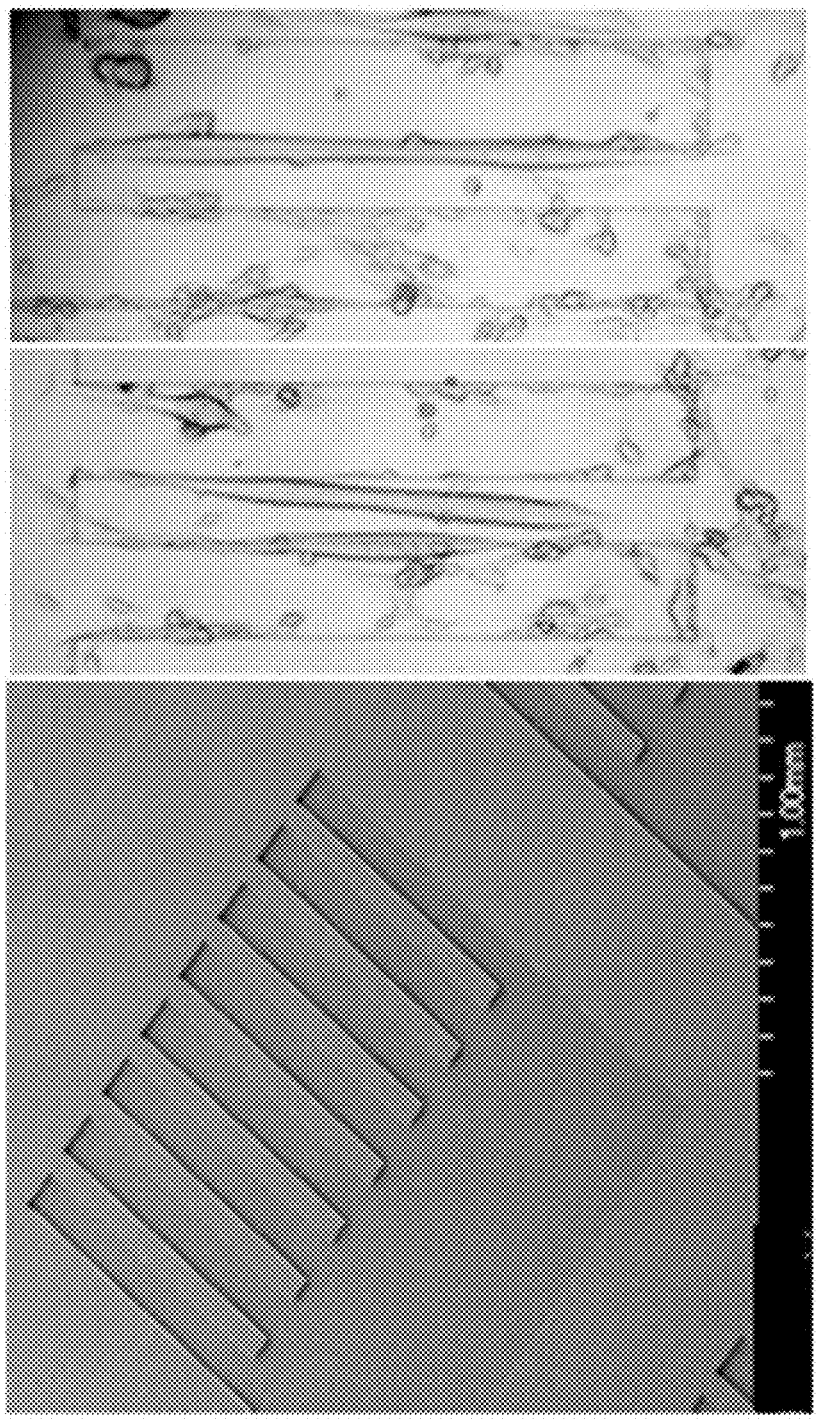

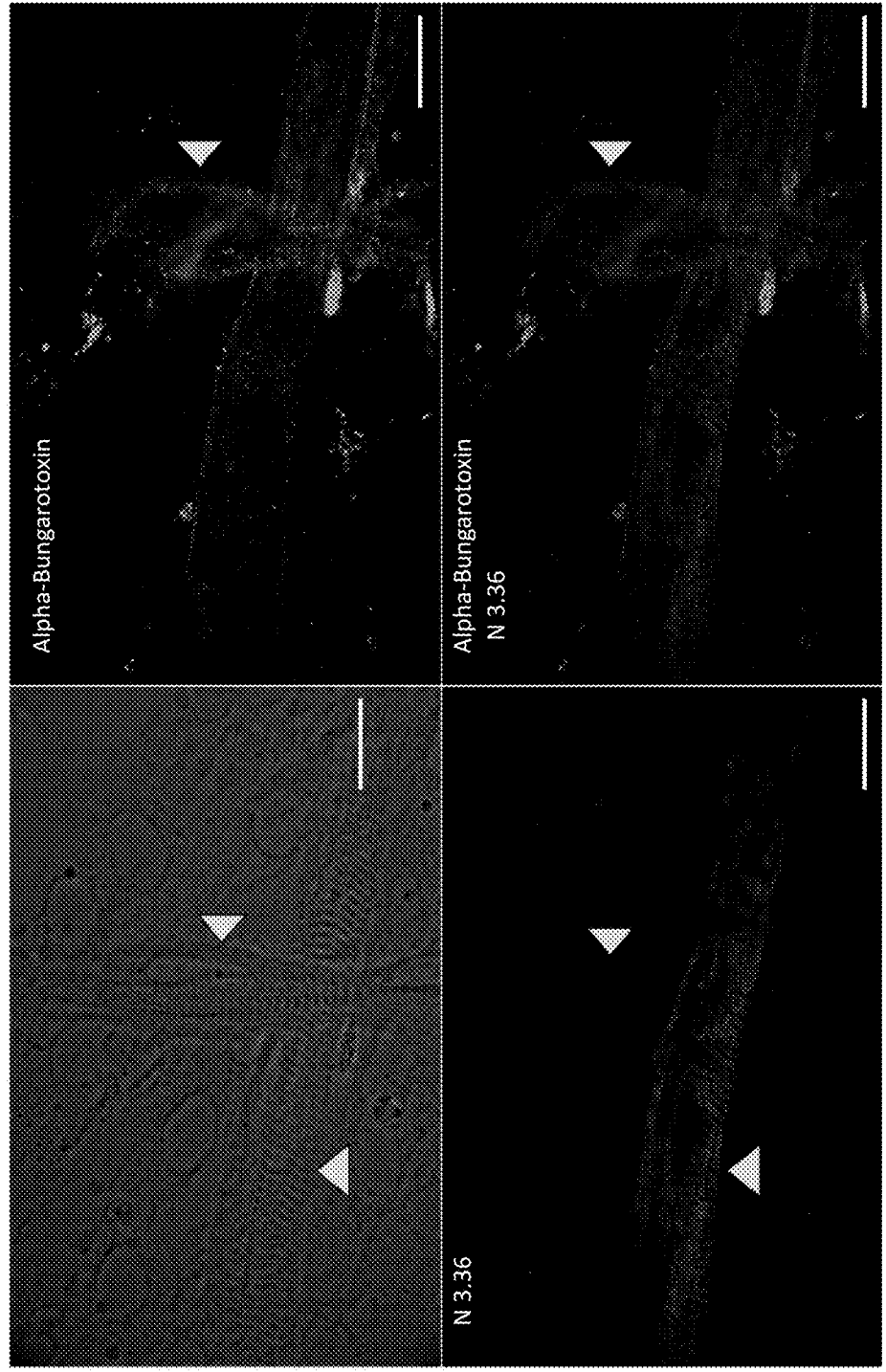

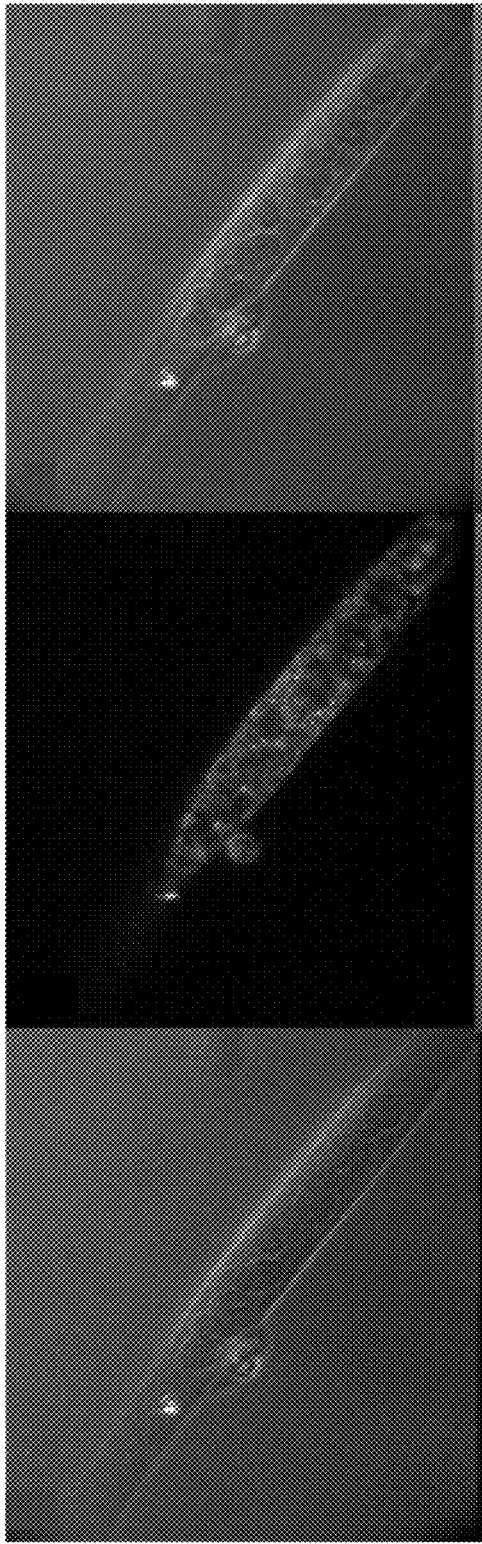
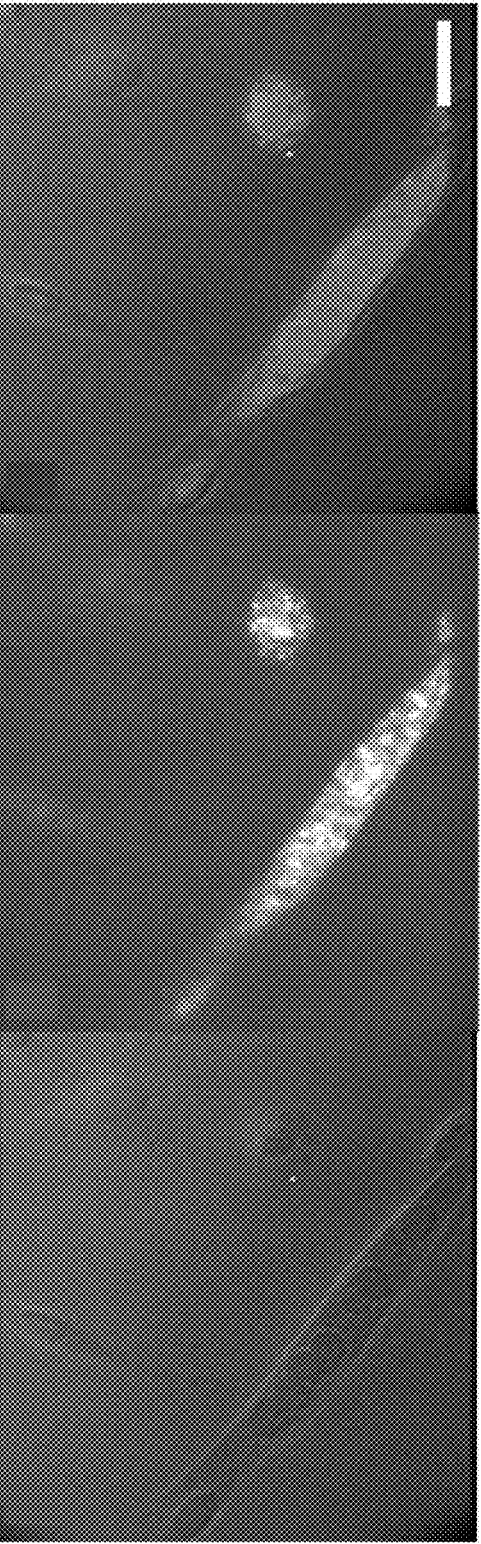
FIG. 13A  FIG. 13B  FIG. 13C  FIG. 13D  FIG. 13E  FIG. 13F

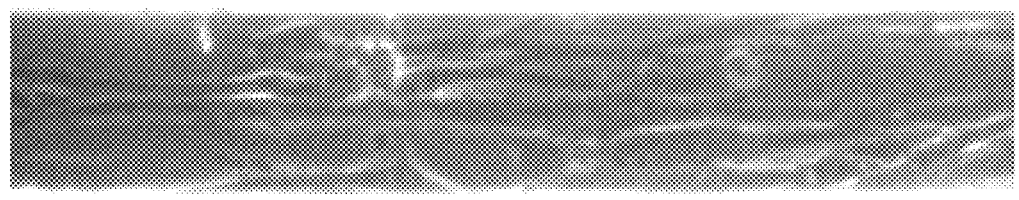
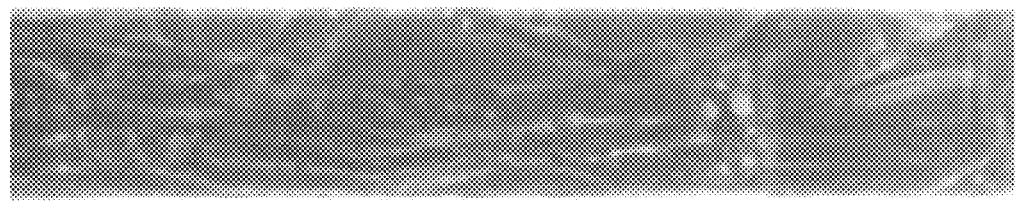
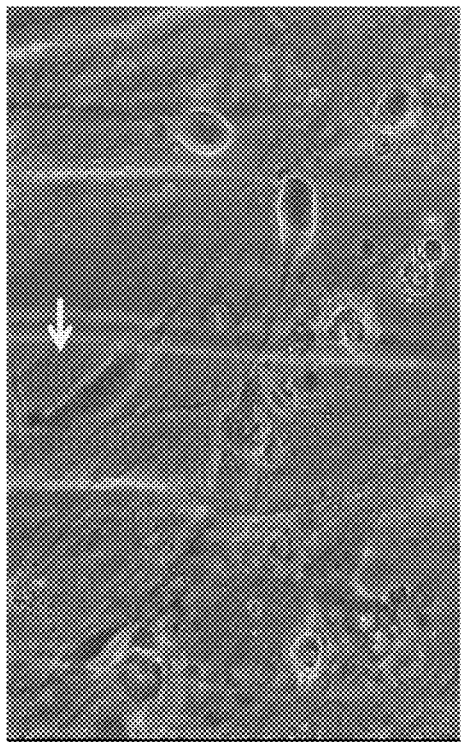
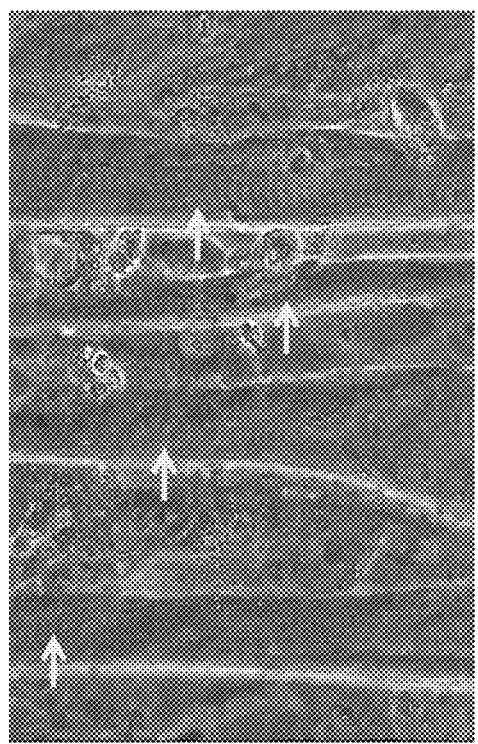

BIO-MICROELECTROMECHANICAL SYSTEM TRANSDUCER AND ASSOCIATED METHODS

RELATED APPLICATIONS

This application is a continuation of U.S. Ser. No. 12/661,323, which was filed on 15 Mar. 2010, which claims priority from provisional applications Ser. No. 61/159,851 which was filed on 13 Mar. 2009, and Ser. No. 61/259,715, which was filed on 10 Nov. 2009, the disclosures of which are incorporated herein by reference in their entirety.

STATEMENT OF GOVERNMENT RIGHTS

This invention was made with Government support under agency contract/grant no. R01 NS050452 awarded by the National Institutes of Health. The government has certain rights in this invention.

FIELD OF THE INVENTION

The present invention relates to the field of muscle physiology and, more particularly, to a bio-microelectromechanical system (MEMS) useful as a transducer in testing drugs and actuating muscle tissue.

BACKGROUND OF THE INVENTION

Microelectromechanical systems (MEMS) have received a great deal of attention in recent years due to their promise for miniaturizing systems for a variety of applications. One particularly interesting facet of MEMS technologies is the possibility of coupling solid state devices with biological components (Bio-MEMS) such as biomolecules, cells, and tissues for creating novel bioanalytical systems.

Bio-MEMS technologies present a unique opportunity to study fundamental biological processes at a level unrealized with previous methods. The capability to miniaturize analytical systems enables researchers to perform multiple experiments in parallel and with a high degree of control over experimental variables. This capacity allows a high throughput approach for studying a wide variety of problems in biology.

Skeletal muscles are highly differentiated organs whose primary function is to generate longitudinal force for locomotion. Anatomically, myotubes or myofibers are composed of densely packed proteins (myofibrils), mostly myosin and actin, organized into functional structures called sarcomeres. During force generation the distance between the interconnected sarcomeres decreases as myosin pulls on the actin filaments. The process is mediated by $Ca^{2+}$ release from the sarcoplasmic reticulum and is known as the sliding filament theory of muscular contraction (Huxley 1975; Gordon et al. 2000). Adult skeletal muscle is composed of two distinct types of fibers, extrafusal and intrafusal. The extrafusal fibers are part of the force generating motor circuit while the intrafusal fibers form the muscle component of a stretch sensor. Extrafusal and intrafusal fibers differ morphologically, functionally, and by their neuronal innervation.

The general structure of the sarcomere is consistent among extrafusal muscle fibers. However, adult skeletal muscle expresses multiple isoforms of myosin heavy chain (MHC) protein. Each isoform exhibits distinct ATPase activity that alters the physiological properties of the sarcomere and the myofiber overall. MHC classes can be divided into three isoforms type I, type IIa, and type IIb (Walro and Kucera 1999).

Type I muscle fibers contact slowly relative to the other isoforms due to slow ATPase activity and are slow to fatigue due to high levels of mitochondrial enzymes that generate large amounts of ATP. They contain a large number of mitochondria and myoglobin which give them a distinctive red color and are, therefore, known as red fibers. These fibers rely on aerobic respiration for ATP regeneration and are responsible for sustained, tonic contraction. They typically maintain an intracellular calcium level above 100 nM, but below 300 nM (Olson and Williams 2000; Scott et al. 2001). In vivo evidence suggests that chronic long term stimulation of fast twitch muscle fibers like the tibialis anterior causes a switch to the slow MHC isoform (Termin and Pette 1992; Pette et al. 2002). The integral membrane protein phospholamban is expressed exclusively in type I fibers where it regulates the $Ca^{2+}$ pump adding an additional level of contractile rate control (Pette and Staron 2001).

Type IIa myofibers can be considered an intermediate between fast and slow twitch fibers. These muscle fiber types also contain a high number of large mitochondria as well as increased myoglobin levels, which also gives them a red appearance. However, they are able to split ATP rapidly which gives the myotubes a high contractile velocity. They are resistant to fatigue because of their high capacity to regenerate ATP by oxidation, but not as resistant as Type I fibers (Scott et al. 2001). The $Ca^{2+}$ binding protein parvalbumin is expressed exclusively in Type II fibers where it aids in muscle relaxation by removing $Ca^2$30 from the cytoplasm of the myofiber (Pette and Staron 2001).

Type IIb fibers are known as white fibers due to their low levels of mitochondria and myoglobin. They also possess few blood capillaries and consequently rely on anaerobic respiration for ATP regeneration. Type IIb fibers contain a large amount of glycogen and split ATP very rapidly. These factors leave these muscle fibers prone to fatigue. Fast twitch glycolytic fibers (type IIb) are used for sudden bursts of contraction and are characterized by brief, high-amplitude $Ca^{2+}$ transients and lower ambient $Ca^{2+}$ levels (<50 nM) (Olson and Williams 2000; Scott et al. 2001). It has been previously determined that the increased thyroxine (T4) and triiodothyronine (T3) levels in hyperthyroid animal models results in a conversion to type II fibers while hypothyroidism results in conversions in the opposite direction (Caiozzo et al. 1992). In vivo data has also established that calcineurin will de-phosphorylate Nuclear Factor of Activated T-cells (NFATs) which will allow them to translocate from the cytosol to the nucleus. Once in the nucleus, they bind to promoters and enhancers that activate slow fiber type formation (Schiaffino and Serrano 2002). Cyclosporin is an inhibitor of the calcineurin signaling pathway (Schneider et al. 1999). Akt 1 induces type IIb fiber formation and can be activated by platelet derived growth factor (PDGF) (Izumiya et al. 2008).

Intrafusal fibers reside in specialized sensory structures called muscle spindles. Morphologically, muscle spindles consist of two to twelve intrafusal fibers that are distinct from the extrafusal fibers in both structure and function. These unique fibers can be categorized morphologically as nuclear bag1, nuclear bag2 and nuclear chain fibers based on the location of their nuclei (Matthews 1964; Kucera 1982b). In nuclear bag fibers, the nuclei are clustered in an enlarged central region, while in nuclear chain fibers, the nuclei are arranged in a single row localized in the equatorial region (Kucera 1982a; Kucera 1983). The spindle fibers are also unique in that morphological characteristics such as striation and myofibril density vary proportionately with distance from the center (Kucera and Dorovini-Zis 1979). In fact, they are heavily striated at their polar regions indicating the presence of contractile sarcomeric units, a feature that decreases moving equatorially until it is nearly absent. This feature plays an important role in the sensitivity to stretch seen in fibers and consequently the nerve terminals that innervate them. Due to their unique role in sensory perception, these fibers express a distinct protein called α cardiac-like MHC at their equatorial region.

One tissue of particular interest with respect to a variety of diseases is skeletal muscle. Diseases affect skeletal muscle in different ways. Some diseases, such as amyotrophic lateral sclerosis (ALS), affect the stimulating inputs from the neuromuscular junction. Other diseases affect the muscle directly such as muscular dystrophy and muscular atrophy, which cause deterioration of the muscles' ability to generate force. Thus, it is advantageous to have a system that allows the real-time interrogation of the physiological properties of muscle as well as the controlled addition of exogenous factors for comparative experimentation. However, it is first necessary to be able to apply the measurements to statistical analysis with regard to physiological factors such as peak stress generated, time to peak stress, the time needed for the muscle to relax to half of the peak stress, and the average rate of stress generation. All of these factors give information about the condition of the muscle and can be compared to published values.

The present study outlines a novel method for performing real-time quantitative measurements of the physiological properties of cultured skeletal muscle using a Bio-MEMS device. Stresses generated by myotubes were measured using a modified Stoney's equation, which quantifies stresses generated by a thin film on a microcantilever with known physical properties. By this method it has been shown that it is possible to quantitatively measure stress on microcantilevers that are in agreement with values previously published in the literature for cultured skeletal muscle. Furthermore, a method for selectively seeding and coculturing neuronal and muscle cells on these devices using microfluidic chambers was developed. By this method it was possible to create a model for studying neuromuscular junction development and function. This work validates the use of this system as a foundation for a high-throughput Bio-MEMS device.

SUMMARY OF THE INVENTION

With the foregoing in mind, the present invention advantageously provides a bio-MEMS transducer comprising a cultured myotube and a piezoelectric microcantilever having the myotube attached thereto along a lengthwise extent of said microcantilever.

In the invention, the bio-MEMS transducer may also further comprise an input/output processor operably connected with said piezoelectric microcantilever to process electrical signals received therefrom and to send electrical signals thereto. Optionally, the bio-MEMS transducer may also further include an optical sensor positioned to sense microcantilever deflection. The optical sensor preferably includes a laser aimed to reflect from said microcantilever and a photodetector positioned to detect a change in reflection angle of said laser.

The presently disclosed bio-MEMS transducer functions as a biosensor wherein the attached myotube contracts on contact with a sensed agent, the myotube contraction deflecting the microcantilever to generate a piezoelectric signal therefrom. In this embodiment, the sensed agent may be selected, without limitation, from metabolic inhibitors, nutritional supplements, therapeutic compounds or compositions, investigational drugs, and combinations thereof. For example, the disclosed bio-MEMS sensor may be used to investigate the effectiveness on muscle tissue of a new investigational drug and, more specifically, if the myotube were cultured from cardiac muscle, new drugs for cardiac use could be evaluated with this system.

Accordingly, the bio-MEMS transducer herein disclosed could be used in a method for quantitating physiologic response to an agent. This method comprises measuring deflection of the cantilever caused by myotube contraction elicited by contact with the agent and correlating the measurement to effectiveness of the sensed agent in causing a myotube physiologic response.

Conversely, the bio-MEMS transducer of the present invention could be employed as a bioactuator wherein an applied electrical signal causes the piezoelectric microcantilever to deflect, thereby actuating the attached myotube. There are several variations of this embodiment. For example, the bio-MEMS transducer of can act as a bioactuator wherein an applied electrical signal causes the piezoelectric microcantilever to deflect, thereby actuating the attached myotube. Also, the bio-MEMS transducer acts as a bioactuator wherein a neuron is synapsed to the myotube so as to apply a stimulus thereto, thereby actuating the myotube, the piezoelectric microcantilever being responsive to the actuation. Additionally, the bio-MEMS transducer acts as a bioactuator wherein a neuron is synapsed to the myotube so as to apply a stimulus thereto, thereby actuating the myotube, the optical sensor being responsive to the actuation. The bio-MEMS transducer of may also be employed as a bioactuator wherein a signal or stimulus is applied to the piezoelectric microcantilever to deflect, thereby actuating the attached myotube responsively sending a signal to activate an associated sensory neuron. The bio-MEMS transducer may also be employed in a prosthetic system wherein the cultured myotube is responsively associated with a severed neuron providing a stimulus thereto so as to actuate the cultured myotube to deflect the piezoelectric microcantilever.

Yet another aspect of the invention includes a method of quantitatively measuring the physiologic response of cultured skeletal muscle to a test agent. This method comprises fabricating the bio-MEMS by depositing isolated mammalian myocytes onto a non-biological organosilane substrate patterned into one or more relatively flexible microcantilevers. The deposited myocytes are cultured so as to promote their growth into myotubes generally aligned along a lengthwise extent of the one or more microcantilevers having a free end. The method continues by contacting the myotubes with a test agent, then monitoring the one or more microcantilevers so as to detect any deflexion thereof due to a myotube physiologic response to the test agent and numerically quantitating the deflexion detected in the free end of the one or more microcantilevers as an indicator of myotube physiologic response to the test agent.

The method optionally includes the microcantilevers being coated with amine-terminated alkylsilane (3-Trimethoxysilyl propyl) diethylenetriamine (DETA). Also optional in the method is that depositing may preferably comprise a density of approximately 500-800 isolated myocytes and wherein culturing extends for about 10-13 days. In the method, the test agent is preferably, but not exclusively, selected from metabolic inhibitors, nutritional supplements, therapeutic compositions, investigational drugs, and combinations thereof.

Monitoring in a non-piezoelectric embodiment of the invention best comprises a laser and a photodetector mounted on x-y-z-θ translators associated with a microscope and numerically quantitating comprises applying calculations to microcantilever deflexions detected, so as to numerically express deflection of the free end of the one or more microcantilevers.

Preferably, numerically quantitating in the method comprises applying Stoney's equation and associated calculations to microcantilever deflexions detected, so as to numerically express deflection of the free end of the one or more microcantilevers.

In this application it should be understood that the terms "cantilever" and "microcantilever" are used interchangeably and are intended to identify the same component of the invention. Other terms are intended to have their ordinary meaning in the art to which they apply, as known to those of skill therein, unless the context clearly indicates a different meaning. For example, the term "transducer" is used herein as known in the art for a device that converts one type of energy into another. This conversion could be to or from electrical, electromechanical, electromagnetic, photonic, photovoltaic, and other forms of energy. In the present case the transducer employs a piezoelectric microcantilever having a myotube attached thereto. When the myotube contracts, it bends the microcantilever generating a piezoelectric signal. Conversely, if an electric signal is applied to the piezoelectric microcantilever, it will bend in response to the applied electric signal and as a result of the bending it will at the same time actuate the myotube. Accordingly, the presently disclosed bio-MEMS transducer may be employed as a sensor or as an actuator.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 1A) the layout of a single die, the outer boundaries, delimited by dashed lines which formed connecting tabs allowing the die to be easily separated, were designed to be 14.8 mm×14.8 mm; FIG. 1B) close-up view of a partial microcantilever row showing microcantilever dimensions (737 mm×100 mm) and spacing between microcantilevers (300 mm);

FIGS. 3A-3D show SEM and confocal microscopy measurements of microcantilever and tissue thickness, wherein FIG. 3A) is a low magnification view (50° takeoff angle) of silicon microcantilevers; FIG. 3B) shows high a magnification view (50° takeoff angle) of microcantilever showing the measured thickness; FIG. 3C) is a top-down view of cultured myotube taken by confocal microscopy; and FIG. 3D) shows a digitally reconstructed side-view of cultured myotube showing measured thickness;

FIG. 6B) shows peak stress plotted as a function of film thickness; the arrow indicates calculated stress value for 10 mm film thickness;

FIG. 10A shows a perspective view of the microcantilevers of the present invention and FIG. 10B shows myotubes growing on the microcantilevers;

FIGS. 11A-E show myotubes immunostained with neonatal myosin heavy chain (N3.36); scale bar: 75 micro; FIG. 11A) phase picture of 2 myotubes shown by white arrows; FIG. 11B) both the myotubes shown in phase (FIG. 11A) have acetylcholine receptor clustering shown by alpha-bungarotoxin staining; FIG. 11C) only one myotube out of the two seen in FIG. 11A stained for N3.36, which is the neonatal, heavy chain antibody; FIG. 11D) double stained picture of the FIG. 11A with alpha-bungarotoxin and N3.36; FIG. 11E) representative current clamp trace;

FIGS. 13A-F show fetal skeletal muscle myotubes immunostained for adult MHC isoforms; (FIG. 13A) phase contrast image, (FIG. 13B) BF-F3 type IIb staining, (FIG. 13C) color composite, (FIG. 13D) phase contrast image, (FIG. 13E) BA-F8 type I staining, (FIG. 13F) color composite; scale bar=75 μm;

FIG. 14A) simplified schematic of AFM-based detection system; FIG. 14B) phase contrast image of a myotube from post natal rat grown for 8 days on silicon cantilevers; FIG. 14C) fluorescence image of myotube stained for α-actin; arrow heads indicate the location of the myotube; FIG. 14D) experimental setup of detection system; FIG. 14E) oscilloscope reading of the voltage changes on the photodiode due to contractions of myotube utilizing periodic electrical field stimulation at 1 Hz; the top trace shows the timing of the stimulus trigger, while the lower trace shows the response on the photodiode (PD);

FIG. 15A shows the co-culture at day 9, 40×; a neuron with MN morphology sends out long axon toward a striated myotube as indicated by the red arrow; FIG. 15B shows striated myotubes can be found frequently in the coculture; the striations of the myotubes are indicated by the yellow arrows; FIG. 15C and FIG. 15D show hSKM on cantilevers, day 4 in serum-free growth medium;

(FIG. 16A) micro fabrication of cantilevers with piezoelectric elements (left) and, as an alternative approach, with piezoresistive materials (right); gray lines indicate final position of cantilevers; gold electrodes and wiring are deposited in a first step; second follows the formation of piezoelectric (or piezoresistive) layers; top electrodes are Deposited in order to apply/read voltages across the zo piezo-layer for/during deflection; a final insulation layer protects all conducting elements from culturing conditions; (FIG. 16B) packaging of cantilever chips with printed circuit boards;

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references discussed or cited are incorporated herein by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Figure 1B:
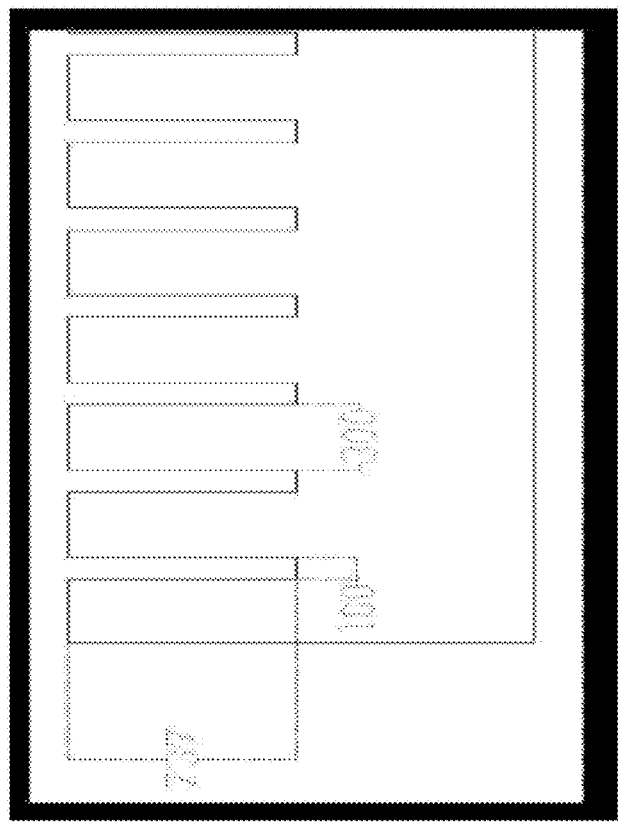
FIGS. 1A-B show a layout of microcantilever devices generated in AutoCAD, all units are shown in microns.
Figure 1A:
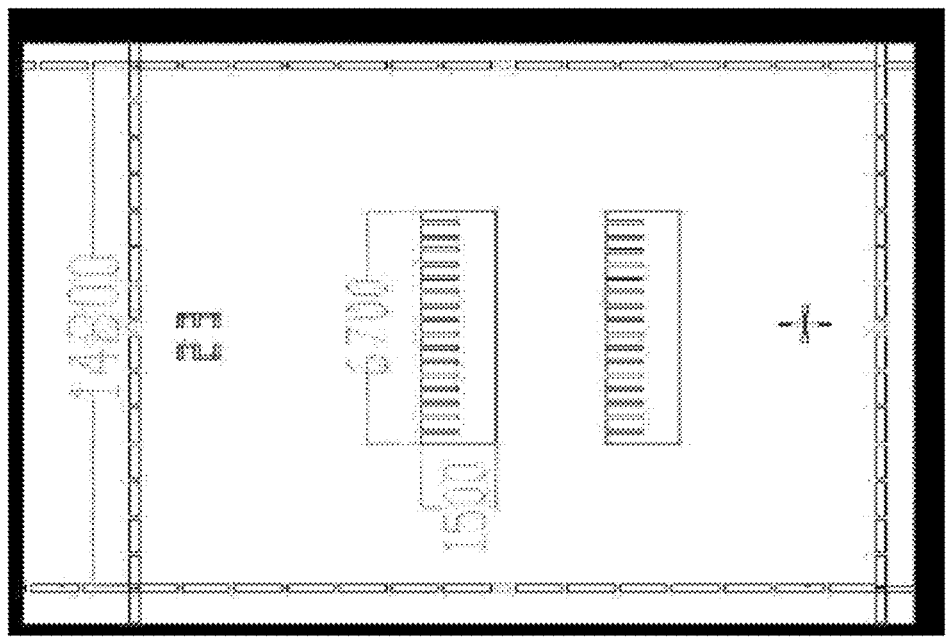

Part I
Combining Biological Elements with Microcantilevers
Materials and Methods: Microcantilever Fabrication The layout for the microcantilevers was generated using AutoCAD 2004 (FIG. 1). The patterns were written to chrome coated 4-5 inch soda-lime glass masks for front and back side photolithography. Microcantilevers were fabricated from 6 inch double-sided polished silicon-on-insulator (SOI) wafers with a 5 mm crystalline silicon layer (front side) and a 500 mm silicon dioxide layer (back side). The front side was primed with a 10 nm layer of hexamethyldisilazane (HMDS) to promote resist adhesion. A 5 mm layer of the photoresist AZ 5214 E (Clariant, Muttenz, Switzerland) was spun onto the device layer followed by softbake, alignment, exposure, and development. The device layer was etched using the deep reactive ion etch (DRIE) process at a rate of 2 mm/min. Resist was stripped and a 0.5 mm thick layer of silicon dioxide was deposited via Plasma Enhanced Chemical Vapor Deposition (PECVD) process to protect the device layer during subsequent processing. The wafer was then flipped over and was primed with a 100 Å layer of HMDS and spun with 4.15 mm layer of AZ 9245 photoresist (Clariant, Muttenz, Switzerland). Coating was followed by softbake, front-back alignment, development, and DRIE etch at 4 mm/min until the bulk of the back side had been etched through leaving only the buried native oxide layer. The devices were then immersed in a buffered HF dip to remove the buried native oxide layer as well as the protective silicon dioxide that had been deposited onto the device layer. Individual devices were separated by breaking connecting tabs that were incorporated into the device design. Microcantilever dimensions were measured using a JEOL 6400 scanning electron microscope (SEM) at a take-off angle of 50° off normal.

Prior to cell culture experiments the microcantilevers were coated with the amine-terminated alkylsilane (3-Trimethoxysilyl propyl) diethylenetriamine (DETA) according to previously established protocol. Prior to coating microcantilevers were cleaned using serial acid baths. Substrates were arranged in a porcelain coverslip holder (Thomas Scientific, Swedesboro, N.J.). The substrates were then immersed in a 1:1 (vol:vol) solution of methanol and concentrated HCl for at least 1 hour. This step removed surface contaminants. After 1 hour the substrates were rinsed 3× in diH$_2$O and transferred to a solution of concentrated sulfuric acid for at least 1 hour. This step oxidized the surface of the microcantilevers leaving a hydrophilic surface suitable for reaction of the silane derivatives. After at least one hour in sulfuric acid the substrates were washed 3× in diH$_2$O. The rinsed substrates were then boiled in diH$_2$O for 30 minutes. After boiling the samples were place in a 120° C. oven for at least 3 hours. The resulting surfaces were analyzed using contact angle goniometry and XPS to verify hydrophilicity of the surfaces (CA<5.0°) and the elemental composition of the surfaces respectively. Surfaces with a CA of less that 5.0° and an elemental carbon content of approximately 5.0% were considered suitable for derivitization.

After cleaning the microcantilevers, fresh distilled toluene was transferred into a Pyrex bottle that had been dried in an 120° C. oven to dry off excess surface water. Dry nitrogen was used to replace the air in the remaining volume of the bottle to minimize free oxygen. The bottle was sealed and placed in the antechamber of an MBraun glovebox, which was evacuated and refilled with dry nitrogen 3 times. The toluene was transferred into the main chamber. DETA was added to the toluene to a final concentration of 0.1% (vol:vol). The DETA-toluene solution was removed from the glove box and transferred to a pyrex beaker and the samples were immersed in the solution. To drive the reaction forward the solution was gently heated to no more than 65° C. Optimal reaction time was analyzed for these conditions by incubating the samples 10, 20, and 30 minutes. After reaction with DETA the samples were allowed to cool to room temperature, washed 3 time with dry tolune and heated too 65° C. for 30 more minutes. The resulting samples were analyzed by XPS and contact angle goniometry.

Cell Culture

Skeletal muscle was dissected from the hind limb thighs of a rat fetus at embryonic day 18 (Charles River Laboratories, Wilmington, Mass.) according to a previously published protocol with some modification. Tissue samples were collected in a sterile 15-ml centrifuge tube containing 1 ml of calcium and magnesium free phosphate buffered saline (PBS). Tissue samples were enzymatically disassociated using 3 ml of 0.05% of trypsin-EDTA (Invitrogen, Carlsbad, Calif.) solution for 60 min in a 37° C. water bath with agitation of 100 rpm. After 60 min, the trypsin solution was removed and 6 ml of L15 media (Invitrogen, Carlsbad, Calif.) containing 10% fetal bovine serum (FBS) was added to terminate the trypsin action. The tissue was then mechanically triturated using a sterile narrow bore Pasteur pipette, allowed to settle for 3 min, and transferred to a 15-ml centrifuge tube. This was repeated three times. The dissociated tissue was then centrifuged at 300 g for 10 minutes at 4° C. on 6 ml of a 4% (wt/vol) cushion of bovine serum albumin (BSA). The pellet was resuspended in 10 ml L15+10% FBS and plated in uncoated 100-mm Petri dishes for 20-30 min depending on the amount of tissue, to allow contaminating fibroblasts to settle out. After 20-30 minutes the supernatant was layered on 6 ml of a 4% BSA cushion, and centrifuged at 300 g for 10 min at 4° C. The pellet was resuspended in 1.5 ml of medium.

Purified myocytes were plated at a density of 500-800 cells per square millimeter onto the microcantilevers. Myocytes were allowed to attach for 1 hour after which time 3 ml of culture medium (Neurobasal media containing B-27 [Invitrogen, Carlsbad, Calif.], Glutamax [Invitrogen, Carlsbad, Calif.], and Pencillin/Streptavidin) was added. Cultures were maintained in a 5% $CO_2$ incubator (relative humidity, 85%). Culture medium was exchanged every 4 days. Microcantilever/myocyte constructs were allowed to culture for 10-13 days. During this time myocytes fuse into functional myotubes capable of generating contractile stresses sufficient to deflect the microcantilever. These cultures were used in experiments for validating the use of Stoney's equations equation for calculating contractile stress of the myotubes.

Detection System

Figure 2:
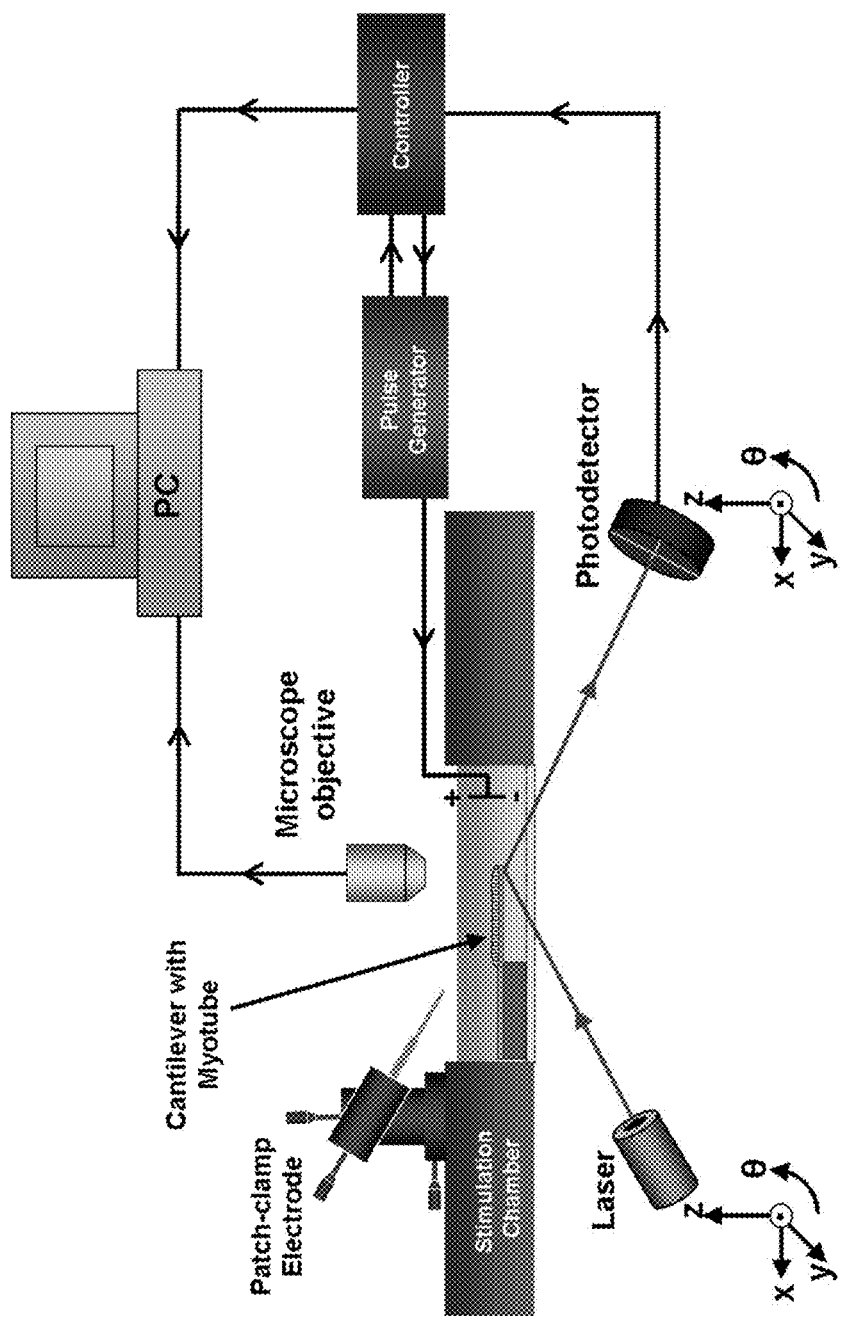
FIG. 2 depicts a schematic representation of an AFM detection system as might be used in the present invention.

A detection system similar to those used in atomic force microscopes (AFM) was designed for measuring deflection of the microcantilevers during myotube contraction and is illustrated in FIG. 2. The entire system was assembled around an upright Olympus BX51WI electrophysiology microscope (Olympus Inc., Center Valley, Pa.). The detection system consisted of a class 2 red photodiode laser (Newport, Irvine, Calif.), a stimulation chamber, a 4-quadrant photodetector (Noah Industries, Melbourne, Fla.), and a computer with pClamp 10.0 data acquisition software (Molecular Devices, Union City, Calif.). The laser and photodetector (PD) were mounted on x-y-z-θ translators (Newport, Irvine, Calif.) which were mounted on the underside of the microscope stage. The stimulation chamber was fabricated from 6 mm thick polycarbonate sheet. An approximately 15 mm×15 mm square chamber was milled out of the sheet and fitted with silver wires (0.015 inch diameter) for field stimulation. The silver wires were mounted parallel to each other with a separation of 15 mm. The bottom of the chamber was sealed using a 22 mm×22 mm glass coverslip. This created a transparent base through which the laser beam could easily pass. The silver wires were connected to an external pulse generator (A-M systems, Sequim, Wash.) capable of producing field stimulation pulses of varying intensity, frequency, and waveform. Both the pulse generator and PD were connected to an Axon Instruments series 1440 digitizer (Molecular Devices, Union City, Calif.) which was interfaced with the computer.

System Calibration

The AFM system was calibrated using a modified version of the optical lever method. A bare microcantilever die, without cells, was placed in the stimulation chamber. The laser was focused on one of the microcantilevers and the PD was adjusted so that the laser fell on the diode surface. Using a digital volt meter to monitor the output voltage, the PD was adjusted so that the voltage being read was less than −7 volts. The PD was then moved vertically in 5 mm increments and the voltage recorded at each position. The results were plotted in Excel and a linear regression line was fitted to the linear region of the calibration curve, which was the region between −5 and 5 volts. The slope of this region was the detector sensitivity (ydetector). This value was used to calculate the angle, θ, of the deflection at the end of the microcantilever using the equation:

$$\theta = \frac{y_{measured}}{2\cos(\varphi) l \times y_{detector}} \qquad \text{Equation 1}$$

where, y measured is the voltage measured from the PD, φ, is the angle of the detector to normal, and l, is the path length of the reflected laser beam.

Stress Calculation

The stress exerted by a myotube attached along its length to a microcantilever can be estimated by considering the system as a microcantilever bimorph and using Stoney's equation, which relates the stress in a bimorph system (film on substrate) to curvature of the substrate and the mechanical properties and thicknesses of the substrate and adherent film layer. The film stress, sfilm, is:

$$\sigma_{film} = \frac{1}{6Rt_{film}} \left[ \frac{E_{beam} t_{beam}^3}{(1 - v_{beam})(t_{beam} + t_{film})} + \frac{E_{film} t_{film}^3}{(1 - v_{film})(t_{beam} + t_{film})} \right] \qquad \text{Equation 2}$$

where Ebeam and vbeam are the microcantilever material modulus (130 GPa) and Poisson's ratio (0.28), respectively, tbeam is the microcantilever thickness, tfilm is the myotube thickness, R is the effective radius of curvature of the beam caused by the stress in the myotube layer, $\sigma_{film}$.

Many applications of Stoney's formula, most recently for studies of deposited and adsorbed films on thin substrates or microcantilevers, neglect the second term in the brackets because the films are much thinner than the substrate. In the present Bio-MEMS system, this assumption is not satisfied ($t_{film}$ ~10 μm compared to the microcantilever thickness, $t_{beam}$>>5 μm). However, for the system we also neglect this term because the modulus of the myotube cells comprising the film on the microcantilever are expected to be in the kPa range, at least 6 orders of magnitude lower than the modulus of the beam substrate Si (130 GPa). Thus we write:

$$\sigma_{film} \approx \frac{E_{beam}(t_{beam}^3)}{6(1 - v_{beam}) t_{film}(t_{film} + t_{beam})} \frac{1}{R} \qquad \text{Equation 3}$$

The radius of curvature of the microcantilever during contraction was calculated using the raw voltage data collected from the PD. This was done taking into account the geometry of the system (path length of the reflected laser, sensitivity of the detector, etc.). From the raw data the change in angle of the end of the microcantilever, θ, was calculated using equation 1. Using θ it was then possible to calculate the deflection of the free end of the microcantilever, d, by the relation from Butt et al:

$$\delta = \frac{2\theta L}{3} \qquad \text{Equation 4}$$

where, L is the length of the microcantilever. Experimentally, 1/R is estimated using the measured beam deflection and the geometric approximation from Ratieri et al.:

$$\frac{1}{R} \approx \frac{3\delta}{2L^2} \qquad \text{Equation 5}$$

From FIG. 2 it can be seen that tensile or compressive stress in the myotube film will result in an upward or downward vertical deflection of the microcantilever beam. Measured deflections from the photodiode detector will be reported as positive and negative deflection δ, respectively. Since the myotube film is grown on the top face of the microcantilever array, deflections due to tensile (positive values) or compressive (negative values) stresses in the film are consistent with standard conventions. All calculations were performed using Matlab.

Immunostaining and Confocal Microscopy

After AFM measurements the tissue samples were washed 3× with PBS, then fixed for 15 minutes in 4% (vol/vol) paraformaldehyde at room temperature. Tissues were permeabilized and blocked in a single step using a solution of 0.1% Triton-X100 in PBS, with 10% donkey serum. Blocking and permeabilization were allowed to proceed for 1-2 hours. Afterward, the samples were washed 3× in PBS and incubated with a mouse anti-myosin heavy chain primary antibody (Developmental Studies Hybridoma Bank, Iowa City, Iowa) overnight at 20° C. Following incubation with the primary antibody, the tissues were washed 3× with PBS and incubated with a donkey anti-mouse secondary conjugated with Alexa Fluor 594 (Invitrogen, Carlsbad, Calif.) at room temperature for 1-2 hours. The final stained samples were washed again with PBS and imaged under PBS using confocal microscopy.

Myotube thickness was measured by optical sectioning with a Perkin Elmer Ultraview spinning disc confocal microscope (Perkin Elmer, Waltham, Mass.) under a 40× water immersion lens. The 40× lens was mounted on a piezoelectric z-step motor with a minimum step size of 0.4 mm and a total travel length of 60 mm. Images were collected in 0.5 mm steps from the surface of the microcantilever to the top of the tissue. The "z-stack" of images was reconstructed using a 3-D rendering program provided with the microscope. The thickness of the myotube was then measured using the reconstructed image and an internal reference scale.

Exogenous Factors Added to Muscle Culture

In order to demonstrate the usefulness of this device for studying the biology of muscle development and function, experiments were conducted using exogenously applied factors to elicit a measurably different response of the muscle compared to control conditions. The sodium channel agonist veratridine was added to normally cultured myotube on microcantilevers and the response was measure with the AFM detection system. After 10 days of culture the myotube/microcantilever constructs were place in the AFM detection system and stimulated with a 1 Hz pulse to elicit synchronous, detectable contraction. Upon confirmation of synchronous contraction veratridine was added to a final concentration of 5 mM, and the resulting contractile behavior recorded.

Cultures were also performed in order to enhance the contractile capacity of the myotubes. The culture medium NbActiv4 was used in lieu of the Neurobasal/B27 formulation used for control cultures. Microcantilevers were seeded normally and cultured under conditions identical to those previously stated. After 10-13 days microcantilever/myotube constructs were placed in the AFM detection system and stimulated with a 1 Hz pulse train. The calculated values were then compared to previous experiments and published literature.

Results and Discussion

Characterization of Microcantilevers

When using Stoney's equation to estimate film stress on microcantilevers it is important to have precise knowledge of the thickness of both the beam and the film. FIG. 3 shows representative SEM micrographs of the microcantilevers used for the experiments. The microcantilevers were measured to have a mean length and width of 755+/−3 mm and 109+/−1 mm. As shown in FIG. 3B the mean thickness of the microcantilevers was measured to be 5.27+/−0.07 mm. Given these values one can expect a ~4% error in the stress estimation from experiment to experiment due to variation in beam thickness.

The spring constant of the microcantilevers was calculated theoretically and measured experimentally. The calculated spring constant, 1.21 N/m, was determined from the measured dimensions and Young's modulus for crystalline silicon, using formula for the spring constant of a rectangular microcantilever. The spring constant was determined experimentally using the method of Sader et al. 102. In short the resonant frequency was measured via ring-down experiment, and the resulting data processed by the spectrum analysis routines in the pClamp software. The resonant frequency in air was determined to be 88.5 kHz. Corrected for damping by air, the resonant frequency of the microcantilevers was found to be 88.7 kHz. This value was then applied to Sader's equation for calculating the microcantilever spring constant, which was found to be 1.26 N/m. Due to the high resonance frequency of the microcantilevers, it is expected that the resulting data reflects only the behavior of the myotube contraction as the response time of the microcantilevers is on the order of microseconds, whereas the time scale of the muscle contraction is on the order of milliseconds.

Myotube Culture

After plating the dissociated myocytes on the microcantilevers, the Bio-MEMS constructs were allowed to culture for 10-13 days during which time the myocytes fused into functional myotubes. During fusion and differentiation, the myotubes spontaneously orient along the long axis of the microcantilever, facilitating bending of the microcantilever. It should be noted, however, that the orientation of the myotubes was not always directly parallel to the long axis of the microcantilever. This configuration resulted in some torsional bending, and hence a possible underestimation of the total contractile stress. Typically the coverage of myotubes on microcantilevers was greater than 95%. Occasionally, tissue coverage was less due to tissue processing, suboptimal surface modification, and other systematic errors. Only robust cultures with morphologically normal looking myotubes were used for AFM experiments. FIG. 3c shows a confocal microscope image of a section of a representative myotube cultured for 13 days on a DETA modified microcantilever (not visible). FIG. 3a shows the top down projection of the z-stack in the plane of the microcantilever. The data from the z-stack of images were reconstructed into a 3-dimensional representation of the myotube geometry. FIG. 3b is a side view showing the thickness of the myotube along a section of the microcantilever. The mean thickness of the myotube was ~10 mm. Due to the morphology of the myotube, however, the thickness is not necessarily uniform throughout the length of the microcantilever. The thickness has been measured to range between 5 mm to 15 mm on an individual microcantilever. This variation in film thickness throughout the tissue can potentially lead to discrepancies between true and calculated stress values. In this study we used the average value of 10 mm for calculations. The effect of the thickness variation on the calculated stress is considered in a later section.

Stress Calculation

Figure 4:
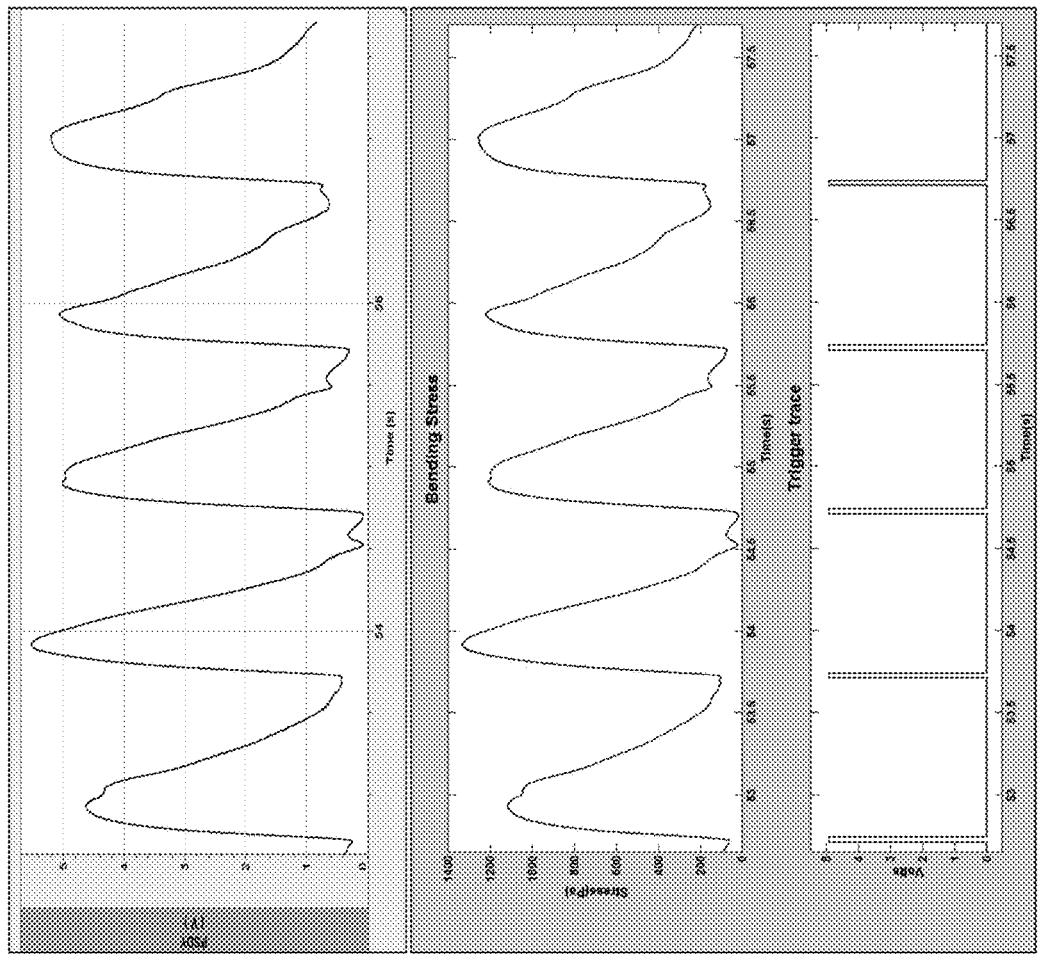
FIG. 4 presents raw data versus calculated stress for cultured embryonic muscle.

FIG. 4 shows both the raw voltage data from the PD and the resulting stress calculated using the Stoney's equation. FIG. 4a shows the raw data collected in free-run mode from myotubes cultured for 13 days and stimulated with a 5 volt DC pulse at a frequency of 1 Hz. As shown previously, this allowed selective stimulation of the myotubes to actuate the microcantilevers. Each trigger pulse, FIG. 4c, corresponds precisely with the onset of a myotube contraction. The myotubes responded to the stimulation in a frequency dependent manner; increasing or decreasing the stimulation frequency would result in a corresponding change in the frequency of myotube contraction. As with previously published results, stimulation at or above a frequency of 10 Hz induced a state of fused tetanus. FIG. 4b-c shows the resulting Stoney's calculation using the raw data. The stresses calculated from this data set range between 1.1 kPa and 1.4 kPa. These values are in excellent agreement with previously published literature for cultured skeletal muscle, which report average peak twitch stress values of 2.9 kPa (reported as specific peak twitch force in units of kN/m2), but less than 1% those expected for adult muscle, ~300 kPA. This is not surprising due to the fact that the tissue used in this study was collected from embryonic stage rat pups and cultured in vitro for only 13 days after dissection. It is possible that the culture conditions, as published here, are not sufficient for the development of myotubes with adult phenotype. Similar observations were made by Dennis and Kosnik 103 for cultured adult rat myoids noting the possibility of developmental arrest in culture preventing the development of adult isoforms of myosin.

Figure 5:
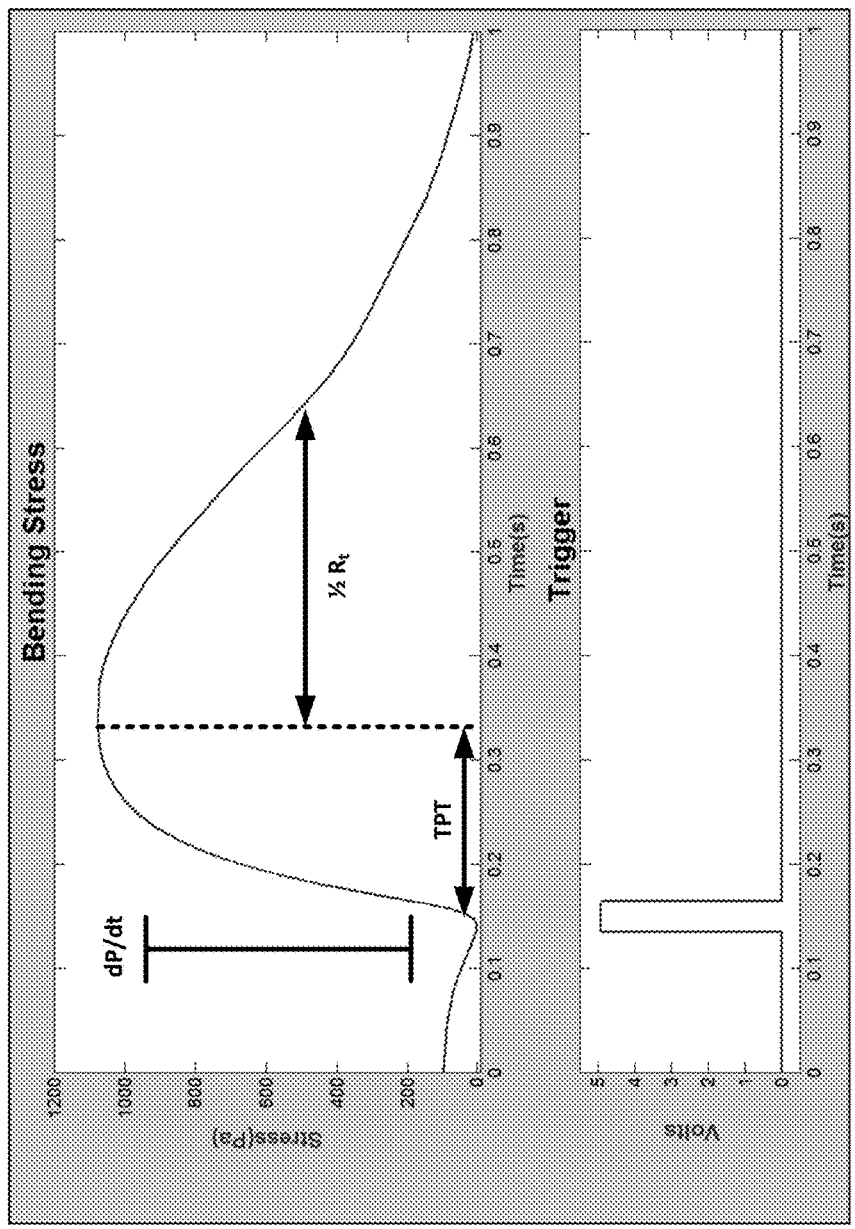
FIG. 5 indicates main parameters for muscle characterization.

To further characterize the myotubes, three other parameters were analyzed: the time to peak twitch stress (TPT) was measured, which is the time required to reach stress from the onset of contraction, time to half relaxation (½RT), which is the time require to relax to 50% of peak tension, and the average stress generation (ds/dt), which is the slope of the force curve between 20% and 80% of peak tension (FIG. 5). As shown in Table 1, the resulting average contractile stress for these data is ~1.2 kPa which is in agreement with previously stated results. The calculated values for TPT, and ½RT were significantly longer than those published for cultured muscle by Dennis and Kosnik 103 and for adult rat muscle as published by Close. The average TPT for the cultured myotubes was 236.8±26.1 ms. This value is considerably slower than that of 69.3±9.4 ms published by Dennis for cultured rat myoids as well as values of 65.0±3.8 ms and 36.0±2.3 ms, for neonatal and adult rat respectively, published by Close. The ½RT values for cultured myotubes were also prolonged compared to those reported by Dennis and Kosnik and Close. The average ½RT for the data presented in Table 1 was measured to be 233.6±23.8 ms. Dennis reported ½ART values of 116.4±19.4 ms for myoids, while Close reported values of 70.0±4.9 ms for neonatal muscle and 48.0±3.4 ms for adult muscle. It can be concluded from these data that the myotubes cultured in the Bio-MEMS system, while exhibiting contractile stress magnitudes comparable with those previously published for cultured rat muscle, show evidence of a more embryonic phenotype with regard to other important physiological parameters. This is further reinforced by previously published results showing staining of similarly cultured myotubes for embryonic myosin heavy chain, but not adult or fetal isoforms.

Variation in Stress Calculation Due to Film Thickness

Figures 6A, 6B:
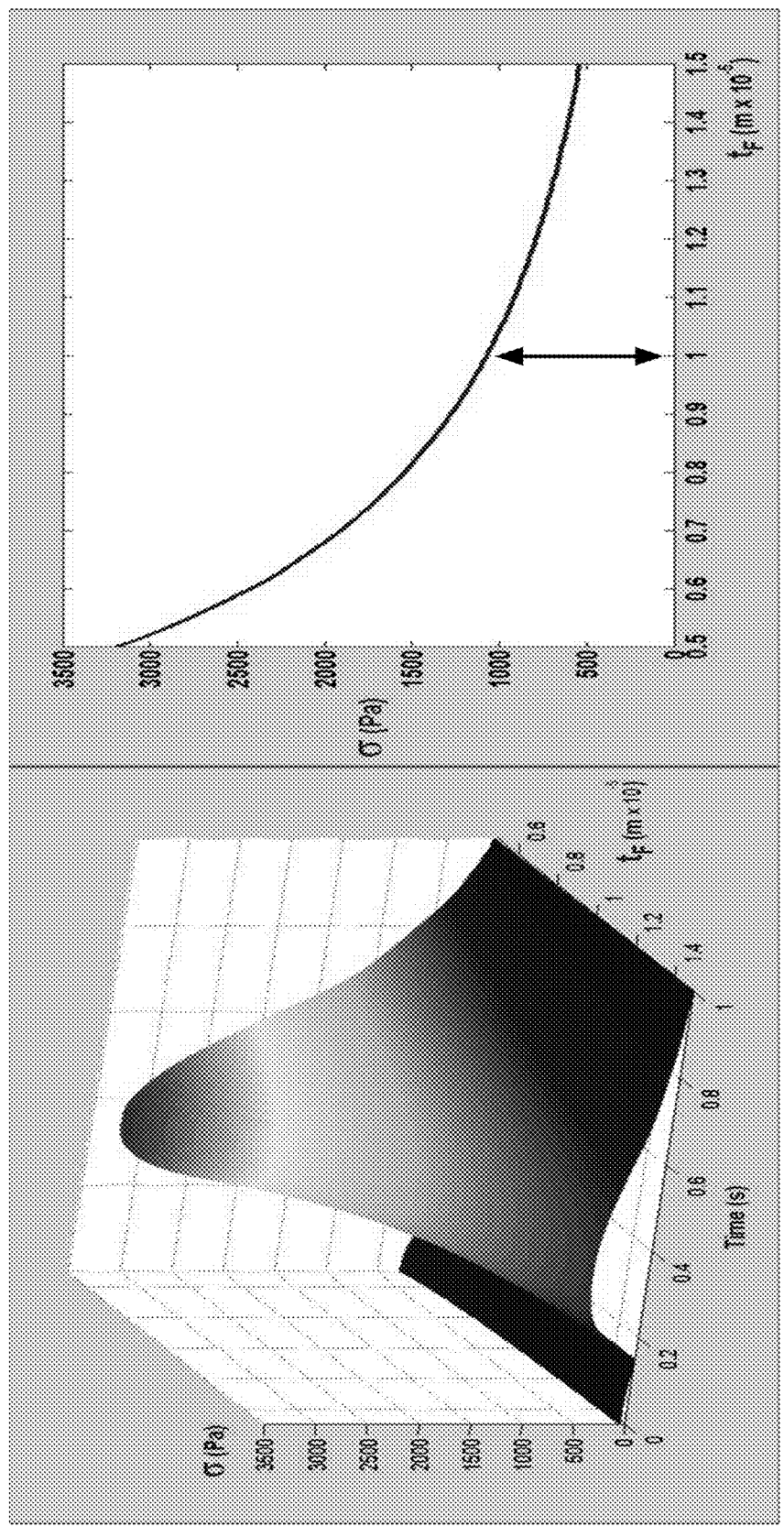
FIGS. 6A-B show stress variation with measured film thickness, wherein FIG. 6A) presents data recorded from a contracting myotube plotted as a function of time and measured film thickness.

As previously stated the thickness of the myotube film on the microcantilever has been measured to vary between 5 to 15 mm (FIG. 3). FIG. 6 shows the variation in calculated stress due to film thickness. FIG. 6a is a plot of the variation in calculated stress using the average of 11 contractions versus the film thicknesses used in the Stoney's calculation ranging from 5 to 15 mm. It is clear from this graph that there is a significant variation in the calculated stress due to the measured film thickness. Error! Reference source not found.b shows a plot of the calculated peak contractile stress vs. film thickness. In this plot it can be seen that the stress values range from ~0.5 kPa to ~3.2 kPa over the selected film thickness values. It is interesting to note that the Stoney's calculation is particularly sensitive to variations in the film thickness in the range encountered here. Below 5 mm the stress values increase exponentially. Above 15 mm the change in stress due to film thickness slows considerably. This reinforces the need for accurate measurements of the myotube thickness and standardization of the culture methods to minimize variations of the same. It should be noted, however, that even though there is obviously significant variation in calculated stress these values are still within the range of those published by Dennis and Kosnik (0.9 kN/m2 to 5.0 kN/m2). These results validate this approach as a method for measuring contractile stress generated by cultured skeletal muscle in a Bio-MEMS device.

Action Of Exogenous Modulators Of Myotube Function

The Sodium Channel Agonist Veratridine

Figure 7:
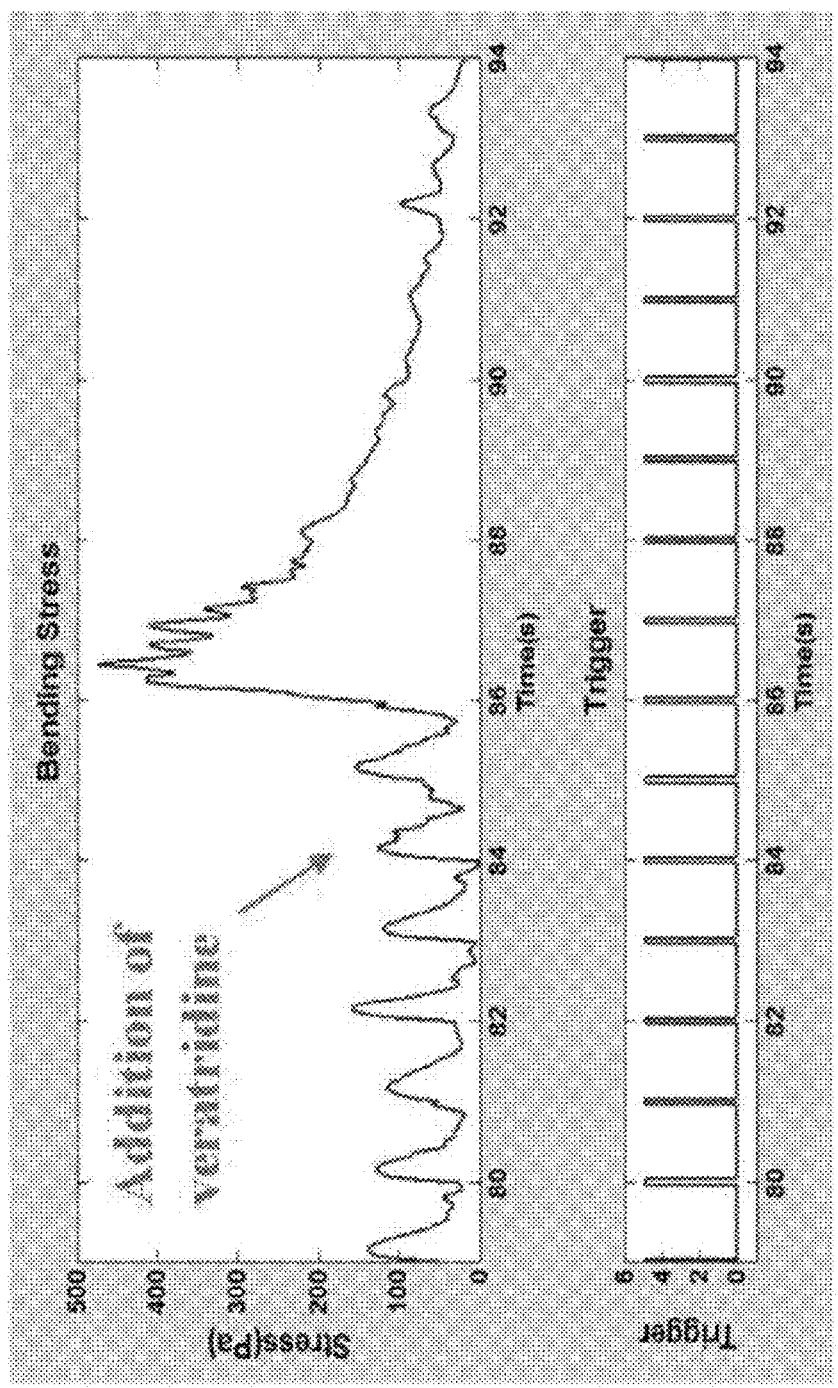
FIG. 7 presents line graphs generated when contractile myotubes were exposed to the sodium channel agonist veratridine; myotubes were contracting synchronously with the 1 Hz stimulus when, at 84 seconds into the recording, veratridine was injected; after injection of the toxin, the muscle tissue contracted in a tetanic manner and thereafter lost the ability to contract further.

Given the ability of this method for quantifying muscle contraction force and dynamics in real-time, it is ideal for studying the effect of exogenously applied factors on muscle physiology. One such example was the addition of the toxin veratridine to the stimulation chamber during electrical stimulation. Veratridine is an agonist that causes the persistent opening of voltage-gated sodium channels. Normally, upon depolarization of the cell membrane from electrical stimulation, voltage-gated sodium channels open allowing an influx of sodium ions into the cytoplasm which further depolarizes the sarcoplasmic reticulum causing calcium release and contraction. After a certain refractory period the voltage-gated sodium channels close and the resting membrane potential is restored. Veratridine binds to the voltage-gated sodium channels causing a persistent release of sodium into the cytoplasm followed by contraction, and if it is not removed cell death. FIG. 7 shows the recording of contracting skeletal muscle before and after addition of veratridine. Before addition the muscle was contracting normally in synchronization with the one Hz stimulus. At 84 seconds veratridine was injected into the stimulation chamber and allowed to diffuse to the tissue. As seen in FIG. 7 upon injection of the veratridine the muscle began to contract in an asynchronous, tetanic, manner with a peak stress far beyond those of the synchronized contractions. After the initial tetanic contraction, the muscle then lost the ability to further contract and the stress exerted on the microcantilever returned to baseline. This is the reaction that is expected upon exposure to this toxin.

Growth of Myotube in NbActiv4 to Enhance Muscle Contractility

Figures 8A, 8B:
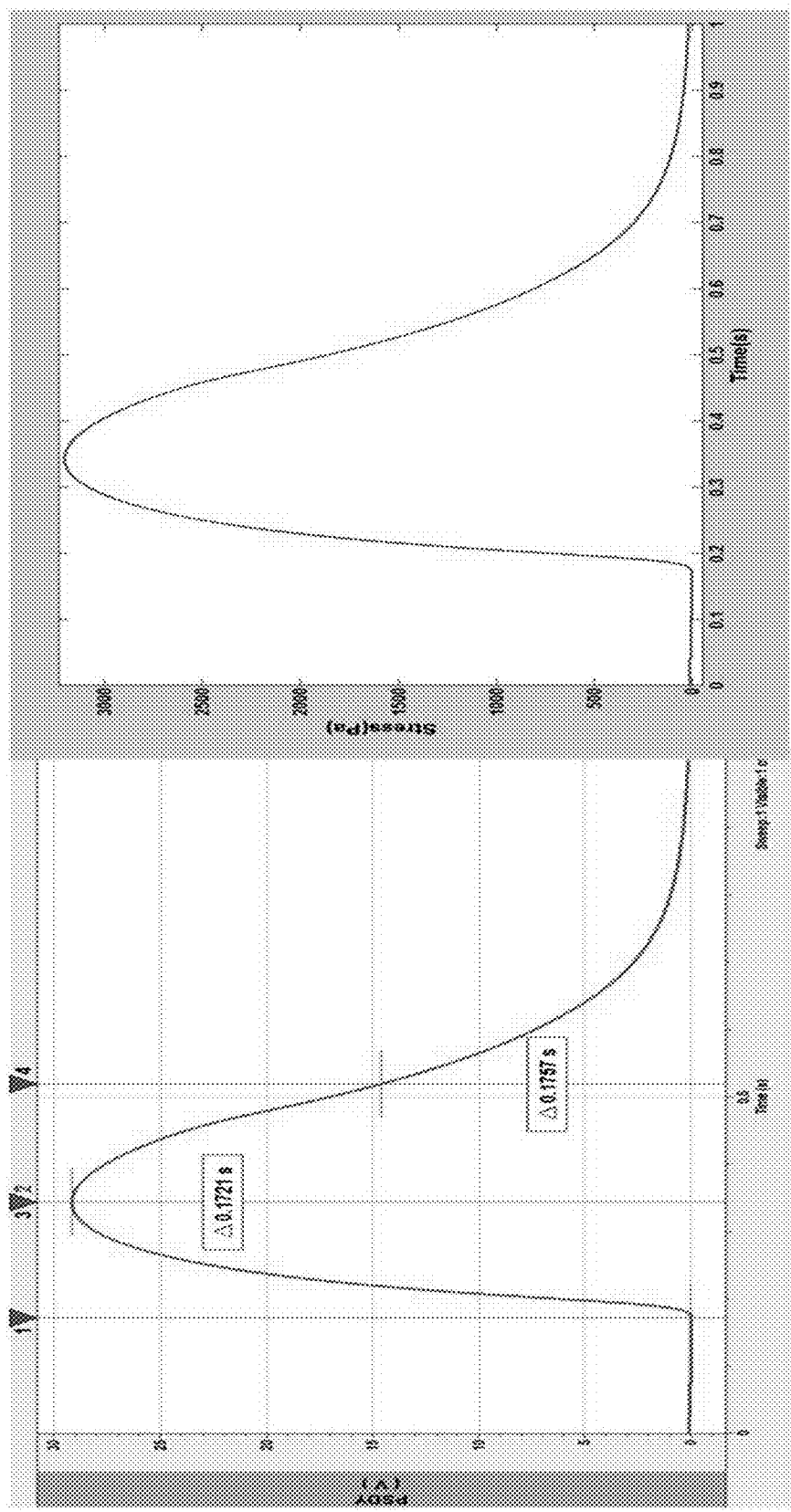
FIGS. 8A-8B illustrate contraction kinetics from muscle tissue cultured in NB4 media, wherein FIG. 8A) is raw data recorded from Bio-MEMS device showing TPT and ½RT, and FIG. 8B) shows stress values calculated using Stoney's equation.

As stated in previous sections, the contactile phenotype of the muscle cultured in this system was of an embryonic nature. For this device to serve as a model system for the study of normal muscle it is necessary to be able to culture muscle of a more adult phenotype. In order to do this it is necessary to supply additional factors that promote the development of more mature contractile properties in the myotubes. The culture medium NbActiv4 is a proprietary formulation based on Neurobasal medium and the growth factor cocktail B27104. NbActiv4 contains three additional growth factors (creatine, cholesterol, and estrogen) that have been shown to produce an eight-fold increase in spike activity in cultured neurons. However, these extra growth factors are also important for the development of the contractile mechanism of skeletal muscle. For this reason we cultured embryonic skeletal myotubes grown on silicon microcantilevers in NbActiv4 to quantify the changes in myotube development due to the added growth factors. FIG. 8 shows representative contraction data for myotube. FIG. 8a shows the raw data recorded by AFM for NbActiv4 cultured muscle. Here it can be seen that the TPT is measured to 172.1 ms and the ½ RT 175.7 ms.

Table 2 shows comparison of NbActiv4 cultured muscle with previously published results as well as myotubes cultured in Neurobasal/B27. It can be seen that the addition of NbActiv4 enhances the contractile properties of the myotubes significantly. Most notably the contractile stress generated by NbActiv4 myotubes, 3.2 kPa, is approximately 3 fold higher than those cultured in Neurobasal/B27, 1.1 kPa. Although this value is still much less than the stress generated by adult muscle, it is comparable to that published by Dennis and Kosnik 103. Also, TPT and ½RT values for NbActiv4 myotubes have decreased significantly compared to muscle cultured in Neurobasal/B27. This decrease in contraction time demonstrates that the myotubes are being pushed down a path towards a more mature phenotype, and developing fast-twitch isoforms of myosin, while increasing the speed of contraction. Furthermore, the increase in average stress generation (ds/dt) by almost five fold reinforces the argument that the contractile apparatus of myotubes grown in NbActiv4 is more mature and capable of greater stress generation.

Part II
Electromechanical Components of Other Preferred Embodiments

Having demonstrated above that cultured myotubes may be grown directly on MEMS devices such as microcantilevers, we now turn to the strictly electromechanical features of another preferred embodiment of the invention.

Since biological systems are considered unpredictable, we have herein provided data showing that our bio-MEMS devices work and are, thus, useful as a system for measuring the effect of additives on muscle contractility. These additives could be test compounds, for example, investigational drugs and the like. Muscle contractility causes deflection in the microcantilevers and can be measured by the optical laser device described. However, there are other approaches to measuring microcantilever deflection.

For example, if the microcantilevers are fabricated of a piezoelectric material or composite, deflection caused by myotube contractility generates a measurable piezoelectricity.

Since we have shown that cultured myocites may be grown into functional myotubes attached to microcantilevers we now consider the purely electromechanical features of another preferred embodiment of the invention. As with any other electrical and/or mechanical inventions, electromechanical structures function in predictable ways and these aspects of the present invention may be constructively reduced to practice without need of experimental proof, as required in a biological system.

In fact, piezoelectric microcantilever fabrication and function have been described by Choudhury et al., "A piezoresistive microcantilever array for surface stress measurement: curvature model and fabrication", in *J. Micromech. Microeng.*, 17 (2007) 2065-2076; and by Datar et al., "Cantilever Sensors: Nanomechanical Tools for Diagnostics", in *MRS Bulletin*, Vol. 34, June 2009, pp. 449-454. Both of these publications are incorporated herein by reference in their entireties.

Electromechanical Aspects of the Present Invention

Electrically stimulating a muscle cell or a myotube causes it to contract. This can be monitored using electrophysiology or by a direct force measurement. A benefit of direct force deduction is that artifacts due to the intracellular patch-clamp recordings are avoided and a closer approximation to in vivo conditions is achieved (Eisen and Swash 2001). In the present invention, because the cell is bound to the surface of the cantilever, the cantilever will also bend or deflect upon stimulation of the bound muscle cell or myotube. Examples of a myotube's ability to deform a silicon beam have been reported (Xi et al. 2005; Wilson et al. 2007). By measuring the deflection of a cantilever, the force exerted by a cell can be calculated. Microfabricated cantilevers are used routinely in atomic force microscopy (AFM) to measure small forces on the picoNewton to microNewton scale. The detector measures the cantilever's displacement using Hooke's Law, $F=-kz$, where $z$ is the cantilever displacement. The displacement can be measured by using an optical detector where the light beam from a diode laser is reflected off the backside of the cantilever onto a position sensitive detector.

Figures 9A, 9B:
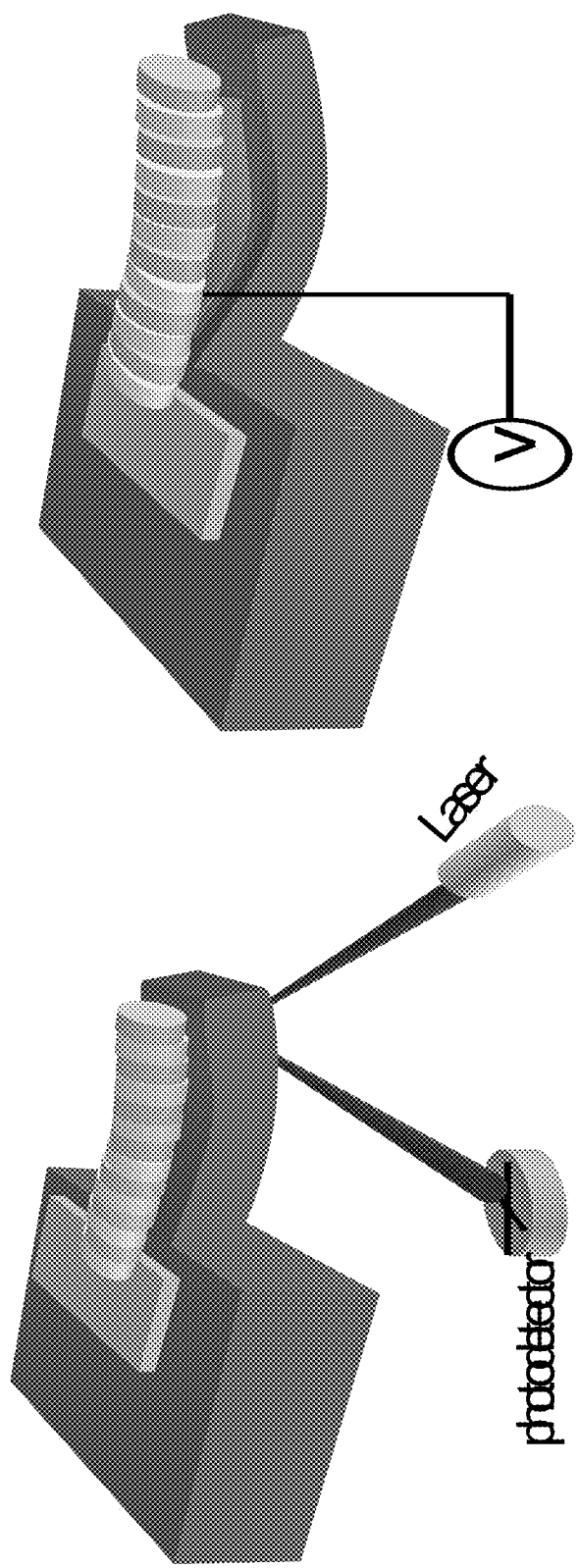
FIGS. 9A-9B show a schematic diagram of optical (FIG. 9A) and piezoresistive detection (FIG. 9B) of cantilever beam bending.

Microfabricated cantilevers have spring constants in the 0.01 to 100 N/m range and displacements as small as 0.01 nm can be measured with the optical detection scheme (FIG. 9). A muscle cell attached to a cantilever surface will have a similar effect to placing a coating or adsorbate on the cantilever surface and can be modeled as a bimorph using Stoney's relationship (Stoney 1909). In a bimorph cantilever system, a stress in the attached film (e.g. a muscle contraction) results in the beam bending; the stress in the film is balanced by the stiffness of the cantilever. Biosensing applications in general utilizing the cantilever system are reviewed by Raiteri (Raiteri et al. 2001). The forces exerted by contracting muscle cells and muscle fibers are of the order of μN but could be as high as several hundred μN for bundles (Yasuda et al. 2001). Hence, large cantilever deflections are anticipated even after accounting for geometric and mass-loading effects associated with attaching the cell to the cantilever and viscosity damping effects caused by operating in an aqueous environment. Also by growing myofibrils on a cantilever a 3D environment is established and since the cantilevers can bend in response to spontaneous contractions, myotubes do not come off these surfaces, so long-term cultures can be maintained (FIG. 10).

Force Measurements from Calculations of Myofibril/Cantilever Construct Stress Values The stress, or force, exerted by a myotube attached along its length to a cantilever can be estimated by considering the system as a cantilever bimorph and using Stoney's equation (Stoney 1909). Stoney's equation relates the stress in a bimorph system (film on substrate) to curvature of the substrate and the mechanical properties and thicknesses of the substrate and adherent film layer. We can calculate the film stress, $\sigma_{film}$ according to the following formula:

$$\sigma_{film} = \frac{1}{6Rt_{film}} \left[ \frac{E_{beam}t_{beam}^3}{(1-v_{beam})(t_{beam}+t_{film})} + \frac{E_{film}t_{film}^3}{(1-v_{film})(t_{beam}+t_{film})} \right] \quad (1)$$

where $E_{beam}$ and $v_{beam}$ are the cantilever material modulus (130 GPa) and Poisson's ratio (0.28), respectively, $t_{beam}$ is the cantilever thickness, $t_{film}$ is the myotube thickness, R is the effective radius of curvature of the beam caused by the stress in the myotube layer, $\sigma_{film}$.

Many applications of Stoney's formula, most recently for studies of deposited and adsorbed films on thin substrates (Sander et al. 1995) or cantilevers (Butt 1996; Moulard et al. 1998; Peterson et al. 1999), neglect the second term in the brackets because the films are much thinner than the substrate. In the present Bio-MEMS system, this assumption is not satisfied ($t_{film}$ ~10 μm compared to the cantilever thickness, $t_{beam}\approx$5 μm). However, for the system we also neglect this term because the modulus of the myotube cells comprising the film on the cantilever are expected to be in the kPa range, at least 6 orders of magnitude lower than the modulus of the beam substrate Si (130 GPa). Thus we write:

$$\sigma_{film} \approx \frac{E_{beam}(t_{beam}^3)}{6(1-v_{beam})t_{film}(t_{film}+t_{beam})} \frac{1}{R} \quad (2)$$

The radius of curvature of the cantilever during contraction can be calculated using the raw voltage data collected from a photodiode. This is done by taking into account the geometry of the system (path length of the reflected laser, sensitivity of the detector to laser spot position, etc.) (Meyer and Nabil 1988; Alexander et al. 1989). From the raw data the change in angle of the end of the cantilever, θ, is calculated. Using θ it is then possible to calculate the deflection of the free end of the cantilever, δ, which is then applied to equation 3 to calculate the radius of curvature, R.

Experimentally, 1/R is estimated using the measured beam deflection and the geometric approximation $$\frac{1}{R} \approx \frac{3\delta}{2L^2} \quad (3)$$

where L is the length of the cantilever and δ is the deflection of the free end of the cantilever (Butt 1996). From FIG. 9, tensile or compressive stress in the myotube film results in an upward or downward vertical deflection of the cantilever beam. Measured deflections from the photodiode detector are reported as positive and negative deflection δ, respectively. Since the myotube film is grown on the top face of the cantilever array, deflections due to tensile (positive values) or compressive (negative values) stresses in the film are consistent with standard conventions (Müller and Saúl 2004) and give a direct readout of the force exerted in the system.

Piezoelectric Devices

Piezoelectricity is the ability of certain materials (crystals and certain ceramics) to generate an electric potential in response to applied mechanical stress (Holler et al. 2007). The piezoelectric effect is used in various sensors to measure stresses or geometrical deformations in various mechanical devices. The reverse piezoelectric effect turns piezoelectric materials into actuators, when an external voltage is applied to the crystal (King et al. 2000). Piezoelectric materials are e.g. quartz, bone, sodium tungstate, zinc oxide, or lead zirconate titanate (PZT) (Lou 2009). A similar effect is the piezoresistive phenomenon. When subjected to mechanical stress, these materials change their resistivity (Mutyala et al. 2009).

Our current cantilever system, designed for force measurements of contracting muscle cells uses laser optics as a readout system (Das et al. 2007). Piezoresistive and piezoelectric approaches are the most widely applied techniques for measuring stress applied on microcantilevers (Waggoner and Craighead 2007). The advantage is that the mechanical device and the read out electronics can be implemented in the same integrated circuit as in FIG. 9. Replacing the optical readout with piezoelements would reduce the size and complexity of our current cantilever system.

Hybrid System Allows Functional Integration of Cultured Myotubes with a MEMs Device and Detection of Myotube Contraction.

Figure 11E:
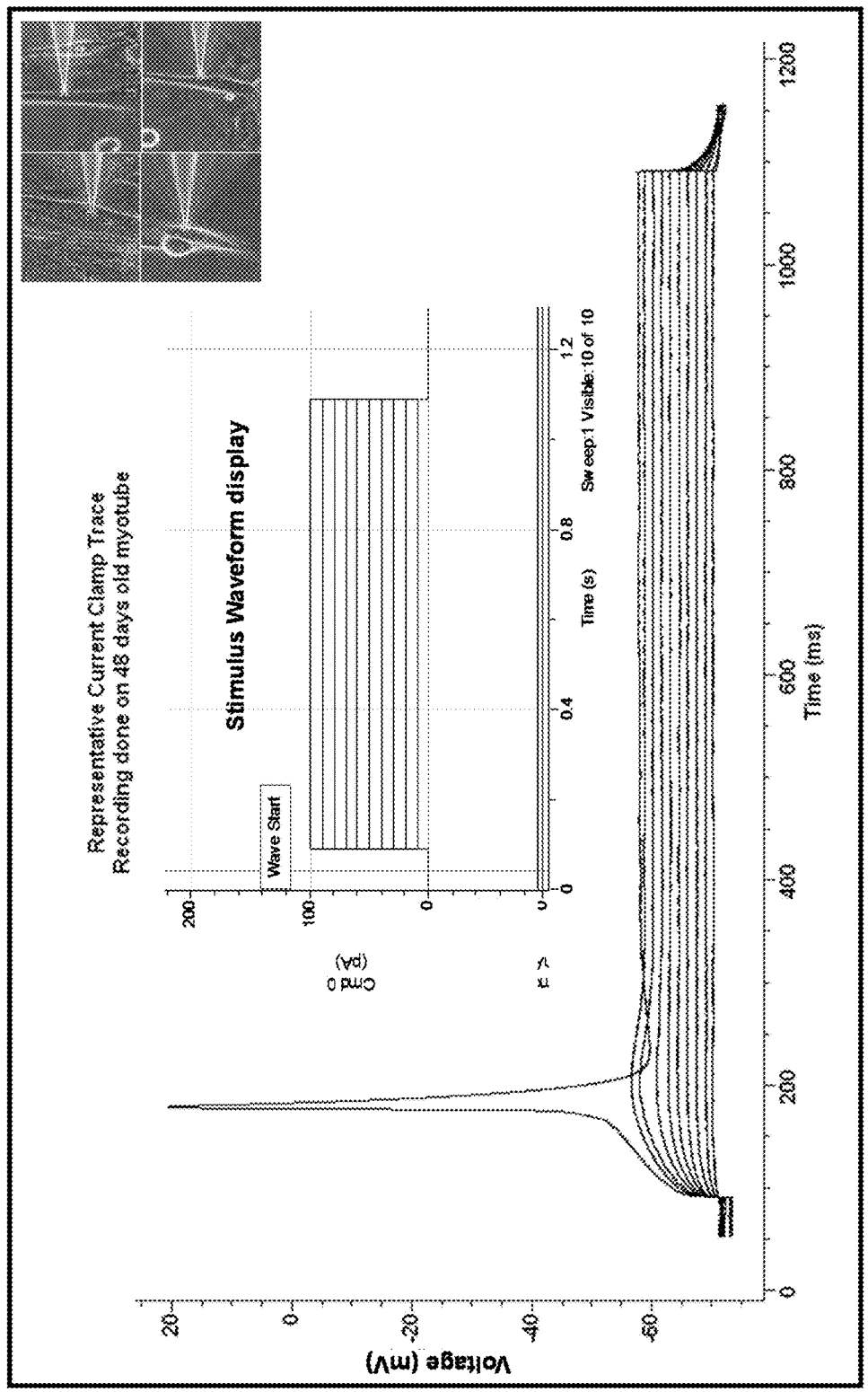
Figures 12A, 12B:
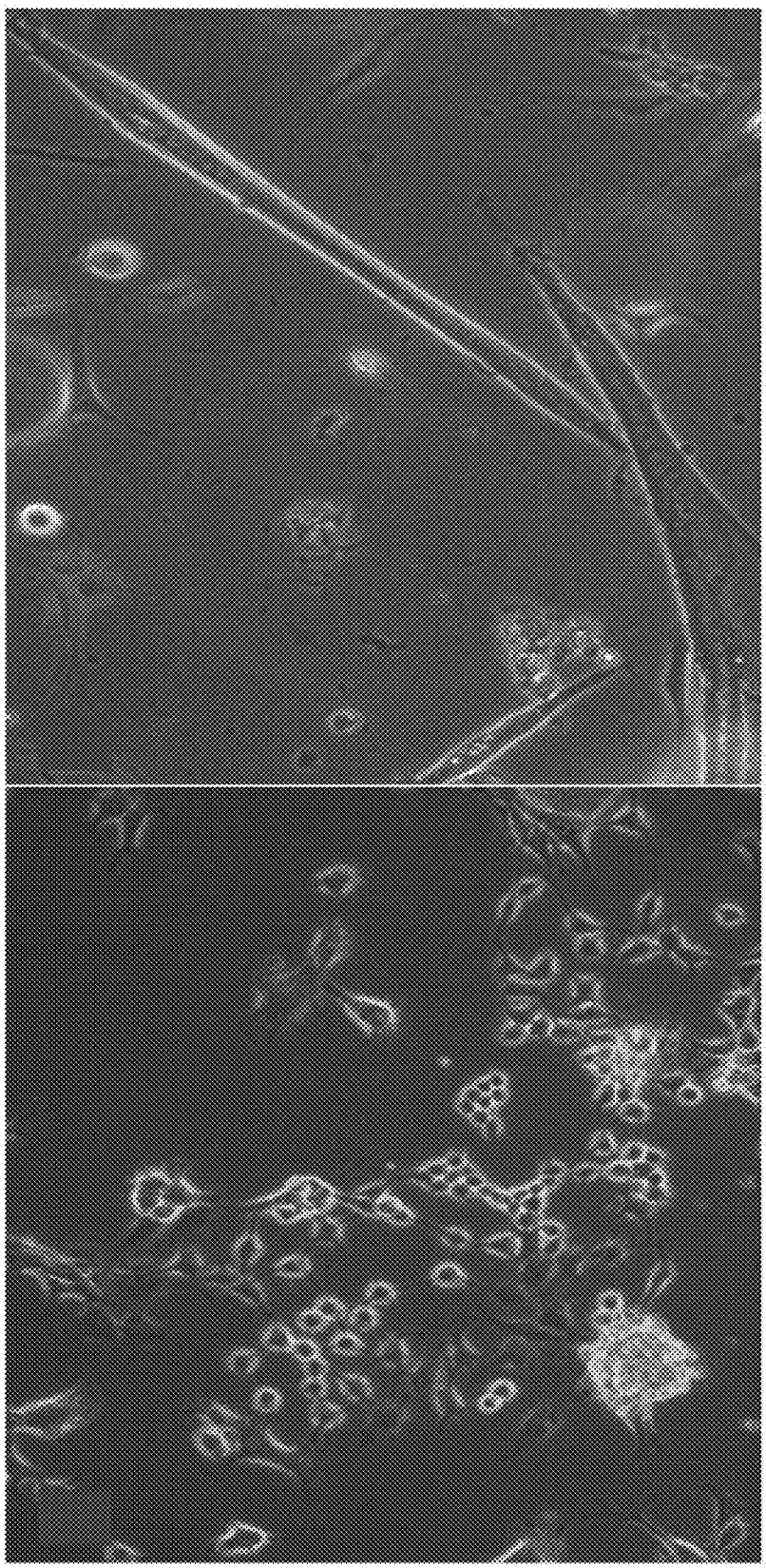
FIGS. 12A-B show adult rat satellite cell myogenesis, (FIG. 12A) day 5 satellite cell myoblasts and (FIG. 12B) day 7 myotubes formed by satellite cell fusion.
Figure 14A:
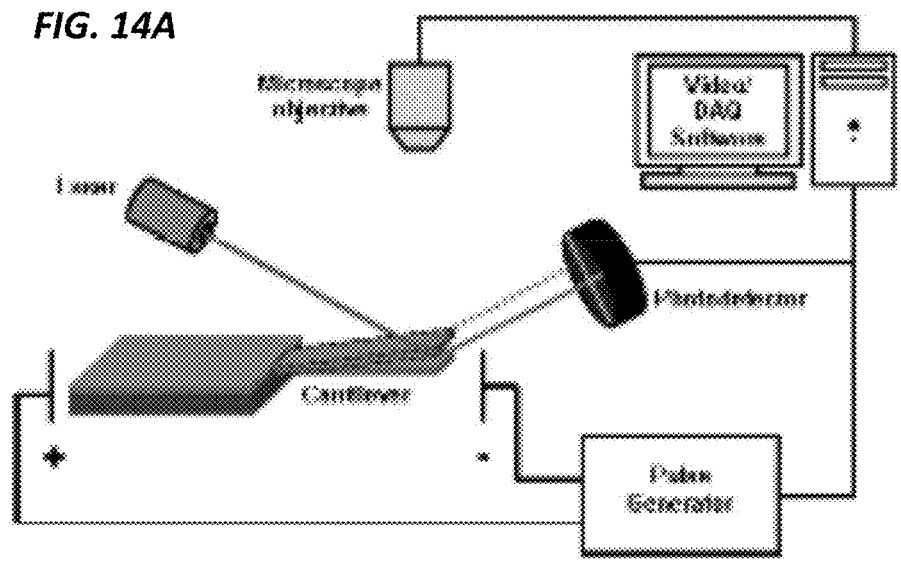
FIGS. 14A-E silicon based cantilevers and an AFM detection system, can be used to detect myotube contraction.
Figure 14B:
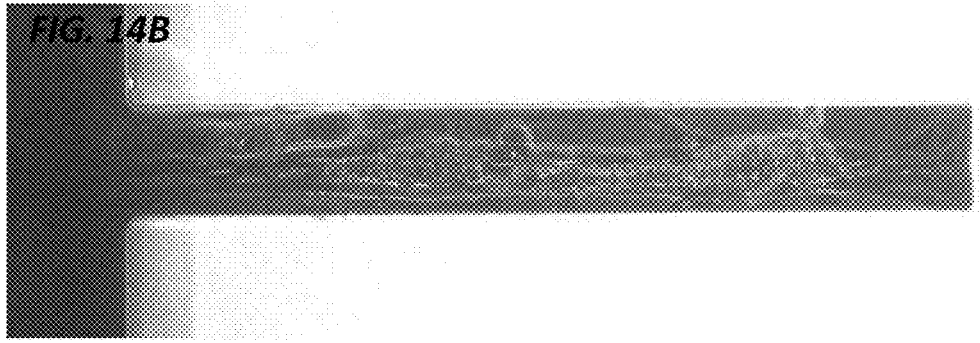
Figure 14C:
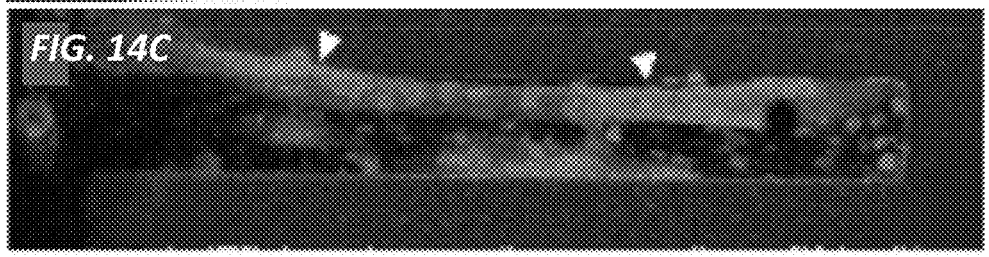
Figure 14D:
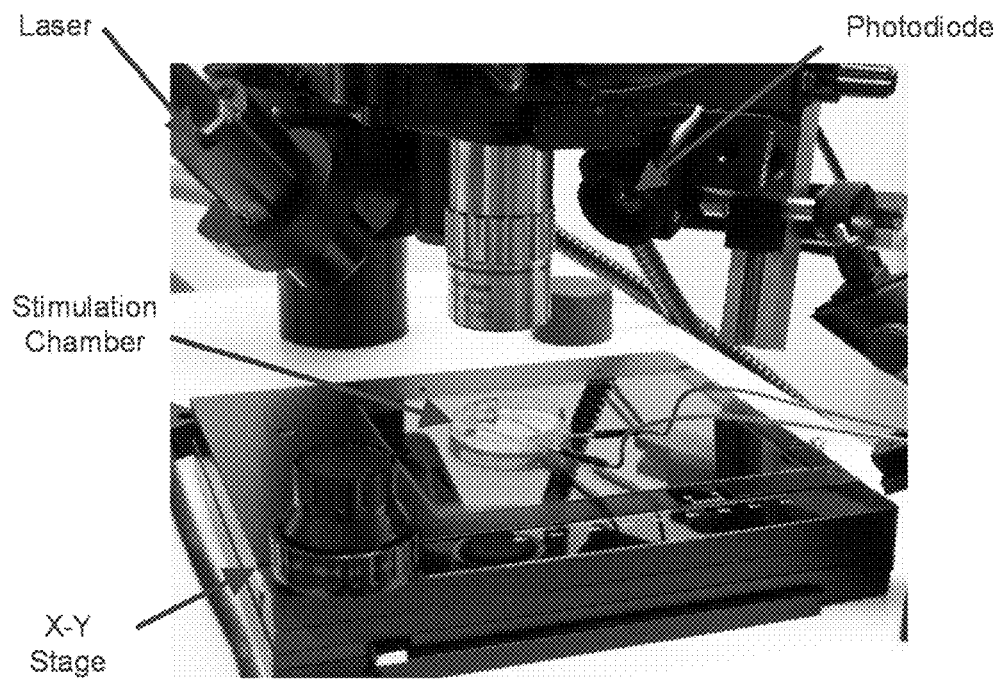
Figure 14E:
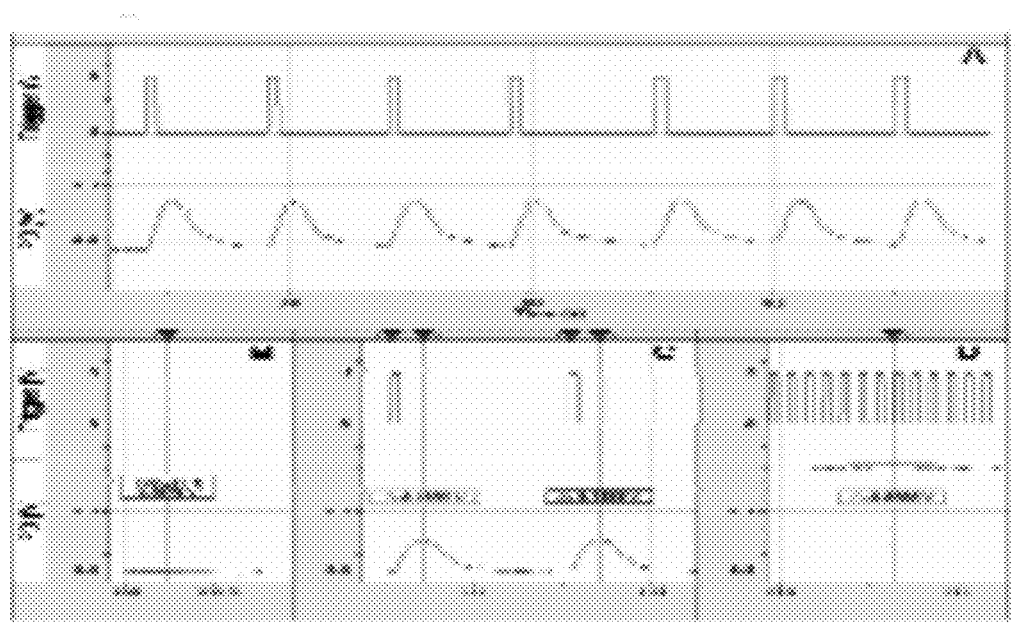

We have demonstrated methodology to create more fully differentiated muscle fibers that develop in a common medium that can also be used in the co-culture of motoneurons. These myotubes can be cultured out to 90 days on DETA ((Das et al. 2009), see paper in Appendix) and as shown in FIG. 11 are electrically active. We have fully developed the technology for the analysis of the functional myotubes on cantilevers. This work has been published as a Technical Note in *Lab-on-a-Chip* (Wilson et al. 2007). We have also been successful in preliminary attempts to fully differentiate embryonic rat myofibrils into adult isoforms as well as isolate satellite cells from adult rat muscle to form myofibrils in our defined, serum-free culture system as described below.

Growth of Myotubes in NbActiv4 to Enhance Muscle Contractility

For this device to serve as a model system for the study of normal muscle it is necessary to culture muscle of a more adult phenotype. Supplying additional factors that promote the development of more mature contractile properties in the myotubes is beneficial, as shown in FIG. 13. This would demonstrate that the system could be used to evaluate compounds that enhance myofibril development and functionality. The culture medium NbActiv4 is a proprietary formulation based on Neurobasal medium and the growth factor cocktail B27 (Brewer et al. 2008). NbActiv4 contains three additional growth factors (creatine, cholesterol, and estrogen) that have been shown to produce an eight-fold increase in spike activity in cultured neurons. However, these extra growth factors are also of importance in the development of the contractile mechanism of skeletal muscle. For this reason embryonic skeletal myotubes grown on silicon microcantilevers were cultured in NbActiv4 to quantify the changes in myotube development due to the added growth factors. FIG. 8A shows the raw data and calculated stress averaged from 11 myotube contractions (FIG. 8B) recorded by the photodiode for muscle cultured in NbActiv4. The resulting average contractile stress for these data is ~1.1 kPa, which is in agreement with previously stated results. To further characterize the myotubes, two other parameters were analyzed: the time to peak twitch stress (TPT) was measured, which is the time required to reach peak stress from the onset of contraction, and time to half relaxation (½ RT), which is the time required to relax to 50% of peak tension. Here it can be seen that the TPT is measured to 172.1 ms and the ½ RT 175.7 ms.

Table 1 shows a comparison of the NbActiv4 cultured muscle with previously published results as well as myotubes cultured in Neurobasal/B27. It can be seen that the addition of NbActiv4 enhances the contractile properties of the myotubes significantly. Most notably the contractile stress generated by NbActiv4 myotubes, 3.2 kPa, is approximately 3 fold higher than those cultured in Neurobasal/B27, 1.1 kPa. Although this value is still much less than the stress generated by adult muscle, it is comparable to that published by Dennis et al (Dennis and Kosnik 2000). Also, TPT and ½ RT values for NbActiv4 myotubes have decreased significantly compared to muscle cultured in Neurobasal/B27. This decrease in contraction time demonstrates that the myotubes are being pushed down a path towards a more mature phenotype, and developing fast-twitch isoforms of myosin, while increasing the speed of contraction. Furthermore, the increase in average stress generation (dσ/dt) by almost five fold reinforces the argument that the contractile apparatus of myotubes grown in NbActiv4 is more mature and capable of greater stress generation, and validates the use of the myofibril/cantilever system as useful for analyzing temporal changes in myofibril function in response to drug candidates.

We have also shown that satellite cells from adult human muscle (hSKM) can be cultured in our defined, serum-free system and are functionally active. FIG. 15 shows a co-culture of human derived myofibrils and human motoneurons with classical striations indicative of sarcomere formation and mature myofibrils, as well as muscle only culture on the cantilevers in the serum-free media system.

Fabrication of the Microcantilever Hybrid System Chip.

The cantilevers are microfabricated out of silicon or silicon nitride, and prepared using DETA SAM modifications of the surface for cell attachment. The designs for the cantilevers are generated using AutoCAD 2004. Once designs are completed the AutoCAD file is used to create the photomask for device fabrication. The photomask is fabricated from a fused silica wafer and coated with chromium. The micro-cantilevers are fabricated from crystalline silicon wafers using a deep reactive ion etching (DRIE) process. A double-sided polished 10 μm thick crystalline silicon wafer is bonded to a 500 μm $SiO_2$ handle wafer. The crystalline silicon surface is coated with a 1.3 μm layer of AZ 5214 photoresist. The photoresist is then exposed to a soft bake followed by contact exposure with the mask. The photoresist is then developed and hard baked. The wafer is mounted on a 6" handling substrate for DRIE. After DRIE the wafer is inspected and the photoresist removed via a wet strip followed by plasma cleaning. After etching is completed the wafer is cut into 15 mm×15 mm pieces which contain the cantilever arrays by dicing. Dicing is followed by HF release and supercritical $CO_2$ drying.

Detection System Setup and Measurements.

In preliminary and published studies we have already optimized the microcantilever length and thickness for producing an optimal deflection from a contracting myotube, although this can be adjusted if required. Our current configurations have proven sensitive enough to provide detailed force measurements of myotube contraction (Wilson et al. 2007) (See FIGS. 14, 8).

Alternatively, the SAM chemistry can also be modified to adjust cell/substrate adhesion. The deflection of the muscle-actuated cantilever is measured using optical detection. Actuation of the reflex arc is observed indirectly using diode laser beam bounce techniques and position sensitive detectors (i.e., standard AFM technology) as outlined in the preliminary data section of the proposal and in (Wilson et al. 2007). Initially, cantilevers are examined with SEM techniques to determine their average length, with and thickness. Subsequently, the average spring constant can be calculated by theoretical means and the Young's modulus for crystalline silicon. The spring constants are about 1.2 N/m.

Because of the large variability in the spring constants, cantilevers have to be further calibrated on an individual basis when used for precision force measurements. This variability is most likely caused by variations in thickness of the cantilever. Variability in the length and width is often quite small because typical lateral resolution in photolithography is on the submicrometer scale. For nominal spring constants greater than 0.1 N/m, we use the calibrated load-displacement transducer of a nanoindenter to measure the spring constant of each cantilever in an array. Measuring the resonance frequency of individual cantilevers and applying it to Sader's equation provides detailed spring constants. Another important value is the thickness of myotubes, located on cantilevers, in order to calculate their internal stress values. Confocal microscopy provides z-stacks of fluorescently died myotubes, which then can be analyzed for cell heights. The measurement is initially made in triplicate in order to determine the mean, standard deviation, and standard error of the sample set. The number of measurements may be increased in order to bring the range of the confidence interval to 99%.

Surface Modification and Characterization.

Trimethoxysilylpropyl-diethylenetriamine (DETA) has been demonstrated to support adhesion and growth of embryonic rat, adult rat as well as human myocytes and satellite cells. Tridecafluoro-1,1,2,2-tetrahydrooctyl-1-dimethylchlorosilane (13F) and polyethylene glycol silane (PEG) monolayers are cytophobic for this cell type. Self-assembled monolayers (SAMs) are prepared according to our published procedures (Hickman et al. 1994). In brief, silica slides are cleaned by immersion in 1:1 methanol/HCl, followed by $H_2O$ and then concentrated $H_2SO_4$. Cleaned substrates are then transferred to boiling water prior to reaction with the silanes. An alternative to this procedure, which may be necessary for the silicon devices, is to clean in a non-directional $O_2$ plasma. In general, SAMs are formed by immersing clean silica substrates in organic solvents containing 1-2% silane, and then rinsing the slide three times with the same solvent. After the final rinsing step, the slides are baked on a hotplate to quickly remove residual solvent and to promote complete reaction of the silanes with the reactive surface groups.

SAM-modified surfaces are characterized using XPS to demonstrate formation of the SAM and contact angle measurements to quantify wettability. Contact angle measurements are a rapid and simple measure of wettability. Contact angles are measured by application of static, sessile drops (5-30 μl) of deionized water to substrate surfaces with a micropipetter. The measurements are made visually on both sides of the drops using a Rame-Hart type goniometer. XPS is a technique for the elemental analysis and characterization of surfaces (Briggs 1992). Since the electrons of each element possess characteristic binding energies, the energy pattern of emitted photoelectrons arising from a given element serves to unambiguously identify that element, while the precise peak positions, or chemical shifts, reflect the chemical environment (i.e., oxidation state) in which the element is found. XPS measurements are obtained on a FISONS 220i XL spectrometer with imaging capability to 2 μm resolution. For each sample examined by XPS, we obtain a survey spectrum and high-resolution spectra for the elements Si, C, N, and any other element that is unique to the SAM (F for 13F). These measurements serve as (a) baseline quantities against which to contrast properties of the surface after cell culture, and (b) baseline quantities against which to contrast cell growth and survival from experiment to experiment for multivariate analysis.

Surface Patterning.

If necessary, surface patterns are made using projection lithography that avoids direct contact with the surface and is easily integratable with the barriers. SAMs prove an ideal tool for the design of circuits for the study of neuronal interactions in a defined minimalistic system. Lithographic patterns on a silica substrate are prepared by exposure of a SAM-modified surface to 193 nm UV light followed by re-derivatization with another SAM. This process has been described previously, and we have used this method to create patterns for the preferred attachment of several types of cells (Stenger et al. 1992; Spargo et al. 1994; Ravenscroft et al. 1998). We already have demonstrated that myotubes will grow on DETA, but not 13F or PEG and that patterns can be made. Masks are prepared as needed for experiments; changes and alterations are straightforward. XPS image analysis allows us to determine whether the initial silane modifier is removed from the surface with laser ablation, and to verify that rederivatization of the second silane has occurred. We then culture cells on patterned surfaces to determine fidelity to the patterns. We use phase microscopy to assess which SAM combinations result in specifically placed myofibrils.

Muscle Cell Preparation.

Primary culture of rat skeletal muscle cells is obtained by the methods used by Daniels and Nelson et al., (Shainberg et al. 1976; Daniels 1990; Nelson et al. 1993). Cell suspensions are obtained by trypsinization of muscle pieces from hind limbs of newborn rats. Cells are dissociated by incubation in trypsin, followed by resuspending the cells in L15 medium supplemented with 10% fetal calf serum to inhibit trypsin activity. The cells suspension is triturated and the supernatant is collected. The supernatant is centrifuged and the pellet resuspended in the serum free media developed in our laboratory. As an additional improvisation to this technique, after centrifugation the pellet is resuspended in a serum free medium and incubated in a 90 mm tissue culture dish, which results in the settling down of the fibroblasts such that the cells in the suspension consist of a pure population of myoblasts (Kuhl et al. 1982). The suspension is obtained and centrifuged and the pellet is resuspended in the culture media and is used for plating. The cells are plated at a density of 250 cells/mm$^2$. The myocytes (250 cells/mm$^2$) are plated in a serum free composition containing L15, Media 199, B27 supplement, GDNF, BDNF, Cardiotrophin, bFGF2, IGF, PDGF, Thyroxine. The medium is changed every 4th day. Cells can be maintained in this serum free media now for up to 3 months (Das et al. 2009).

Adult Rat Satellite Cell Culture

Primary culture of adult rat satellite cells is obtained by methods described by (Huang et al. 2005). Rat hindlimb tibialis anterior muscles are excised and minced into pieces. The tissue is dissociated by incubation in type II collagenase followed by resuspension in L15 medium supplemented with 10% fetal bovine serum to inhibit enzyme activity. The tissue suspension is triturated and then incubated in a 90 mm dish, which results in the settling down of the fibroblasts such that the cells in suspension consist of a pure population of satellite cells. The suspension is removed from the dish and centrifuged and the pellet is resuspended in culture medium followed by cell plating. The satellite cells are plated at a density of 400 cells/mm$^2$. The next day the medium is aspirated, pelleted and then replated. This is repeated the following day. This serial plating results in further enrichment of the satellite cell population (Malerba et al. 2009).

Fabrication and Characterization of the Piezoelectric Microcantilever System.

The advantage is that the mechanical device and the readout electronics can be implemented in the same integrated circuit. Replacing the optical readout with piezoelements reduces the size and complexity of the microcantilever system. Further, experimental data can be obtained from multiple cantilevers in parallel and the reverse piezoelectric effect can be used to employ the cantilevers as actuators to exercise muscle or activate intrafusal fibers enabling each cantilever to become a stand alone sensor element.

Prior to the fabrication of cantilevers, electrical circuits and piezoelectric components are applied to the silicon wafer. Subsequently, the actual cantilevers are etched exactly in those positions were piezoelectric components were placed. Individual piezoelectric cantilever chips are packaged with printed circuit boards providing up to 60 contact pads to allow the readout and control of piezoelectric cantilevers with a head stage usually used for multielectrode arrays (Multichannel Systems).

In the first part of this disclosure, we show that we can fabricate a cantilever assembly for the culture of embryonic myotobes an use it to measure contraction of the myotube by monitoring cantilever deflection using an AFM-like laser system. In this portion of the disclosure, we integrate piezoelectric elements onto the cantilevers to measure cantilever deflection.

Fabrication of a Piezoelectric Elements for Cantilever Arrays.

Figure 16B:
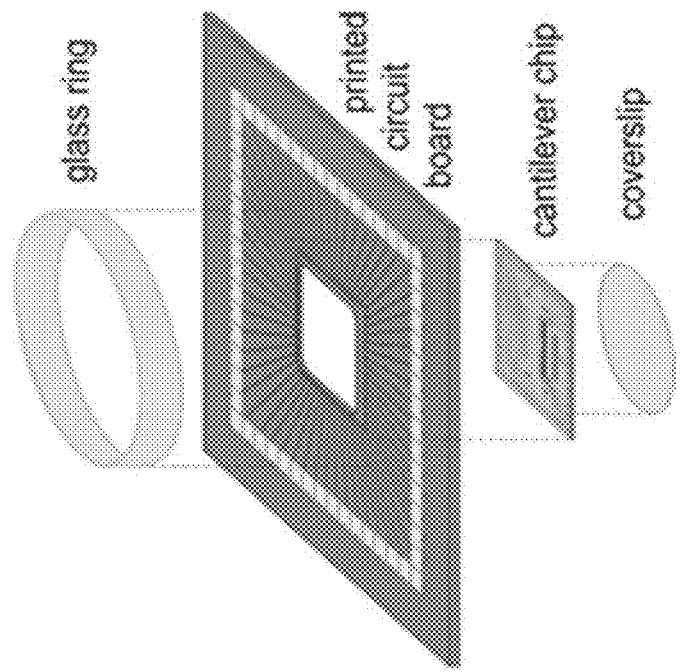
FIGS. 16A-B illustrate schematics of piezo-cantilever construction.
Figure 16A:
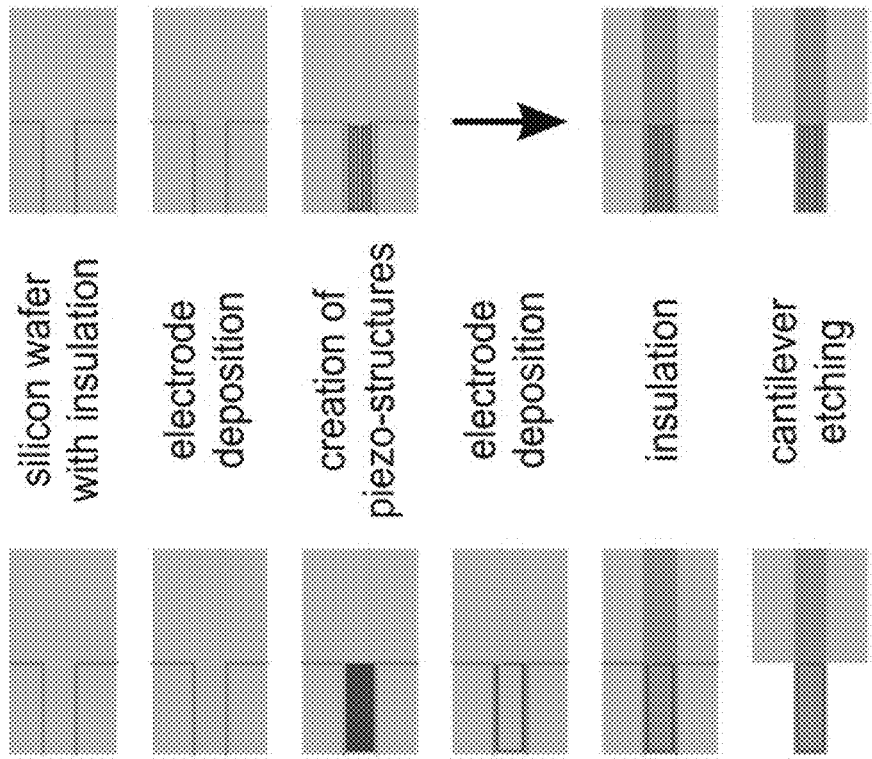
Figure 17:
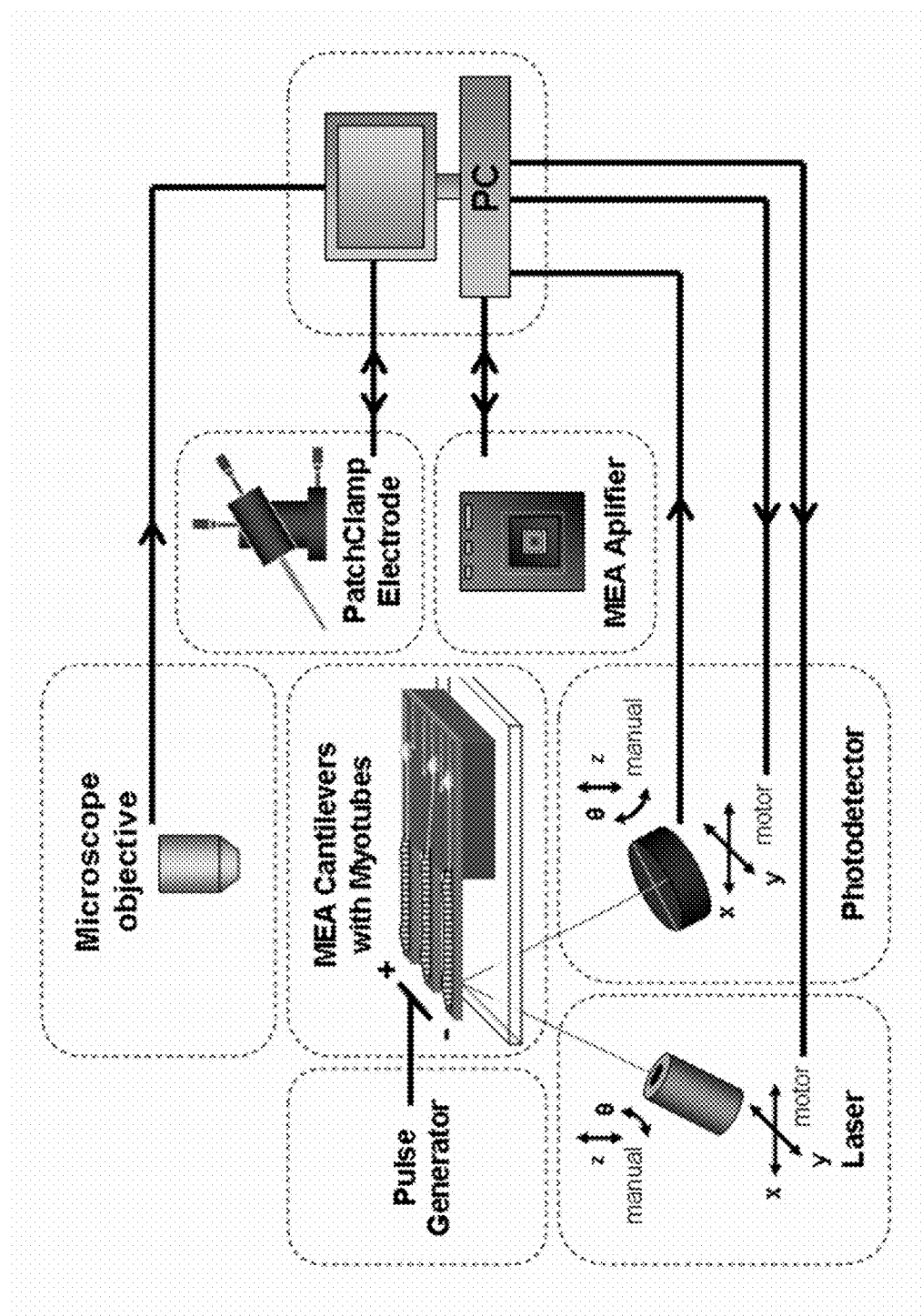
FIG. 17 provides a schematic diagram of a modified setup to address piezoelectric (or piezoresistive) microcantilevers with an MEA amplifier.
Figure 18B:
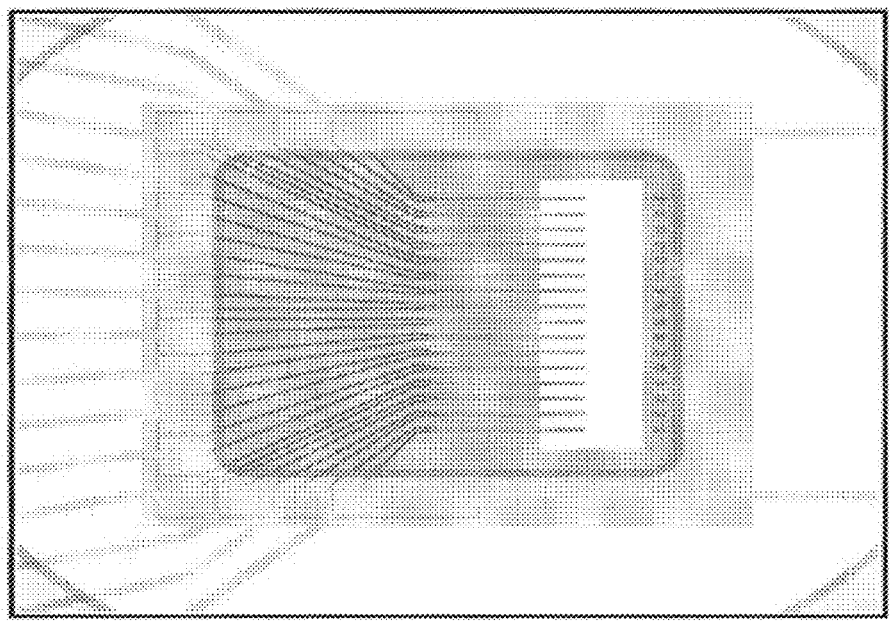
FIGS. 18A-B show a top view of a multiplexed 24 well plate system (FIG. 18A) providing 16 microcantilevers per well; shown in an enlarged view (FIG. 18B); the size of the cartridge is the same as in a 96 well plate.
Figure 18A:
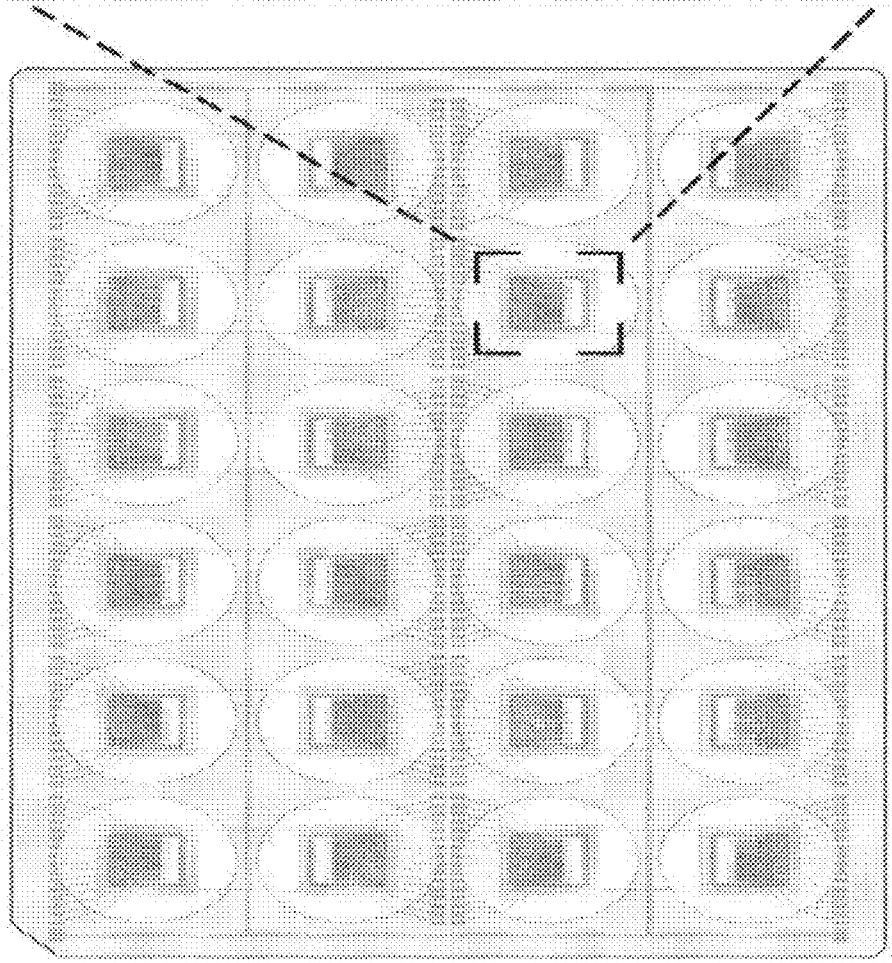

Silicon wafers with silicon on insulator serve as base material in the fabrication of piezoelectric cantilevers. An additional layer of 100-200 nm SiO$_2$ is deposited onto the base material to insulate conductive materials from the semi-conductive silicon. Subsequent fabrication steps are depicted in FIG. 16A (left). Metal layers are fabricated to connect the piezoelectric components with microelectronics. Layers of piezoelectric materials, such as ZnO and PTZ sol-gel, are deposited exactly in those areas where microcantilevers remain after the etching process. Another conductive layer contacts the piezoelectric components from top to apply voltages for actuation or current read out during sensor mode. An insulation layer of silicon-ONO-stacks (oxide-nitride-oxide) protects conductive elements from aqueous solutions during cell culture. An alternative approach is presented in FIG. 16A (right), where piezoelectric elements are replaced by piezoresistive materials. This alternative approach offers a higher sensitivity during readout, however, piezoresistive materials do not provide the usage of the cantilevers as actuators and the field stimulator would then have to be retained in the system.

Piezoelectric cantilevers are characterized using the current laser system. The sensor application for the detection of microcantilever deflection by an external force is compared to laser measurements and the actuator application of cantilevers by the inverse piezoelectric effect is monitored by the laser system as well. Representative experiments using embryonic rat cells are being repeated with the piezoelectric cantilever system and monitored in parallel by the laser system. The skilled should know that due to a different surface texture caused by additional piezoelectric layers under an insulating silicon nitride surface, small variations in the cell culture protocols may be necessary to optimize the cell attachment. Due to additional piezoelectric and insulating layers on cantilevers, differences between standard cantilevers and piezoelectric cantilevers during laser measurements are expected. Finding and quantifying these differences are part of the characterization process for piezoelectric cantilevers. Characterization of the cell morphology and surface chemistry is as described above. Experiments with the three cell types described above to verify that the surface chemistry and myotube differentiation are not altered significantly due to the change in bulk surface composition of SAM formulation after force transduction testing and confirm the systems are equivalent.

The additional layers on cantilevers are expected to cause some mechanical stress resulting in slightly bent cantilevers. The variation of pre-deflection due to intrinsic tress is expected to be close to constant across the wafer, allowing for a determination of an average pre-deflection by microscopic (SEM) means. The pre-deflection of cantilevers can be considered as an advantage. In order to deflect a straight cantilever myotubes initially need to develop intense forces, whereas slightly pre-deflected cantilevers allow for a better myotube-force to cantilever-deflection ratio. Using the reverse piezoelectric effect, a pre-deflection of cantilevers could be eliminated by applying a bias voltage. Further, measurements with piezoelectric cantilevers are expected to have a higher noise level as compared to results obtained with the laser system. However, the scalability of experiments using piezoelectric cantilevers increases the amount of data that can be obtained and thus compensates for noise by statistical means. As an alternative approach we propose the usage of piezoresistive elements (see FIG. 16). The sensitivity of piezoresistive cantilevers is expected to be in between the piezoelectric and the laser approach. Experiments based on piezoelectric cantilevers used as actuators cannot be conducted with piezoresistive cantilevers. Thus the piezoresistive approach is considered as an alternative to allow at least the minimalization of the current system. As another alternative, if the surface modification on the materials used to create piezoelectrics is not acceptable for cell growth, the skilled may want to try a number of solutions. An extra step of oxygen plasma treatments could be added to create more hydroxyl groups on the surface for the silane modification. Also, derivatization with DETA and addition of vitronectrin to the surface could be tried, as we have previously shown this promotes surface myotube formation (Molnar et al. 2007).

Conclusions

The present disclosure demonstrates the development of a novel Bio-MEMS device based on the use of microfabricated silicon microcantilevers and alkylsilane surface chemistry for the study of skeletal muscle and its development. The usefulness of this device has been demonstrated for real-time interrogation of cultured skeletal muscle and the quantification contractile stress and kinetics. It has also been shown that physiological phenomena can be monitored and quantified, and responds to exogenously applied factors.

Cultured myocytes on silicon microcantilevers coated with DETA spontaneously differentiate into functional myotubes that produce contractile stress sufficient to deflect the microcantilevers. These deflections were then measured using a laser detection system. By applying electrical field stimulation, it was possible to selectively actuate the myotubes on microcantilevers in a frequency and intensity dependent manner. This ability to selectively actuate a microcantilever is advantageous as it allows a high degree of control over the timing and nature of contraction.

This method could also be applied to create bio-robotic devices using skeletal muscle as an actuator on a microfabricated device. Previous studies have utilized cardiomyocytes to provide mechanical force. However, cardiac tissue contracts in a primarily spontaneously manner unlike skeletal muscle which remains inactive in the absence of stimulating inputs. Also, skeletal muscle is preferable over cardiac muscle due to its rate-response characteristics. As stimulation frequencies increase, contraction frequency and force generation of skeletal muscle will also increase until tetanus is induced, resulting in tonic contraction. Cardiac muscle, on the other hand, will cease to contract under high frequency stimulation, a situation similar to that of cardiac infarction.

This technique holds particular promise for applications in drug discovery and as a model for various diseases involving skeletal muscle. The development of an in vitro model for functional biological circuits would greatly benefit the broader scientific community and society in general. By creating lab-on-chip systems that allow high-throughput, real-time experimentation, research costs would be reduced, data collection and analysis would be simplified, and the need for costly and ethically questionable animal studies would be reduced.

According to the above description and in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES CITED

Alexander, S., L. Hellemans, 0. Marti, J. Schneir and V. Elings (1989). "An atomic-resolution atomic-force microscope implemented using an optical lever." *Journal of Applied Physics* 65(1): 164.

Archer, J. D., C. C. Vargas and J. E. Anderson (2006). "Persistent and improved functional gain in mdx dystrophic mice after treatment with L-arginine and deflazacort." *The FASEB Journal* 20: 738-740.

Bodine, S. C., E. Latres, S. Baumhueter, V. K. Lai, L. Nunez, B. A. Clarke, W. T. Puoueymirou, F. J. Panaro, E. Na, K. Dharmarajan, Z. Q. Pan, D. M. Valenzuela, T. M. DeChiara, T. N. Stitt, G. D. Yancopoulos and D. J. Glass (2001). "Identification of ubiquitin ligases required for skeletal muscle atrophy." *Science* 294: 1704-1708.

Brewer, G. J., M. D. Boehler, T. T. Jones and B. C. Wheeler (2008). "NbActiv4 medium improvement to Neurobasal/B27 increases neuron synapse densities and network spike rates on multielectrode arrays." *J Neurosci Methods* 170 (2): 181-7.

Briggs, M. P., Seah, M. P. (1992). *Practical Surface Analysis by Auger and X-ray Photoelectron Spectroscopy*. New York, John Wiley and Sons.

Butt, H.-J. A. (1996). "Sensitive Method to Measure Changes in the Surface Stress of Solids." *Journal of Colloid and Interface Science* 180(1): 251-260.

Caiozzo, V. J., R. E. Herrick and K. M. Baldwin (1992). "Response of slow and fast muscle to hypothyroidism: maximal shortening velocity and mysoin isoforms." *American Journal of Physiology* 263: C86-C94.

Catoire, H., M. Y. Pasco, A. Abu-Baker, S. Holbert, C. Tourette, B. Brais, G. A. Rouleau, J. A. Parker and C. Neri (2008). "Sirtuin inhibition protects from the polyalanine muscular dystrophy protein PABPN1." *Human Mol. Genetics* 17: 2108-2117.

Collins, C. A. and J. E. Morgan (2003). "Duchenne's muscular dystrophy: animal models used to investigate pathogenesis and develop therapeutic strategies." *Int J Exp Pathol* 84: 165-172.

Courdier-Fruh, I., L. Barman, A. Briguet and T. Meier (2002). "Glucocorticoid-mediated regulation of utrophin levels in human muscle fibers." *Neuromuscul Disord* 12(Suppl 1): S95-104.

Cross-Doersen, D. and R. J. Isfort (2003). "A novel cell-based system for evaluating skeletal muscle cell hypertrophy-inducing agents." *In Vitro Cell Dev Biol Animal* 39: 407-412.

Daniels, M. P. (1990). "Localization of actin, beta-spectrin, 43×10(3) Mr and 58×10(3) Mr proteins to receptor-enriched domains of newly formed acetylcholine receptor aggregates in isolated myotube membranes." *J Cell Sci* 97(Pt 4): 615-26.

Das, M., C. A. Gregory, P. Molnar, L. M. Riedel and J. J. Hickman (2006). "A defined system to allow skeletal muscle differentiation and subsequent integration with silicon microstructures." *Biomaterials* 27(24): 4374-4380

Das, M., J. W. Rumsey, N. Bhargava, M. Stancescu and J. J. Hickman (2009). "Skeletal Muscle Tissue Engineering: An Improved Model Promoting Long Term Survival of Myotubes, Structural Development of E-C Coupling Apparatus and Neonatal Myosin Heavy Chain (MHC) Expression." *Biomaterials* 30: 5392-5402.

Das, M., K. Wilson, P. Molnar and J. J. Hickman (2007). "Differentiation of skeletal muscle and integration of myotubes with silicon microstructures using serum-free medium and a synthetic silane substrate." *Nature Protocols* 2(7): 1795-1801.

de Lange, P., P. Farina, M. Moreno, M. Ragni, A. Lombardi, E. Silvestri, L. Burrone, A. Lanni and F. Goglia (2006). "Sequential changes in the signal transduction responses of skeletal muscle following food deprivation." *FASEB J.* 20(14): 2579-2581.

de Wilde, J., R. Mohren, S. van den Berg, M. Boekschoten, K. W.-V. Dijk, P. de Groot, M. Muller, E. Mariman and E. Smit (2008). "Short-term high fat-feeding results in morphological and metabolic adaptations in the skeletal muscle of C57BL/6J mice." *Physiol. Genomics* 32(3): 360-369.

Dennis, R. G. and I. P. E. Kosnik (2000). "Excitability and isometric contractile properties of mammalian skeletal muscle constructs engineered in vitro." *In Vitro Cellular Developmental Biology—Animal* 36(5): 327-335.

Dennis, R. G., P. E. Kosnik, M. E. Gilbert and J. A. Faulkner (2001). "Excitability and contractility of skeletal muscle engineered from primary cultures and cell lines." *Am J Physiol Cell Physiol* 280: C288-C295.

Eisen, A. and M. Swash (2001). "Clinical neurophysiology of ALS." *Clinical Neurophysiology* 112(12): 2190-2201.

Eschenhagen, T. and W. H. Zimmermann (2005). "Engineering myocardial tissue." *Circ Res* 97: 1220 -1231.

Gaud, A., J. M. Simon, T. Witzel, M. Carre-Pierrat, C. G. Wermuth and L. Segalat (2004). "Prednisone reduces muscle degeneration in dystrophin-deficient Caenorhabditis elegans." *Neuromuscul Disord* 14: 365-370.

Glass, D. J. (2003). "Signalling pathways that mediate skeletal muscle hypertrophy and atrophy." *Nat Cell Biol* 5: 87-90.

Gordon, A. M., E. Homsher and M. Regnier (2000). "Regulation of Contraction in Striated Muscle." *Physiol Rev* 80(2): 853-924.

Graham, S. C., R. R. Roy, C. Navarro, B. Jiang, D. Pierotti, S. Bodine-Fowler and V. R. Edgerton (1992). *Muscle Nerve* 15(1): 27-36.

Granchelli, J. A., C. Pollina and M. S. Hudecki (2000). "Pre-clinical screening of drugs using the mdx mouse." *Neuromuscul Disord* 10: 235-239.

Hennessey, J. V., J. A. Chromiak, S. DellaVentura, S. E. Reinert, J. Puhl, D. P. Kiel, C. J. Rosen, H. Vandenburgh and D. B. Maclean (2001). "Growth hormone administration and exercise effects on muscle fiber type and diameter in moderately frail older people." *J Am Geriatr Soc* 49: 852-858.

Hermann, M., M. P. Bogsrud, E. Molden, A. Asberg, B. U. Mohebi, L. Ose and K. Retterstol (2006). "Exposure of atorvastatin is unchanged but lactone and acid metabolites are increased several-fold in patients with atorvastatin-induced myopathy." *Clin Pharmacol Ther* 79: 532-539.

Hickman, J. J., S. K. Bhatia, J. N. Quong, P. Shoen, D. A. Stenger, C. J. Pike and C. W. Cotman (1994). "Rational Pattern Design for in-Vitro Cellular Networks Using Surface Photochemistry." *Journal of Vacuum Science & Technology a-Vacuum Surfaces and Films* 12(3): 607-616.

Hoffman, E. P. and D. Escolar (2006). "Translating mighty mice into neuromuscular therapeutics: is bigger muscle better?" *Am J Pathol* 168: 1775-1778.

Holler, F. J., D. A. Skoog and S. R. Crouch (2007). Chapter 1. *Principles of Instrumental Analysis*, Cengage Learning: 9.

Huang, Y.-C., R. G. Dennis, L. Larkin and K. Baar (2005). "Rapid formation of functional muscle in vitro using fibrin gels." *J Appl Physiol* 98(2): 706-713.

Huxley, A. F. (1975). "The origin of force in skeletal muscle." *Ciba Found Symp* 31: 271-290.

Investigators, T. S. P. b. A. R. i. C. L. S. (2006). "High-dose atorvastatin after stroke or transient ischemic attack." *N Engl J Med* 355: 549-559.

Izumiya, Y., T. Hopkins, C. Morris, K. Sato, L. Zeng, J. Viereck, J. A. Hamilton, N. Ouchi, N. K. LeBrasseur and K. Walsh (2008). "Fast/glycolytic muscle fiber growth reduces fat mass and improves metabolic parameters in obese mice." *Cell Metabolism* 7(2): 159-172.

Jiang, Z. and P. R. Clemens (2006). "Cellular caspase-8-like inhibitory protein (cFLIP) prevents inhibition of muscle cell differentiation induced by cancer cells." *FASEB J* 20: 2570-2572.

Johnson, T. E., X. Zhang, S. Shi and D. R. Umbenhauer (2005). "Statins and PPARalpha agonists induce myotoxicity in differentiated rat skeletal muscle cultures but do not exhibit synergy with cotreatment." *Toxicol Appl Pharmacol* 208: 210-221.

Kaufman, P., M. Torok, A. Zahno, K. M. Waldhauser, K. Brecht and S. Krahenbuhl (2006). "Toxicity of statins on rat skeletal muscle mitochondria." *Cell Mol Life Sci* 63: 2415-2425.

Khademhosseini, A., R. Langer, J. Borenstein and J. P. Vacanti (2006). "Microscale technologies for tissue engineering and biology." *Proc. Natl. Acad. Sci. USA* 103: 2480-2487.

Kidd, J. (2006). "Life after statin patent expiries." *Nat Rev Drug Discov* 5: 813-814.

King, T., M. Pozzi and A. Manara (2000). "Piezoactuators for 'real-world' applications—Can they deliver sufficient displacement?" *Power Engineering* 14(3): 105-110.

Kosnik, P. E., R. G. Dennis and H. H. Vandenburgh (2003). Tissue engineering skeletal muscle. *Functional tissue engineering*. F. Guilak, D. L. Butler, S. A. Goldstein and D. J. Mooney. New York, Springer: 377-392.

Kucera, J. (1982a). "One-bag-fiber muscle spindles in tenuissimus muscles of the cat." *Histochemistry and Cell Biology* 76(3): 315-328.

Kucera, J. (1982b). "The topography of long nuclear chain intrafusal fibers in the cat muscle spindle." *Histochemistry* 74(2): 183-197.

Kucera, J. (1983). "Multiple-bag-fiber muscle spindles in tenuissimus muscles of the cat." *Histochemistry* 79(3): 457-476.

Kucera, J. and K. Dorovini-Zis (1979). "Types of human intrafusal muscle fibers." *Muscle Nerve* 2(6): 437-451.

Kuhl, U., R. Timpl and K. von der Mark (1982). "Synthesis of type IV collagen and laminin in cultures of skeletal muscle cells and their assembly on the surface of myotubes." *Dev Biol* 93(2): 344-54.

Langer, R. and J. P. Vacanti (1993). "Tissue engineering." *Science* 260: 920-926.

Larsson, L. and T. Ansved (1995). "Effects of ageing on the motor unit." *Progress in Neurobiology* 45(5): 397-415.

Liu, J., J. W. Rumsey, P. Molnar, M. Das, C. Gregory, L. Riedel and J. J. Hickman (2008). "Electrophysiological and Immunocytochemical Characterization of DRG Neurons on an Organosilane Surface in Serum Free Medium." *In Vitro Cellular & Developmental Biology* 44: 162-168.

Lou, X. J. (2009). "Polarization fatigue in ferroelectric thin films and related materials." *Journal of Applied Physics* 105: 024101-1.

Malerba, A., L. Vitiello, D. Segat, E. Dazzo, M. Frigo, I. Scambi, P. De Coppi, L. Boldrin, L. Martelli, A. Pasut, C. Romualdi, R. G. Bellomo, J. Vecchiet and M. D. Baroni (2009). "Selection of multipotent cells and enhanced muscle reconstruction by myogenic macrophage-secreted factors." *Exp Cell Res* 315(6): 915-27.

Malo, N., J. A. Hanley, S. Cerquozzi, J. Pelletier and R. Nadon (2006). "Statistical practice in high-throughput screening data analysis." *Nat Biotechnol* 24: 167-175.

Matsakas, A. and K. Patel (2009). "Skeletal muscle fibre plasticity in response to selected environmental and physiological stimuli." *Histol Histopathol* 24(5): 611-629.

Matthews, P. B. (1964). "Muscle spindles and their motor control." *Physiol Rev* 44: 219-288.

Matzno, S., K. Tazuya-Murayama, H. Tanaka, S. Yasuda, M. Mishima, T. Uchida, T. Nakabayashi and K. Matsuyama (2003). "Evaluation of the synergistic adverse effects of concomitant therapy with statins and fibrates on rhabdomyolysis." *J Pharm Pharmacol* 55: 795-802.

Meyer, G. and M. A. Nabil (1988). "Novel optical approach to atomic force microscopy." *Applied Physics Letters* 53(12): 1045-1047.

Molnar, P., W. Wang, A. Natarajan, J. W. Rumsey and J. J. Hickman (2007). "Photolithographic Patterning of C2C12 Myotubes using Vitronectin as Growth Substrate in Serum-Free Medium." *Biotechnology Progress* 23(1): 265-268.

Moulard, G., G. Contoux, G. Motyl, G. Gardet and M. Courbon (1998). "Improvement of the cantilever beam technique for stress measurement during the physical vapor deposition process." *Journal of Vacuum Science & Technology A: Vacuum, Surfaces, and Films* 16(2): 736-742.

Müller, P. and A. Saúl (2004). "Elastic effects on surface physics." *Surface Science Reports* 54(5-8): 157-258.

Murgia, M., A. Serrano, E. Calabria, G. Pallafacchina, T. Lomo and S. Schiaffino (2000). "Ras is involved in nerve-activity-dependent regulation of muscle genes." *Nat Cell Biol.* 2(3): 142-7.

Mutyala, M. S. K., D. Bandhanadham, L. Pan, V. R. Pendyala and H.-F. Ji (2009). "Mechanical and electronic approaches to improve the sensitivity of microcantilever sensors." *Acta Mechanica Sinica* 25(1): 1-12.

Nelson, C., M. and M. Bissell, J. (2006). "Of extracellular matrix, scaffolds, and signaling: tissue architecture regulates development, homeostasis, and cancer." *Annu Rev Cell Dev Biol* 22: 287-309.

Nelson, P. G., R. D. Fields, C. Yu and Y. Liu (1993). "Synapse elimination from the mouse neuromuscular junction in vitro: a non-Hebbian activity-dependent process." *J Neurobiol* 24(11): 1517-30.

Olson, E. N. and R. Williams, S. (2000). "Calcineurin Signaling and Muscle Remodeling." *Cell* 101(7): 689-692.

Parng, C., W. L. Seng, C. Semino and P. McGrath (2002). "Zebrafish: A Preclinical Model for Drug Screening." *ASSAY and Drug Development Technologies* 1: 41-48.

Payne, E. T., N. Yasuda, J. M. Bourgeois, M. C. Devries, M. C. Rodriguez, J. Yousuf and M. A. Tarnopolsky (2006). "Nutritional therapy improves function and complements corticosteroid intervention in mdx mice." *Muscle Nerve* 33: 66-77.

Peterson, C. A., R. K. Workman, D. Sarid, B. Vermeire, H. G. Parks, D. Adderton and P. Maivald (1999). "Effects of moisture on Fowler-Nordheim characterization of thin silicon-oxide films." *Journal of Vacuum Science & Technology A: Vacuum, Surfaces, and Films* 17(5): 2753-2758.

Pette, D., J. Sketelj, D. Skorjanc, E. Leisner, I. Traub and F. Bajrovic (2002). "Partial fast-to-slow conversion of regenerating rat fast-twitch muscle by chronic low frequency stimulation." *Journal of Muscle Research and Cell Motility* 3: 215-221.

Pette, D. and R. S. Staron (2001). "Transitions of muscle fiber phenotypic profiles." *Histochemistry and Cell Biology* 115(5): 359-372.

Powell, C., J. Shansky, M. DelTatto, D. E. Forman, J. Hennessey, K. Sullivan, B. A. Zielinski and H. H. Vandenburgh (1999). "Tissue engineered human bioartificial muscles expressing a foreign recombinant protein for gene therapy." *Human Gene Therapy* 10: 565-577.

Powell, C., B. Smiley, J. Mills and H. Vandenburgh (2002). "Mechanical stimulation improves tissue-engineered human skeletal muscle." *Am J Physiol Cell Physiol* 283: C1557-C1565.

Raiteri, R., M. Grattarola, H. J. Butt and P. Skladal (2001). "Micromechanical cantilever-bsed biosensors." *Sensors and Actuators B-Chemical* 79: 115-126.

Ravenscroft, M. S., K. E. Bateman, K. M. Shaffer, H. M. Schessler, D. R. Jung, T. W. Schneider, C. B. Montgomery, T. L. Custer, A. E. Schaffner, Q. Y. Liu, Y. X. Li, J. L. Barker and J. J. Hickman (1998). "Developmental neurobiology implications from fabrication and analysis of hippocampal neuronal networks on patterned silane-modified surfaces." *Journal of the American Chemical Society* 120(47): 12169-12177.

Rumsey, J. W., M. Das, J. F. Kang, R. Wagner, P. Molnar and J. J. Hickman (2008). "Tissue Engineering Intrafusal Fibers: Dose and Time Dependent Differentiation of Nuclear Bag Fibers in a Defined In Vitro System using Neuregulin 1-β-1." *Biomaterials* 29: 994-1104.

Sander, D., A. Enders and J. Kirschner (1995). "A simple technique to measure stress in ultrathin films during growth." *Review of Scientific Instruments* 66(9): 4734.

Schiaffino, S., M. Sandri and M. Murgia (2007). "Activity-Dependent Signaling Pathways Controlling Muscle Diversity and Plasticity." *Physiology* 22(4): 269-278.

Schiaffino, S. and A. Serrano (2002). "Calcineurin signaling and neural control of skeletal muscle fiber type and size." *Trends Pharmacol Sci* 23(12): 569-75.

Schneider, A. G., K. R. Sultan and D. Pette (1999). "Muscle LIM protein: expressed in slow muscle and induced in fast muscle by enhanced contractile activity." *American Journal of Physiology* 276: C900-906.

Scott, W., J. Stevens and S. A. Binder-Macleod (2001). "Human Skeletal Muscle Fiber Type Classifications." *Physical Therapy* 81(11): 1810-1816.

Semsarian, C., M. J. Wu, Y. K. Ju, T. Marciniec, T. Yeoh, D. G. Allen, R. P. Harvey and R. M. Graham (1999). "Skeletal muscle hypertrophy is mediated by a Ca2+-dependent calcineurin signalling pathway." *Nature* 400: 576-581.

Shainberg, A., S. A. Cohen and P. G. Nelson (1976). "Induction of acetylcholine receptors in muscle cultures." *Pflugers Arch* 361(3): 255-61.

Shansky, J., B. Creswick, P. Lee, X. Wang and H. Vandenburgh (2006a). "Paracrine release of insulin-like growth factor 1 from a bioengineered tissue stimulates skeletal muscle growth in vitro." *Tissue Eng* 12: 1833-1841.

Shansky, J., M. Del Tatto, J. Chromiak and H. Vandenburgh (1997). "A simplified method for tissue engineering skeletal muscle organoids in vitro." *In Vitro Cell Dev Biol Animal* 33: 659-661.

Shansky, J., P. Ferland, S. McGuire, C. Powell, M. Del Tatto, M. Nachman, J. Hennessey and H. Vandenburgh (2006b). Tissue engineering human skeletal muscle for clinical applications. *Culture of Cells for Tissue Engineering*. G. Vunjak and I. Freshney.

Smith, P. F., R. S. Eydelloth, S. J. Grossman, R. J. Stubbs, M. S. Schwartz, J. I. Germershausen, K. P. Vyas, P. H. Kari and J. S. MacDonald (1991). "HMG-CoA reductase inhibitor-induced myopathy in the rat: cyclosporine A interaction and mechanism studies." *J Pharmacol Exp Ther* 257: 1225-1235.

Spargo, B. J., M. A. Testoff, T. B. Nielsen, D. A. Stenger, J. J. Hickman and A. S. Rudolph (1994). "Spatially controlled adhesion, spreading, and differentiation of endothelial cells on self-assembled molecular monolayers." *Proc Natl Acad Sci U S A* 91(23): 11070-11074.

Steffen, L. S., J. R. Guyon, E. D. Vogel, R. Beltre, T. J. Pusack, Y. Zhou, L. I. Zon and L. M. Kunkel (2007). "Zebrafish orthologs of human muscular dystrophy genes." *BMC Genomics* 8: 79.

Stenger, D. A., J. H. Georger, C. S. Dulcey, J. J. Hickman, A. S. Rudolph, T. B. Nielsen, S. M. McCort and J. M. Calvert (1992). "Coplanar Molecular Assemblies of Aminoalkylsilane and Perfluorinated Alkylsilane—Characterization and Geometric Definition of Mammalian-Cell Adhesion and Growth." *Journal of the American Chemical Society* 114(22): 8435-8442.

Stoney, G. G. (1909). "The Tension of Metallic Films Deposited by Electrolysis." *Proc. Roy. Soc. London* 82(Ser. A): 172-175.

Tanaka, M., R. Bateman, D. Rauh, E. Vaisberg, S. Ramachandani, C. Zhang, K. C. Hansen, A. L. Burlingame, J. K. Trautman, K. M. Shokat and C. L. Adams (2005). "An Unbiased Cell Morphology Based Screen for New, Biologically Active Small Molecules." *PLoS Biology* 3: e128.

Termin, A. and D. Pette (1992). "Changes in myosin heavy-chain isoform synthesis of chronically stimulated rat fast-twitch muscle." *European Journal of Biochemistry* 204(2): 569-573.

Terstappen, G. C., C. Schlupen, R. Raggiaschi and G. Gaviraghi (2007). "Target deconvolution strategies in drug discovery." *Nat. Rev. Drug Discov* 6: 891-903.

Thompson, P. D., P. M. Clarkson and R. S. Rosenson (2006). "An assessment of statin safety by muscle experts." *Am J Cardiol* 97: 69C-76C.

Tobert, J. A. (2003). " Lovastatin and beyond: the history of the HMGCoA reductase inhibitors." *Nat Rev Drug Discov* 2: 517-526.

Vandenburgh, H., J. Shansky, F. Benesch-Lee, V. Barbata, J. Reid, L. Thorrez, R. Valentini and G. Crawford (2008). "A drug screening platform based on the contractility of tissue engineered muscle." *Muscle Nerve* 37: 438-447.

Vandenburgh, H., J. Shansky, F. Benesch-Lee, K. Skelly, J. Spinazzola, Y. Saponjian and B. S. Tseng (2009) "Automated drug screening with contractile muscle tissue engineered from dystrophic myoblasts." Volume, DOI:

Vandenburgh, H. H. (1988). "A computerized mechanical cell stimulator for tissue culture: Effects on skeletal muscle organogenesis." *In Vitro* 24: 609-619.

Vandenburgh, H. H., M. Del Tatto, J. Shansky, J. LeMaire, A. Chang, F. Payumo, P. Lee, A. Goodyear and L. Raven (1996). "Tissue engineered skeletal muscle organoids for reversible gene therapy." *Human Gene Therapy* 7: 2195-2200.

Vandenburgh, H. H., S. Swasdison and P. Karlisch (1991). "Computer aided mechanogenesis of skeletal muscle organs from single cells in vitro " *FASEB J* 5: 2860-2867.

Waggoner, P. S. and H. G. Craighead (2007). "Micro- and nanomechanical sensors for environmental, chemical, and biological detection." *Lab On A Chip* 7: 1238-1255.

Wakatsuki, T., J. A. Fee and E. L. Elson (2004). "Phenotypic screening for pharmaceuticals using tissue constructs." *Curr Pharm Biotechnol* 5: 181-189.

Walro, J. M. and J. Kucera (1999). "Why adult mammalian intrafusal and extrafusal fibers contain different myosin heavy-chain isoforms." *Trends in Neurosciences* 22(4): 180-184.

Wende, A. R., P. J. Schaeffer, G. J. Parker, C. Zechner, D.-H. Han, M. M. Chen, C. R. Hancock, J. J. Lehman, J. M. Huss, D. A. McClain, J. O. Holloszy and D. P. Kelly (2007). "A Role for the Transcriptional Coactivator PGC-1α in Muscle Refueling." *Journal of Biological Chemistry* 282: 36642-36651.

Wilson, K., P. Molnar and J. J. Hickman (2007). "Integration of Functional Myotubes with a Bio-MEMS Device for Non-Invasive Interrogation." *Lab-on-a-Chip* 7: 920-922.

Xi, J., J. J. Schmidt and C. D. Montemagno (2005). "Self-assembled microdevices driven by muscle." *Nature Materials* 4: 180-184.

Yasuda, S. I., S. Sugiura, N. Kobayakawa, H. Fujita, H. Yamashita, K. Katoh, Y. Saeki, H. Kaneko, Y. Suda, R. Nagai and H. Sugi (2001). "A novel method to study contraction characteristics of a single cardiac myocyte using carbon fibers." *AMERICAN JOURNAL OF PHYSIOLOGY-HEART AND CIRCULATORY PHYSIOLOGY* 281(3): H1442-H1446.

Zimmermann, W. H., K. Schneiderbanger, P. Schubert, M. Didié, F. Müinzel, J. F. Heubach, S. Kostin, W. L. Neuhuber and T. Eschenhagen (2002). "Tissue Engineering of a Differentiated Cardiac Muscle Construct." *Circulation Research* 90(2): 223-230.

TABLE 1

Comparison of calculated stress values to published literature.
Values for ds/dt are not available in Close et al., but average
force generation has been reported to be more than 1000 fold
higher that measured in Dennis and Kosnik.

| | $\sigma_F$ (kPa) | TPT (ms) | ½ RT (ms) | dσ/dt (Pa/ms) |
|---|---|---|---|---|
| ESM | ~1.1 | 236.8 ± 26.1 | 233.6 ± 23.8 | 7.15 |
| Cultured Myoids | ~2.9 | 69.3 ± 9.4 | 116.4 ± 19.4 | 75.3 ± 10.0 |
| Adult | >300 | 36.0 ± 2.3 | 48.0 ± 3.4 | X |

TABLE 2

Contractile properties of NbActiv4 cultured muscle versus previous
results and published literature. Values for ds/dt are not available
in Close et al., but average force generation has been reported to
be more than 1000 fold higher that measured in Dennis and Kosnik.

| | σF (kPa) | TPT (ms) | ½ RT (ms) | dσ/dt (Pa/ms) |
|---|---|---|---|---|
| ESM | ~1.1 | 236.8 ± 26.1 | 233.6 ± 23.8 | 7.2 |
| NbActiv4 | ~3.2 | 172.1 ± 4.7 | 175.6 ± 3.6 | 35.4 |
| Cultured Myoids | ~2.9 | 69.3 ± 9.4 | 116.4 ± 19.4 | 75.3 ± 10.0 |
| Adult | >300 | 36.0 ± 2.3 | 48.0 ± 3.4 | X |

That which is claimed:

1. A method of quantitatively measuring the physiological response to an agent, comprising:
   culturing a plurality of muscle cells on a piezoelectric microcantilever;
   contacting the muscle cells with the agent, the agent causing the muscle cells to generate contractile stress and deflect the piezoelectric microcantilever;
   measuring the deflection of the piezoelectric microcantilever; and
   correlating the measured deflection to effectiveness of the agent in causing a physiological response.

2. The method of claim 1, wherein measuring the deflection of the piezoelectric microcantilever comprises detecting a piezoelectric signal caused by the deflection of the piezoelectric microcantilever.

3. The method of claim 2, further comprising estimating a contractile stress on the piezoelectric microcantilever based on the measured deflection.

4. The method of claim 3, wherein measuring the deflection of the piezoelectric microcantilever further comprises numerically quantitating deflection of a free end of the piezoelectric microcantilever using a laser and optical sensor.

5. The method of claim 4, wherein numerically quantitating deflection of a free end of the piezoelectric microcantilever further comprises using Stoney's equation to calculate a contractile stress generated by the muscle cells.

6. The method of claim 5, further comprising characterizing contractile stress-piezoelectric signal response of the piezoelectric microcantilever based on the calculated contractile stress generated by the muscle cells.

7. The method of claim 1, wherein the piezoelectric microcantilever is pre-deflected due to intrinsic stress of the piezoelectric microcantilever.

8. The method of claim 7, wherein the piezoelectric microcantilever further comprises at least one of a conductive layer or an insulating layer, wherein the at least one of the conductive layer or the insulating layer causes the intrinsic stress.

9. The method of claim 7, further comprising applying a bias voltage to the piezoelectric microcantilever to eliminate the pre-deflection.

10. The method of claim 1, further comprising coating diethylenetriamine (DETA) on the piezoelectric microcantilever.

11. The method of claim 10, further comprising patterning the DETA on the piezoelectric microcantilever.

12. The method of claim 10, wherein the muscle cells are directly attached to at least a portion of the piezoelectric microcantilever coated with DETA.

13. The method of claim 1, wherein the muscle cells are aligned along a lengthwise extent of the piezoelectric microcantilever.

14. The method of claim 13, wherein the muscles cells form a plurality of myotubes.

15. The method of claim 14, wherein culturing a plurality of muscle cells on a piezoelectric microcantilever further comprises promoting growth of the myotubes along the lengthwise extent of the piezoelectric microcantilever.

16. The method of claim 14, wherein culturing a plurality of muscle cells on a piezoelectric microcantilever further comprises culturing the muscle cells to minimize variations of thickness of the myotubes on the piezoelectric microcantilever.

17. The method of claim 16, wherein a thickness of the myotubes on the piezoelectric microcantilever is greater than about 5 millimeters.

18. The method of claim 16, wherein the thickness of the myotubes on the piezoelectric microcantilever is less than about 15 millimeters.

19. The method of claim 1, wherein the agent comprises at least one of a metabolic inhibitor, a nutritional supplement, a therapeutic compound or composition, an investigational drug, or combinations thereof.

20. The method of claim 1, further comprising culturing the muscle cells in medium comprising creatine, cholesterol, and estrogen.

* * * * *